(12) United States Patent
Ni et al.

(10) Patent No.: US 7,456,152 B2
(45) Date of Patent: Nov. 25, 2008

(54) PEPTIDE INHIBITORS OF THROMBIN AS POTENT ANTICOAGULANTS

(75) Inventors: Feng Ni, Pierrefonds (CA); Dmitri Tolkatchev, Laprairie (CA); Anna Natapova, Montreal (CA); Anatol Koutychenko, Moscow (RU)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 10/546,390

(22) PCT Filed: Feb. 27, 2004

(86) PCT No.: PCT/CA2004/000301

§ 371 (c)(1),
(2), (4) Date: Sep. 26, 2006

(87) PCT Pub. No.: WO2004/076484

PCT Pub. Date: Sep. 10, 2004

(65) Prior Publication Data

US 2007/0042946 A1    Feb. 22, 2007

(51) Int. Cl.
*A61K 38/16*    (2006.01)
*A61K 38/00*    (2006.01)

(52) U.S. Cl. ............................. 514/13; 514/2
(58) Field of Classification Search ........................ None
See application file for complete search history.

(56) References Cited

FOREIGN PATENT DOCUMENTS

EP    0352228 A2 *  1/1990

WO    WO 03/057258  *  7/2003

OTHER PUBLICATIONS

Rezaie et al., calcium inhibition of the activation of protein c by thrombin, 1994, Eur J Biochem, v223, pp. 575-579.*
Slon-usakiewicz et al., 2000, Biochemistry, v39 pp. 2384-2391.*

* cited by examiner

*Primary Examiner*—Anish Gupta
*Assistant Examiner*—Ronald T Niebauer
(74) *Attorney, Agent, or Firm*—Ogilvy Renault LLP

(57) ABSTRACT

The tetrapeptide Phe-Asn-Pro-Arg (SEQ ID NO: 3) is a structurally-optimized sequence for binding to the active site of thrombin. By conjugating this tetrapeptide or variants thereof to a C-terminal fragment of hirudin, we were able to generate a series of new multivalent inhibitors of thrombin containing only genetically encodable natural amino acids. We found that synergistic binding to both the active site and an exosite of thrombin can be enhanced through substitutions of amino acid residues at the $P_4$, $P_3$ and $P_3'$ sites of the active-site directed sequence, Xaa ($P_4$)-Yaa ($P_3$)-Pro ($P_2$)-Arg ($P_1$)-Pro ($P_1'$)-Gln($P_2'$)-Zaa($P_3'$). Complementary to rational design, a phage library was constructed to explore further the residue requirements at the $P_4$, $P_3$ and $P_3'$ sites for multivalent and optimized bridge-binding. Panning of the phage library has led to thrombin-inhibitory peptides possessing strong anticloning activities in the low nanomolar range and yet interfering only partially with the catalytic active site of thrombin. In all, the availability of potent and genetically-encodable polypepticle inhibitors of thrombin opens the door for much wider applications of this clinically-successful class of anticoagulants, e.g. through more cost-effective recombinant peptide production, in areas such as gene therapy as well as to improve clinical efficacy/safety through the incorporation of homing peptides for targeted delivery.

1 Claim, 23 Drawing Sheets

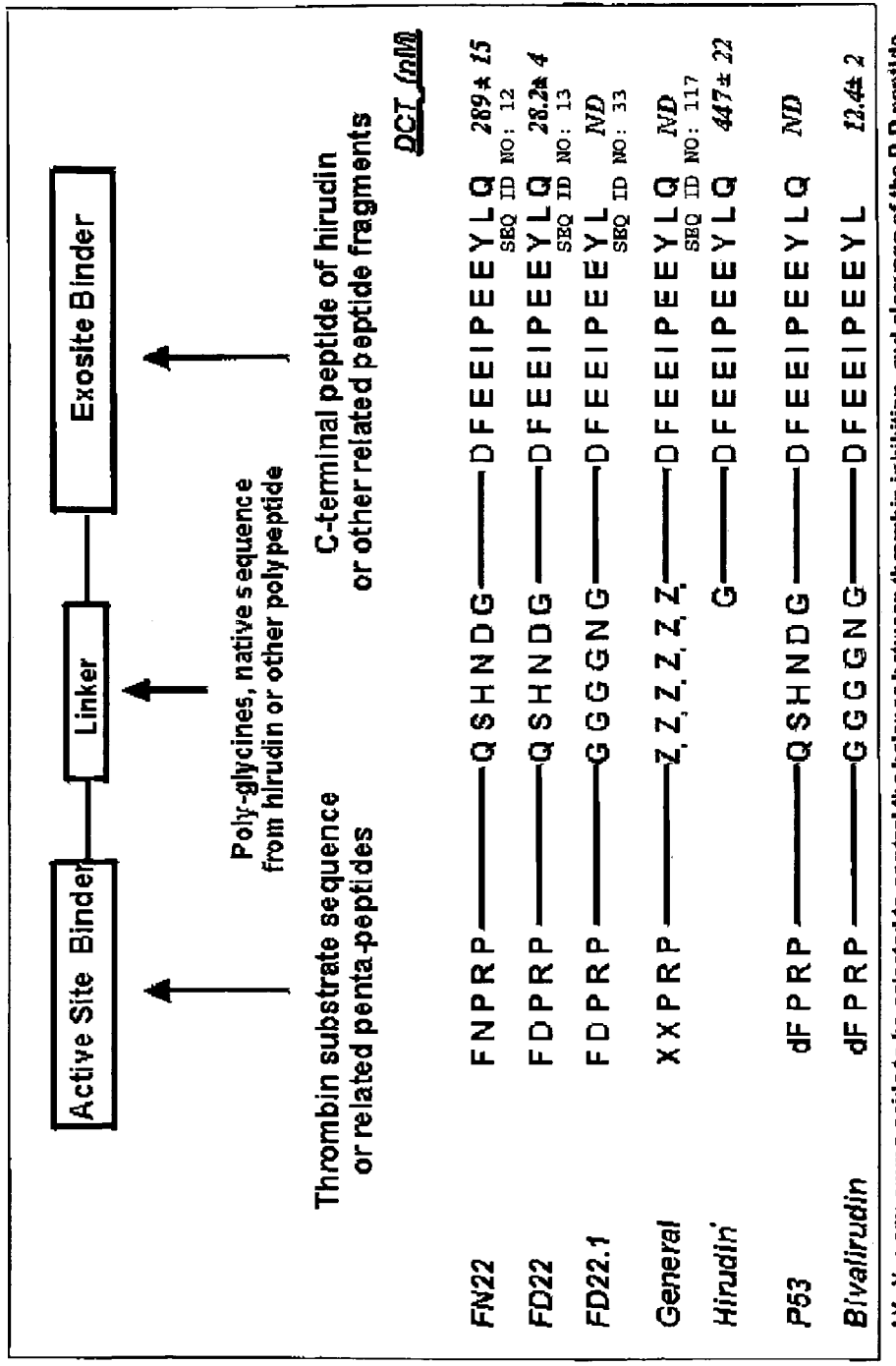
Figure 1. Basic Compositions of FX22 Molecules and Thrombin Inhibition Activities

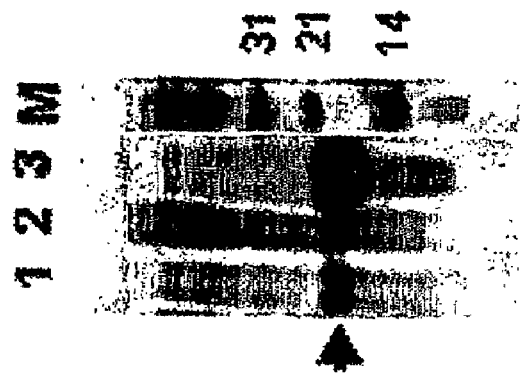

Figure 2: SDS-PAGE (20%) analysis of the expression of the FN22 fusion protein in *E. coli* BL21(DE3) cells. The expression was induced with 1mM IPTG when the cell density reached 0.8-1.0 OD$_{600nm}$ in LB medium. The cells were harvested after additional three hours of growth. M: the low molecular weight marker; Lane 1, the total cell extracts; Lane 2 and Lane 3, the supernatant and the pellet from the fraction purification of the cell lysis. The expressed FN22 fusion proteins were indicated by the arrow.

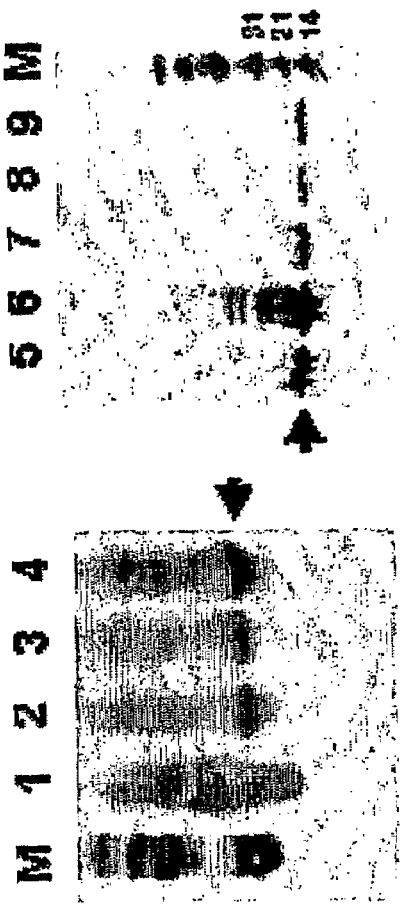

Figure 3: SDS-PAGE (20%) analysis of the expression of FD22 fusion protein in *E. coli* BL21(DE3) cells. The expression was induced with 1mM IPTG when the cell density reached 0.8~1.0 OD...... in LB medium. The cells were harvested after additional three hours of growth. *M*: the low molecular weight marker; *Lane 1*, the cell extracts without IPTG induction; *Lane 2~4*, the cell extracts with IPTG induction; *Lane 5~6*, the partial purification; *Lane 7~9*, the different fractions from the purification by Sep-Pak. The expressed fusion proteins were indicated by the arrows.

HPLC profile of the crude peptides after the FN22 fusion protein was digested by CNBr. The reversed phase semi-preparative column (C18) was used and the sample was eluted with a concentration gradient of acetonitrile from 10% to 70% with a flow rate of 5ml/min. The retention time of FN22 is 17.15 min (the peak was indicated by the asterisk). The wavelength of the detector was set at 278 nm.

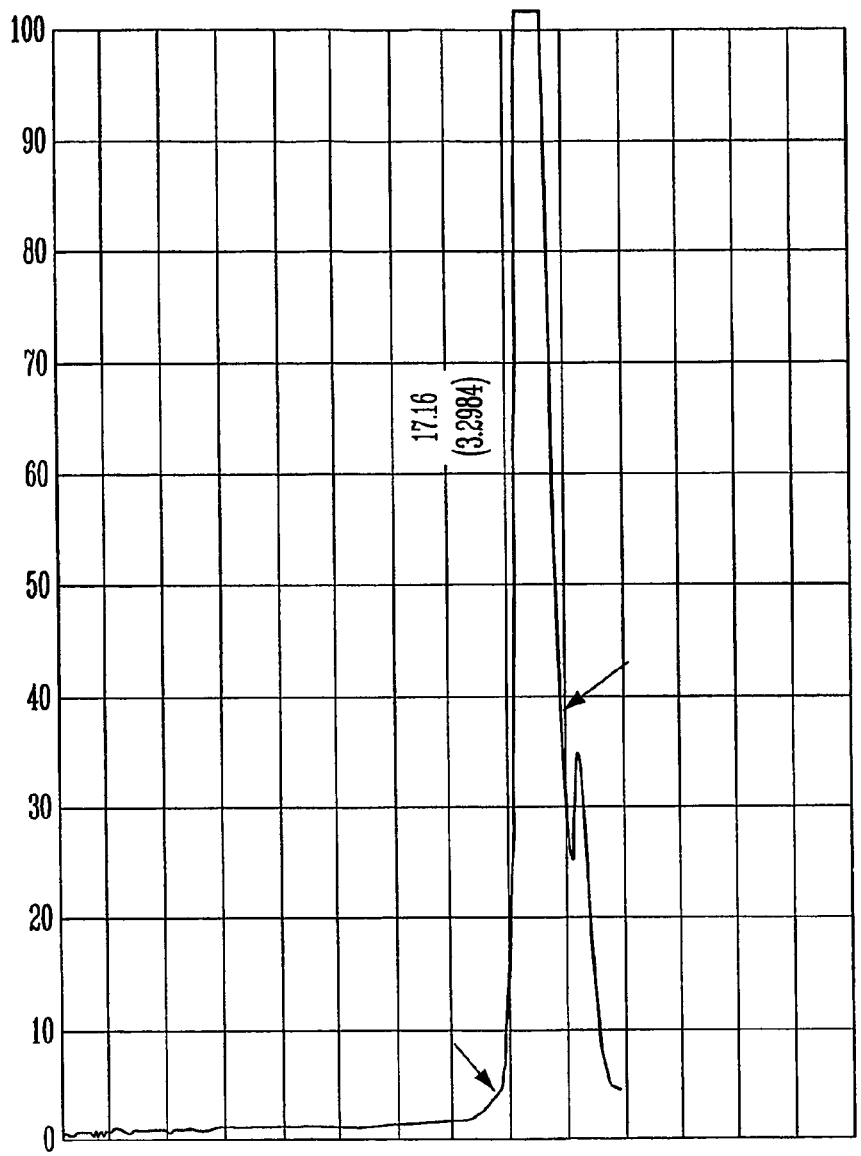

Figure 5

HPLC profile of the second-step purification of FN22. The reversed phase semi-preparative column (C18) was used and the sample was eluted with a concentration gradient of acetonitride from 10% to 70% with a flow rate of 5 ml/min. The wave length of the detector was set at 215 nm. The fraction between the two arrows was collected and the lyophilized product was tested for the inhibition of thrombin in this report.

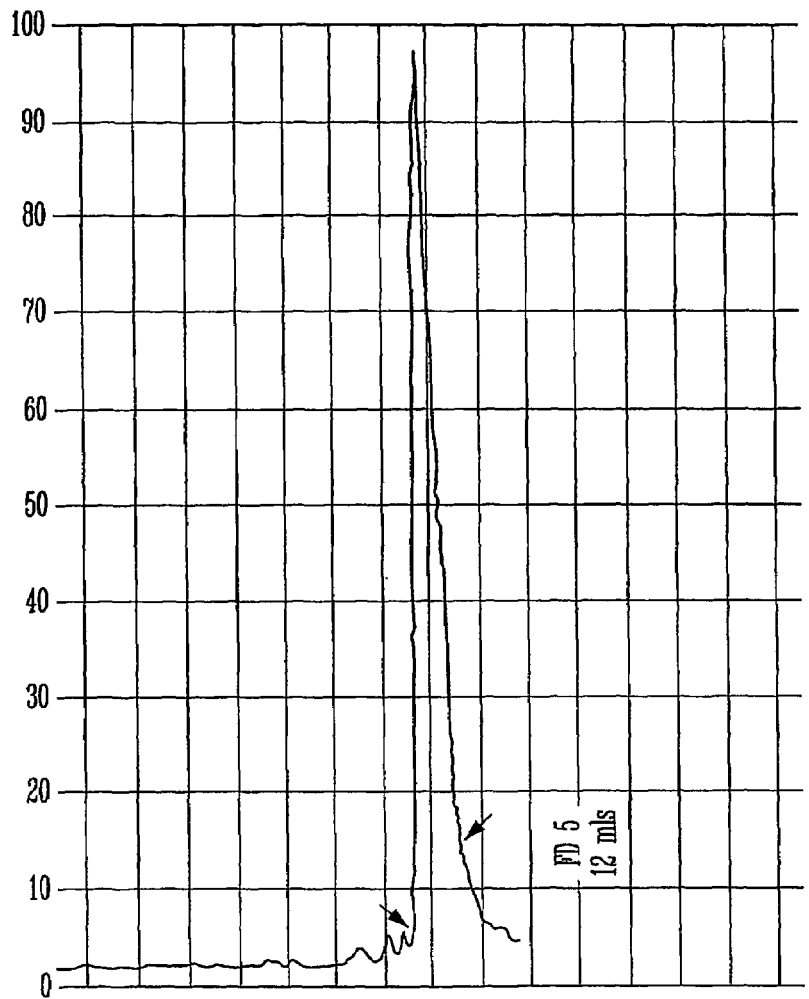

Figure 6

HPL C profile of the second-step purification of FD22. The reversed phase semi-preparative column was used and the sample was eluted with a concentration gradient of concentration of from 10% to 70% with a flow rate of 5 ml/min. The wavelength of the detector was set at 215 nm. The fraction between the two arrows was collected and the lyophilized product was tested for the inhibition of thrombin in this report.

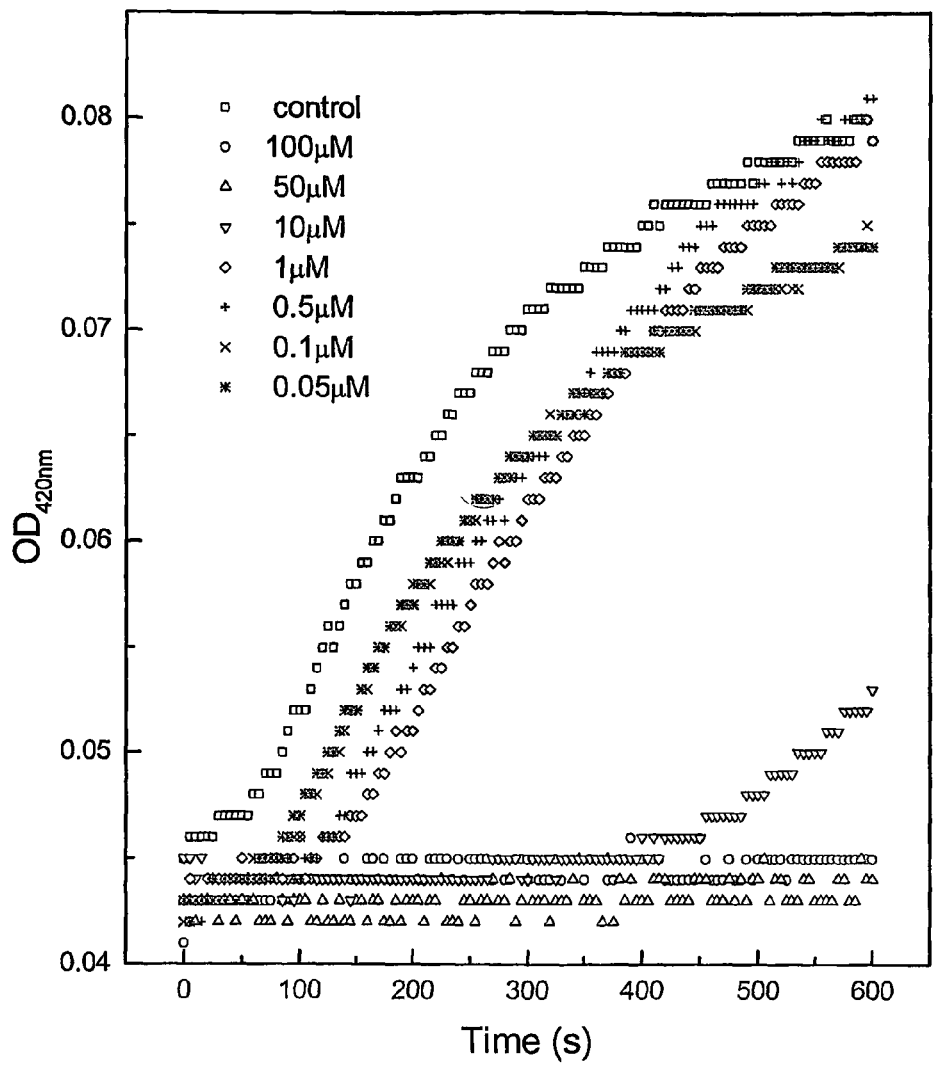
Figure 7. Progression curves for the clotting of human fibrinogen by human thrombin in the presence of varying concentrations of hirudin[54-65].

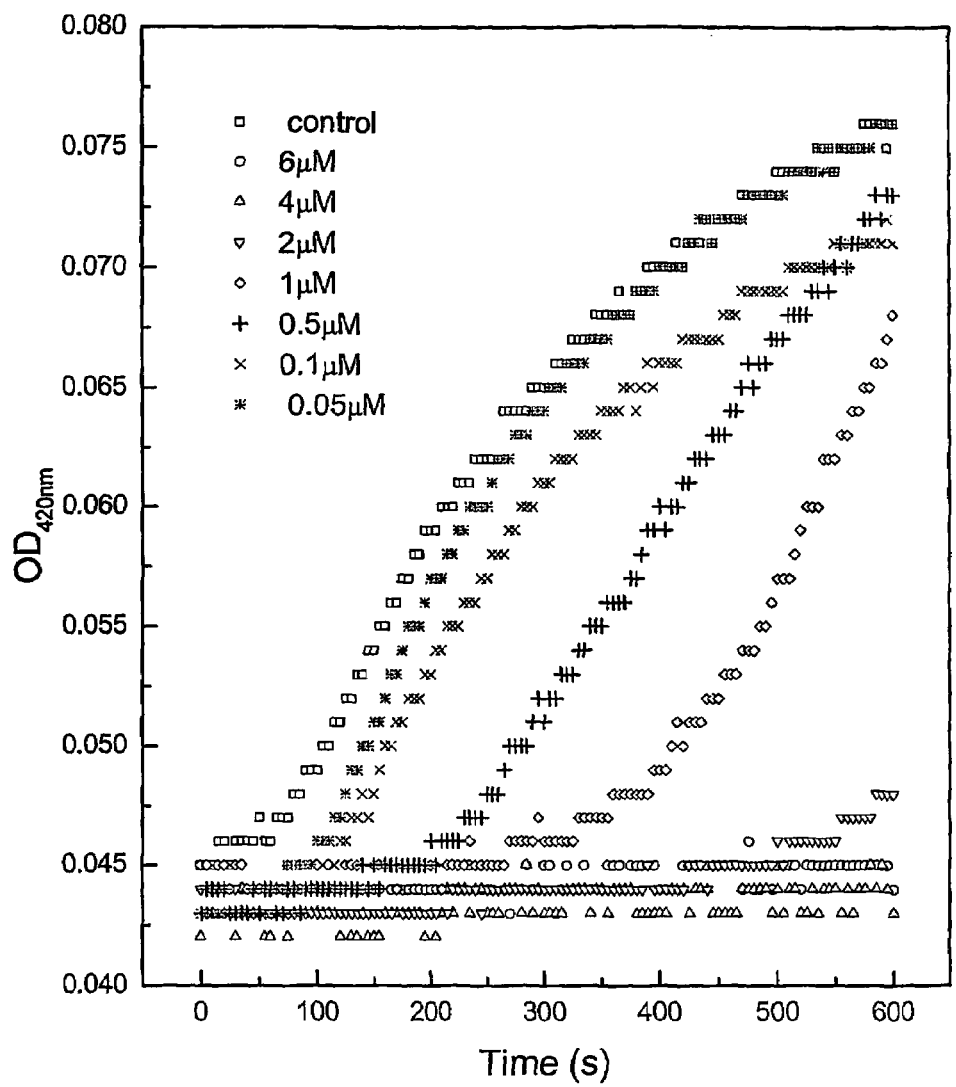
Figure 8. Progression curves of the clotting of human fibrinogen by human thrombin in the presence of varying concentrations of FN22.

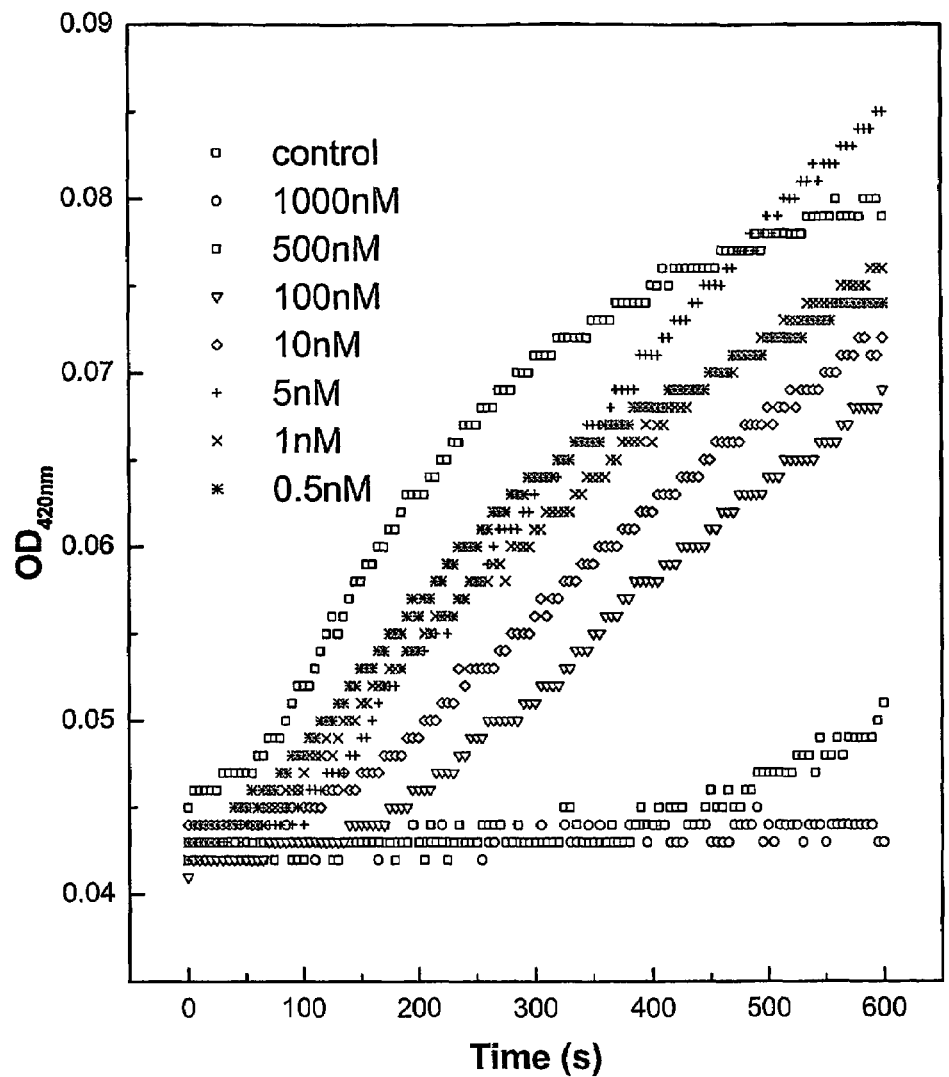
Figure 9. Progression curves for clotting of human fibrinogen by human thrombin in the presence of varying concentrations of FD22.

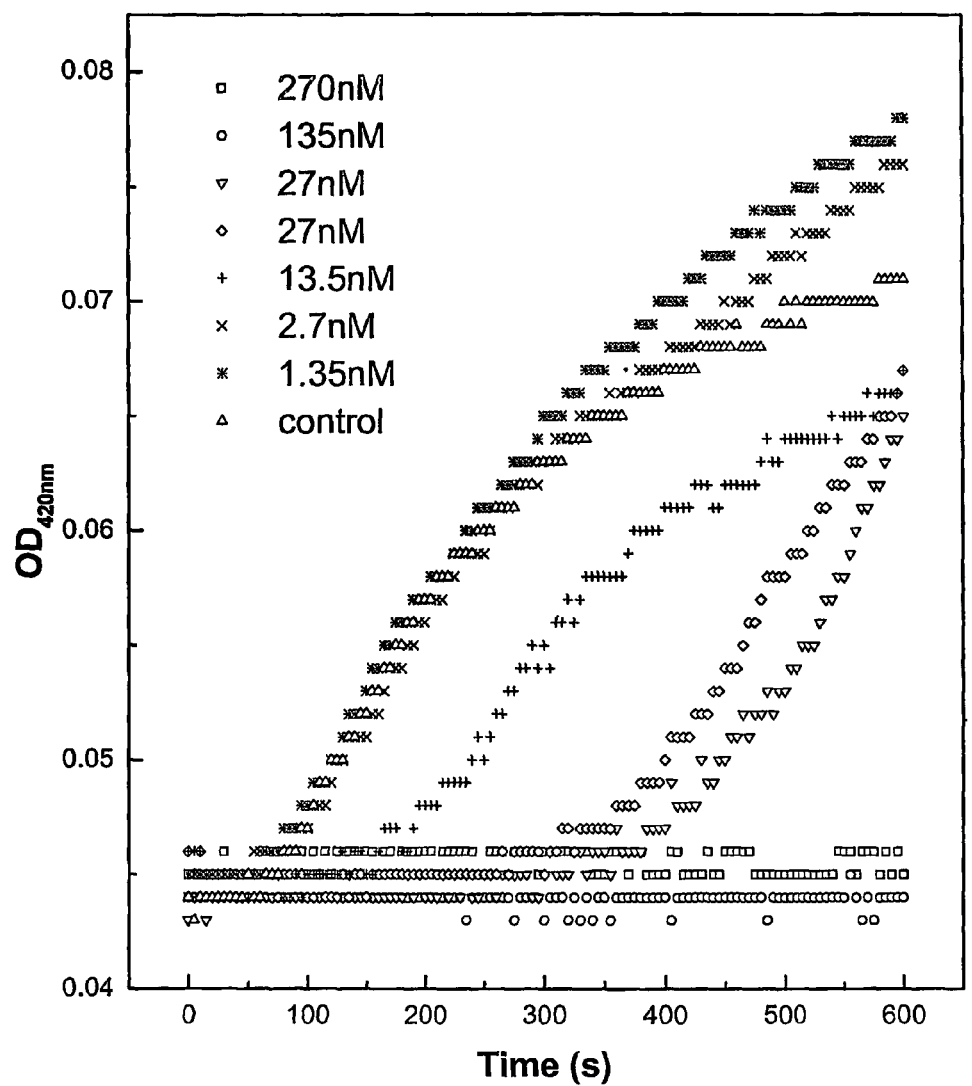
Figure 10. Progression curves for the clotting of human fibrinogen by human throm in the presence of varying concentrations of Bivalirudin.

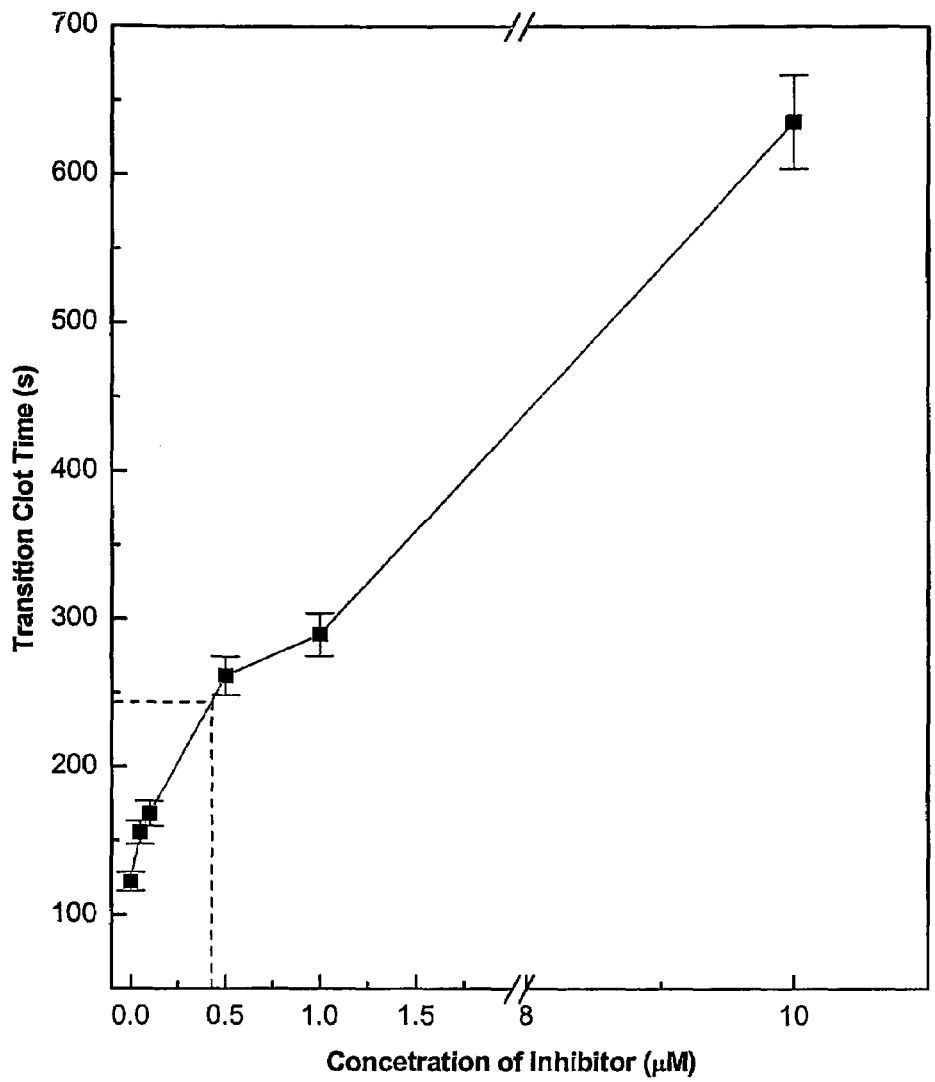
Figure 11. Inhibition of Thrombin by hirudin$^{54-65}$ anaylzed with the clotting assay. The concentrations of hirudin$^{54-65}$ required to double the clotting time or $DCT_{50}$ was determined as 447nM.

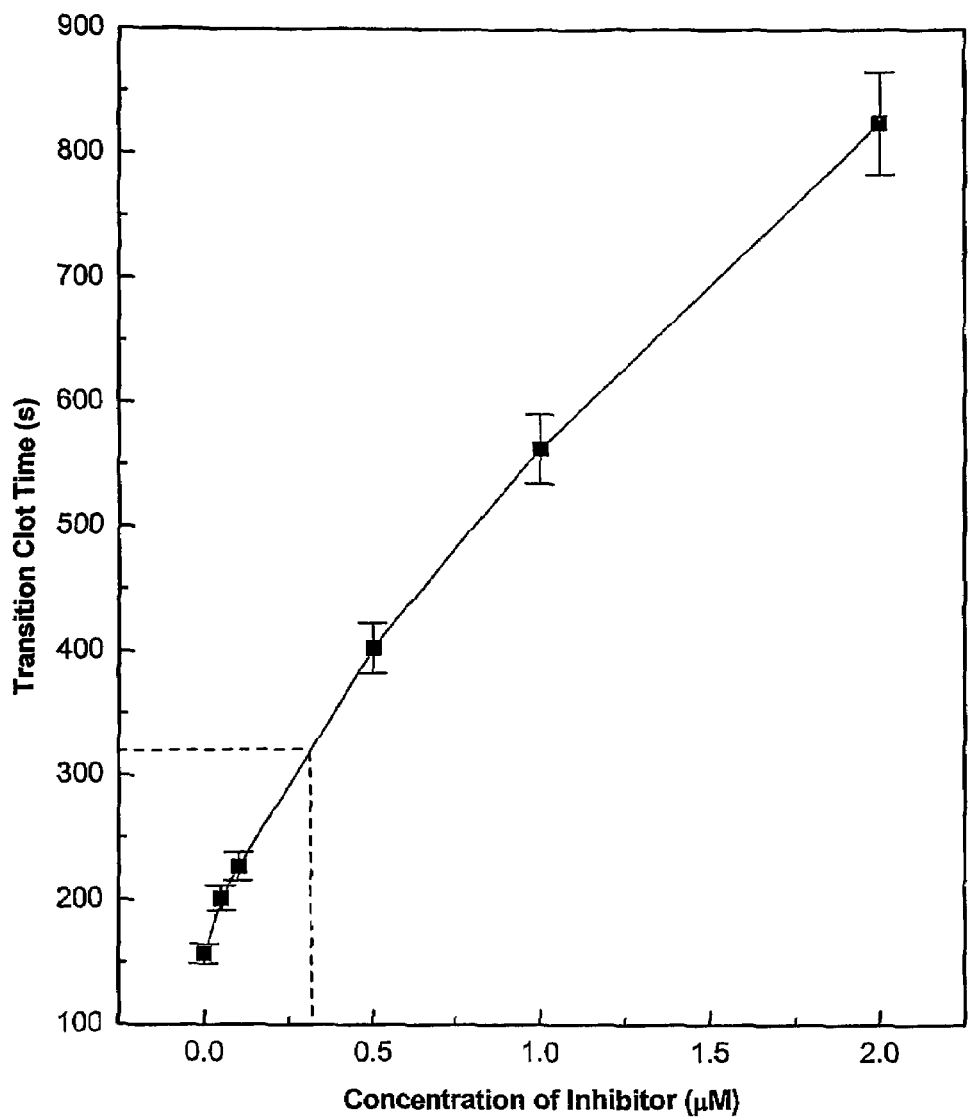
Figure 12. Inhibition of thrombin by FN22 analyzed with the clotting assay. The $DCT_{50}$ was determined as 289nM.

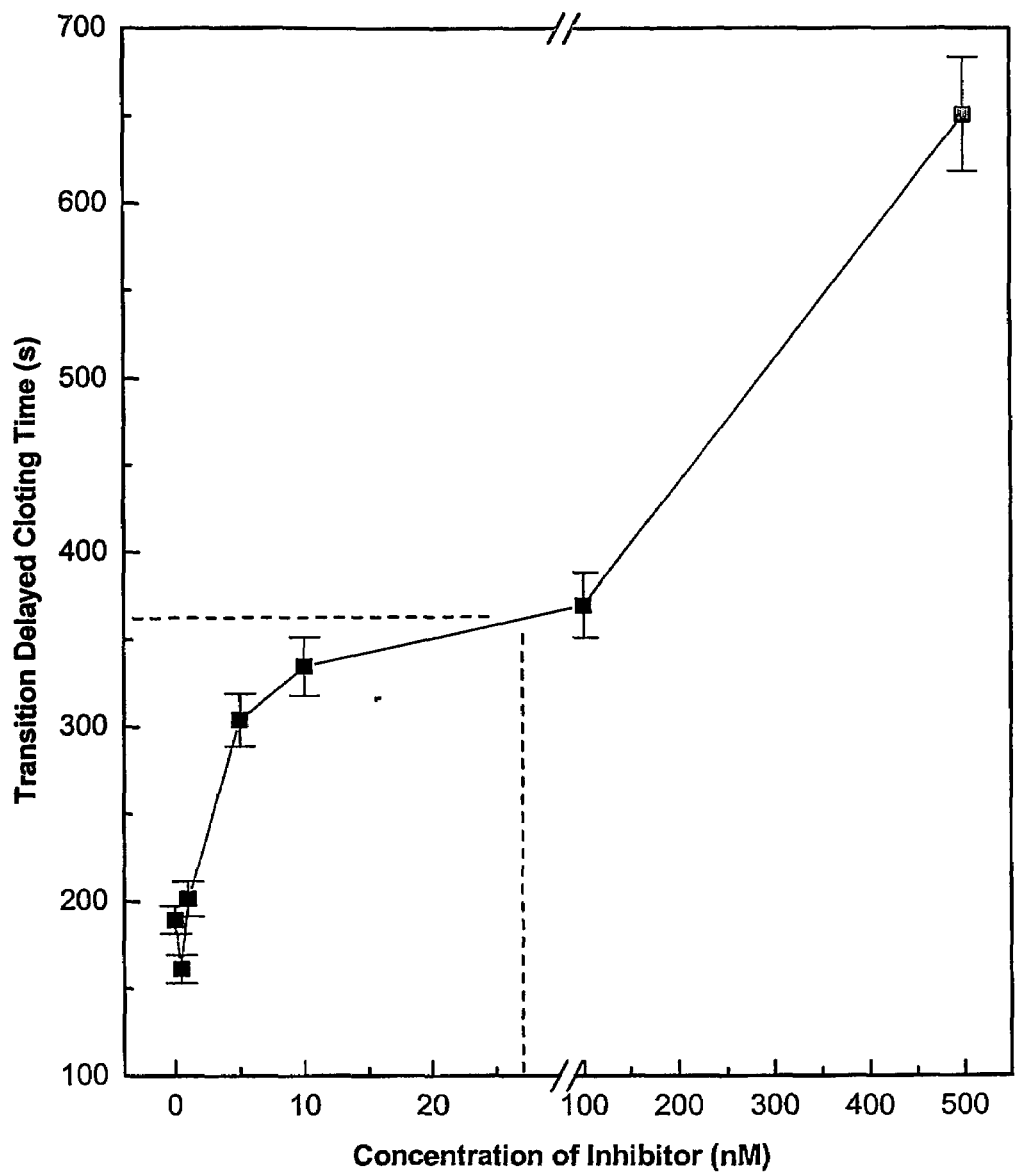
Figure 13. Inhibition of thrombin by FD22 analyzed with the clotting assay. The $DCT_{50}$ was determined as 28.2nM.

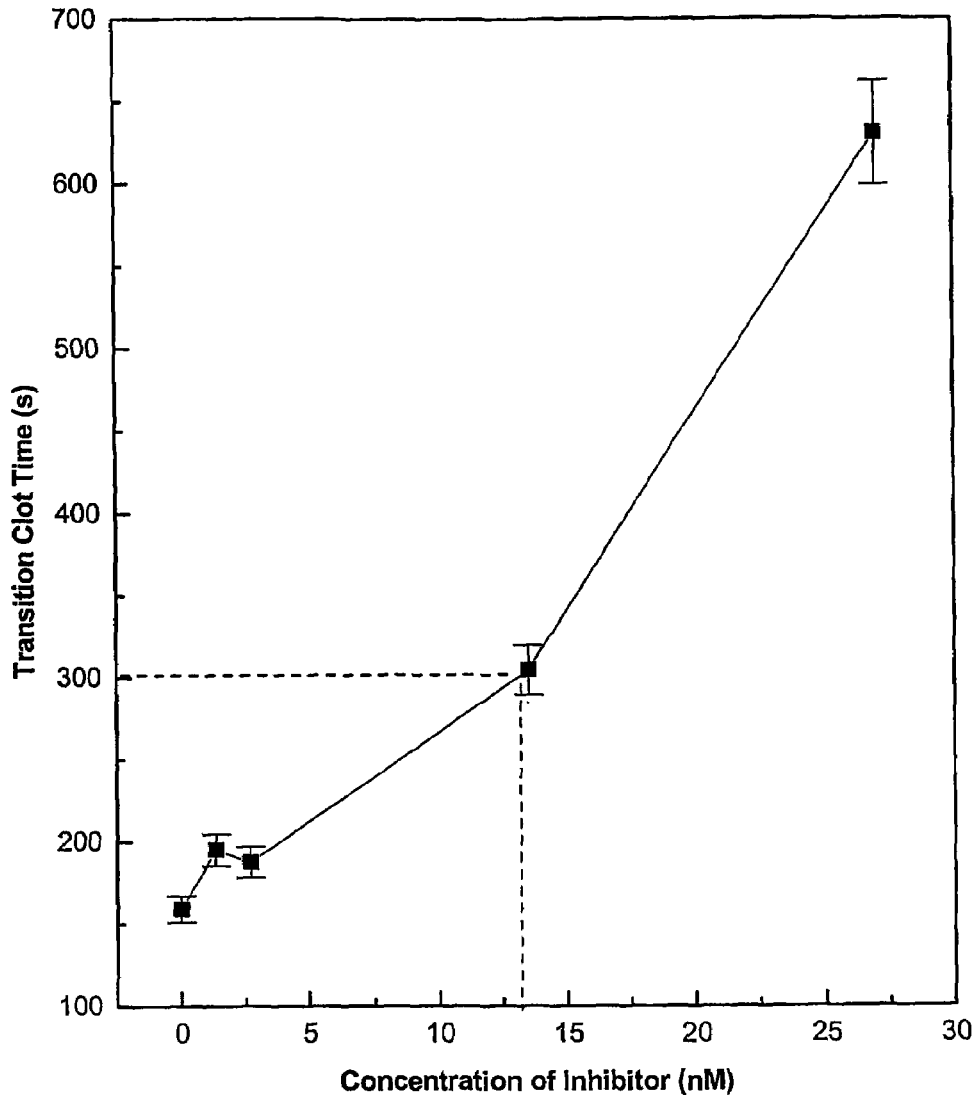
Figure 14. Inhibition of thrombin by Bivalirudin anaylzed with the clottin assay. The $DCT_{50}$ was determined as 12.4nM.

A

Thrombin binding site | Active site | Linker | Exosite I

P53      dF₄₅P R P Q S₅₀ H N D G D₅₅ F E E I P₆₀ E E Y L Q₆₅
FN22     F N₄₅ P R P Q S₅₀ H N D G D₅₅ F E E I P₆₀ E E Y L Q₆₅
FD22     F D₄₅ P R P Q S₅₀ H N D G D₅₅ F E E I P₆₀ E E Y L Q₆₅
Hirulog   dF₄₅P R P G G₅₀ G G N G D₅₅ F E E I P₆₀ E E Y L Cleavage site   P₄ P₃ P₂ P₁ P₁' P₂' P₃'

B

5'-GAATTCATGTTTAACCCGCGCCCTCAAAGTCATAACGACGGTGATTTT
                                             TTGCTGCCACTAAAA

GAG-3'                                 SEQ ID NO :118
CTCCTTTAAGGACTTCTCATAAATGTTATTCCTAGG    SEQ ID NO :119

Fig. 15

SEQUENCE LISTING

<160> NUMBER OF SEQ ID NOS: 125

<210> SEQ ID NO 1
<211> LENGTH: 4
<212> TYPE: PRT
<213> ORGANISM: Artificial Sequence
<220> FEATURE:
<223> OTHER INFORMATION: Segment of thrombin inhibitor

<400> SEQUENCE: 1

Leu Asp Pro Arg
1

<210> SEQ ID NO 2
<211> LENGTH: 10
<212> TYPE: PRT
<213> ORGANISM: Artificial Sequence
<220> FEATURE:
<223> OTHER INFORMATION: Segment of thrombin inhibitor

<400> SEQUENCE: 2

Asp Phe Leu Ala Gln Gly Gly Gly Val Arg
 1               5                   10

<210> SEQ ID NO 3
<211> LENGTH: 4
<212> TYPE: PRT
<213> ORGANISM: Artificial Sequence
<220> FEATURE:
<223> OTHER INFORMATION: Segment of thrombin inhibitor

<400> SEQUENCE: 3

Phe Asn Pro Arg
 1

<210> SEQ ID NO 4
<211> LENGTH: 4
<212> TYPE: PRT
<213> ORGANISM: Artificial Sequence
<220> FEATURE:
<223> OTHER INFORMATION: Segment of thrombin inhibitor

<400> SEQUENCE: 4

Phe Asp Pro Arg
 1

<210> SEQ ID NO 5
<211> LENGTH: 4
<212> TYPE: PRT
<213> ORGANISM: Artificial Sequence
<220> FEATURE:
<223> OTHER INFORMATION: Segment of thrombin inhibitor

<400> SEQUENCE: 5

Trp Asp Pro Arg
 1

<210> SEQ ID NO 6
<211> LENGTH: 45
<212> TYPE: DNA
<213> ORGANISM: Artificial Sequence
<220> FEATURE:
<223> OTHER INFORMATION: Segment of thrombin inhibitor

<400> SEQUENCE: 6
catgaccaca gtgcacagca ccaccaccat caccatggct ctggc                45

<210> SEQ ID NO 7
<211> LENGTH: 66
<212> TYPE: DNA
<213> ORGANISM: Artificial Sequence
<220> FEATURE:
<223> OTHER INFORMATION: Segment of thrombin inhibitor
<220> FEATURE:
<221> NAME/KEY: misc_feature
<222> LOCATION: (1)...(66)
<223> OTHER INFORMATION: n = A,T,C or G

<400> SEQUENCE: 7
ttcctcaaaa tcaccgtcgt tatgmnnttg agggcgcggm nnmnnagagc cagagccatg       60

```
gtgatg                                                               66
```

<210> SEQ ID NO 8
<211> LENGTH: 48
<212> TYPE: DNA
<213> ORGANISM: Artificial Sequence
<220> FEATURE:
<223> OTHER INFORMATION: Segment of thrombin inhibitor

<400> SEQUENCE: 8

```
aacgacggtg attttgagga aattcctgaa gagtatttac aaggtggt                 48
```

<210> SEQ ID NO 9
<211> LENGTH: 39
<212> TYPE: DNA
<213> ORGANISM: Artificial Sequence
<220> FEATURE:
<223> OTHER INFORMATION: Segment of thrombin inhibitor

<400> SEQUENCE: 9

```
cgattctgcg gccgcagaag aaccaccttg taaatactc                           39
```

<210> SEQ ID NO 10
<211> LENGTH: 12
<212> TYPE: PRT
<213> ORGANISM: Artificial Sequence
<220> FEATURE:
<223> OTHER INFORMATION: Segment of thrombin inhibitor

<400> SEQUENCE: 10

Gly Asp Phe Glu Glu Ile Pro Glu Glu Tyr Leu Gln
 1               5                  10

<210> SEQ ID NO 11
<211> LENGTH: 5
<212> TYPE: PRT
<213> ORGANISM: Artificial Sequence
<220> FEATURE:
<223> OTHER INFORMATION: Segment of thrombin inhibitor

<400> SEQUENCE: 11

Phe Asn Pro Arg Pro
 1               5

<210> SEQ ID NO 12
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 12

Phe Asn Pro Arg Pro Gln Ser His Asn Asp Gly Asp Phe Glu Glu Ile
 1               5                  10                  15

Pro Glu Glu Tyr Leu Gln
            20

<210> SEQ ID NO 13
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 13

-continued

Phe Asp Pro Arg Pro Gln Ser His Asn Asp Gly Asp Phe Glu Glu Ile
1               5                   10                  15

Pro Glu Glu Tyr Leu Gln
            20

<210> SEQ ID NO 14
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 14

Phe Glu Pro Arg Pro Gln Ser His Asn Asp Gly Asp Phe Glu Glu Ile
1               5                   10                  15

Pro Glu Glu Tyr Leu Gln
            20

<210> SEQ ID NO 15
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 15

Phe His Pro Arg Pro Gln Ser His Asn Asp Gly Asp Phe Glu Glu Ile
1               5                   10                  15

Pro Glu Glu Tyr Leu Gln
            20

<210> SEQ ID NO 16
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 16

Phe Asp Pro Arg Pro Gln Asp His Asn Asp Gly Asp Phe Glu Glu Ile
1               5                   10                  15

Pro Glu Glu Tyr Leu Gln
            20

<210> SEQ ID NO 17
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 17

Phe Glu Pro Arg Pro Gln Asp His Asn Asp Gly Asp Phe Glu Glu Ile
1               5                   10                  15

Pro Glu Glu Tyr Leu Gln
            20

<210> SEQ ID NO 18
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 18

```
Phe Asp Pro Arg Pro Gln His His Asn Asp Gly Asp Phe Glu Glu Ile
1               5                   10                  15

Pro Glu Glu Tyr Leu Gln
            20

<210> SEQ ID NO 19
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 19

Phe Asp Pro Arg Pro Gln Lys His Asn Asp Gly Asp Phe Glu Glu Ile
1               5                   10                  15

Pro Glu Glu Tyr Leu Gln
            20

<210> SEQ ID NO 20
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 20

Phe Asp Pro Arg Pro Gln Arg His Asn Asp Gly Asp Phe Glu Glu Ile
1               5                   10                  15

Pro Glu Glu Tyr Leu Gln
            20

<210> SEQ ID NO 21
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 21

Trp Asp Pro Arg Pro Gln Arg His Asn Asp Gly Asp Phe Glu Glu Ile
1               5                   10                  15

Pro Glu Glu Tyr Leu Gln
            20

<210> SEQ ID NO 22
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 22

Trp Asp Pro Arg Pro Gln Arg His Asn Asp Gly Asp Phe Glu Pro Ile
1               5                   10                  15

Pro Glu Glu Tyr Leu Gln
            20

<210> SEQ ID NO 23
<211> LENGTH: 22
<212> TYPE: PRT
<213> ORGANISM: Artificial Sequence
<220> FEATURE:
<223> OTHER INFORMATION: Segment of thrombin inhibitor
```

```
<400> SEQUENCE: 23

Trp Asp Pro Arg Pro Gln Arg His Asn Asp Gly Asp Tyr Glu Pro Ile
1               5                   10                  15

Pro Glu Glu Tyr Leu Gln
            20

<210> SEQ ID NO 24
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 24

Trp Asp Pro Arg Pro Gln Ser Arg Asn Asp Gly Asp Phe Glu Pro Ile
1               5                   10                  15

Pro Glu Glu Tyr Leu Gln
            20

<210> SEQ ID NO 25
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 25

Trp Asp Pro Arg Pro Gln Ser Arg Asn Asp Gly Asp Tyr Glu Pro Ile
1               5                   10                  15

Pro Glu Glu Tyr Leu Gln
            20

<210> SEQ ID NO 26
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 26

Phe Asn Pro Arg Pro Gln Ile His Asn Asp Gly Asp Phe Glu Glu Ile
1               5                   10                  15

Pro Glu Glu Tyr Leu Gln
            20

<210> SEQ ID NO 27
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 27

Ile Gln Pro Arg Pro Gln Ile His Asn Asp Gly Asp Phe Glu Glu Ile
1               5                   10                  15

Pro Glu Glu Tyr Leu Gln
            20

<210> SEQ ID NO 28
<211> LENGTH: 24
<212> TYPE: PRT
<213> ORGANISM: Artificial Sequence
<220> FEATURE:
<223> OTHER INFORMATION: Segment of thrombin inhibitor
```

<400> SEQUENCE: 28

Gly Ser Ala Val Pro Arg Pro Gln Ile His Asn Asp Gly Asp Phe Glu
1               5                   10                  15

Glu Ile Pro Glu Glu Tyr Leu Gln
            20

<210> SEQ ID NO 29
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 29

Phe Gln Pro Arg Pro Gln Met His Asn Asp Gly Asp Phe Glu Glu Ile
1               5                   10                  15

Pro Glu Glu Tyr Leu Gln
            20

<210> SEQ ID NO 30
<211> LENGTH: 24
<212> TYPE: PRT
<213> ORGANISM: Artificial Sequence
<220> FEATURE:
<223> OTHER INFORMATION: Segment of thrombin inhibitor

<400> SEQUENCE: 30

Gly Ser Ile Gln Pro Arg Pro Gln Ile His Asn Asp Gly Asp Phe Glu
1               5                   10                  15

Glu Ile Pro Glu Glu Tyr Leu Gln
            20

<210> SEQ ID NO 31
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 31

Trp Asp Pro Arg Pro Gln Leu His Asn Asp Gly Asp Phe Glu Pro Ile
1               5                   10                  15

Pro Glu Glu Tyr Leu Gln
            20

<210> SEQ ID NO 32
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 32

Leu Asp Pro Arg Pro Gln Ser His Asn Asp Gly Asp Phe Glu Glu Ile
1               5                   10                  15

Pro Glu Glu Tyr Leu Gln
            20

<210> SEQ ID NO 33
<211> LENGTH: 21
<212> TYPE: PRT
<213> ORGANISM: Artificial Sequence
<220> FEATURE:

<223> OTHER INFORMATION: Segment of thrombin inhibitor

<400> SEQUENCE: 33

Phe Asp Pro Arg Pro Gly Gly Gly Asn Gly Asp Phe Glu Glu Ile
1               5                   10                  15

Pro Glu Glu Tyr Leu
            20

<210> SEQ ID NO 34
<211> LENGTH: 36
<212> TYPE: PRT
<213> ORGANISM: Artificial Sequence
<220> FEATURE:
<223> OTHER INFORMATION: Segment of thrombin inhibitor
<220> FEATURE:
<221> NAME/KEY: VARIANT
<222> LOCATION: (1)...(36)
<223> OTHER INFORMATION: Xaa = Any Amino Acid

<400> SEQUENCE: 34

His His His His His His Gly Ser Gly Ser Xaa Xaa Pro Arg Pro Gln
1               5                   10                  15

Xaa His Asn Asp Gly Asp Phe Glu Glu Ile Pro Glu Glu Tyr Leu Gln
            20                  25                  30

Gly Gly Ser Ser
        35

<210> SEQ ID NO 35
<211> LENGTH: 7
<212> TYPE: PRT
<213> ORGANISM: Artificial Sequence
<220> FEATURE:
<223> OTHER INFORMATION: Segment of thrombin inhibitor

<400> SEQUENCE: 35

Phe Gln Pro Arg Pro Gln Met
1               5

<210> SEQ ID NO 36
<211> LENGTH: 9
<212> TYPE: PRT
<213> ORGANISM: Artificial Sequence
<220> FEATURE:
<223> OTHER INFORMATION: Segment of thrombin inhibitor

<400> SEQUENCE: 36

Gly Ser Ile Gln Pro Arg Pro Gln Ile
1               5

<210> SEQ ID NO 37
<211> LENGTH: 4
<212> TYPE: PRT
<213> ORGANISM: Artificial Sequence
<220> FEATURE:
<223> OTHER INFORMATION: Segment of thrombin inhibitor

<400> SEQUENCE: 37

Val Asp Pro Arg
1

<210> SEQ ID NO 38
<211> LENGTH: 4
<212> TYPE: PRT
<213> ORGANISM: Artificial Sequence
<220> FEATURE:
<223> OTHER INFORMATION: Segment of thrombin inhibitor

```
<400> SEQUENCE: 38

Ile Ser Pro Arg
 1

<210> SEQ ID NO 39
<211> LENGTH: 4
<212> TYPE: PRT
<213> ORGANISM: Artificial Sequence
<220> FEATURE:
<223> OTHER INFORMATION: Segment of thrombin inhibitor
<220> FEATURE:
<221> NAME/KEY: VARIANT
<222> LOCATION: (1)...(4)
<223> OTHER INFORMATION: Xaa = Any Amino Acid

<400> SEQUENCE: 39

Phe Xaa Pro Arg
 1

<210> SEQ ID NO 40
<211> LENGTH: 4
<212> TYPE: PRT
<213> ORGANISM: Artificial Sequence
<220> FEATURE:
<223> OTHER INFORMATION: Segment of thrombin inhibitor

<400> SEQUENCE: 40

Leu Val Pro Arg
 1

<210> SEQ ID NO 41
<211> LENGTH: 4
<212> TYPE: PRT
<213> ORGANISM: Artificial Sequence
<220> FEATURE:
<223> OTHER INFORMATION: Segment of thrombin inhibitor

<400> SEQUENCE: 41

Phe Gln Pro Arg
 1

<210> SEQ ID NO 42
<211> LENGTH: 4
<212> TYPE: PRT
<213> ORGANISM: Artificial Sequence
<220> FEATURE:
<223> OTHER INFORMATION: Segment of thrombin inhibitor

<400> SEQUENCE: 42

Phe Glu Pro Arg
 1

<210> SEQ ID NO 43
<211> LENGTH: 4
<212> TYPE: PRT
<213> ORGANISM: Artificial Sequence
<220> FEATURE:
<223> OTHER INFORMATION: Segment of thrombin inhibitor

<400> SEQUENCE: 43

Phe His Pro Arg
 1

<210> SEQ ID NO 44
<211> LENGTH: 4
<212> TYPE: PRT
```

```
<213> ORGANISM: Artificial Sequence
<220> FEATURE:
<223> OTHER INFORMATION: Segment of thrombin inhibitor

<400> SEQUENCE: 44

Tyr Asn Pro Arg
 1

<210> SEQ ID NO 45
<211> LENGTH: 4
<212> TYPE: PRT
<213> ORGANISM: Artificial Sequence
<220> FEATURE:
<223> OTHER INFORMATION: Segment of thrombin inhibitor

<400> SEQUENCE: 45

Tyr Ser Pro Arg
 1

<210> SEQ ID NO 46
<211> LENGTH: 4
<212> TYPE: PRT
<213> ORGANISM: Artificial Sequence
<220> FEATURE:
<223> OTHER INFORMATION: Segment of thrombin inhibitor

<400> SEQUENCE: 46

Ile Gln Pro Arg
 1

<210> SEQ ID NO 47
<211> LENGTH: 6
<212> TYPE: PRT
<213> ORGANISM: Artificial Sequence
<220> FEATURE:
<223> OTHER INFORMATION: Segment of thrombin inhibitor

<400> SEQUENCE: 47

Gly Ser Ile Gln Pro Arg
 1               5

<210> SEQ ID NO 48
<211> LENGTH: 4
<212> TYPE: PRT
<213> ORGANISM: Artificial Sequence
<220> FEATURE:
<223> OTHER INFORMATION: Segment of thrombin inhibitor

<400> SEQUENCE: 48

Ile Asn Pro Arg
 1

<210> SEQ ID NO 49
<211> LENGTH: 4
<212> TYPE: PRT
<213> ORGANISM: Artificial Sequence
<220> FEATURE:
<223> OTHER INFORMATION: Segment of thrombin inhibitor

<400> SEQUENCE: 49

Val Gln Pro Arg
 1

<210> SEQ ID NO 50
<211> LENGTH: 4
<212> TYPE: PRT
<213> ORGANISM: Artificial Sequence
```

```
<220> FEATURE:
<223> OTHER INFORMATION: Segment of thrombin inhibitor

<400> SEQUENCE: 50

Ala Val Pro Arg
 1

<210> SEQ ID NO 51
<211> LENGTH: 6
<212> TYPE: PRT
<213> ORGANISM: Artificial Sequence
<220> FEATURE:
<223> OTHER INFORMATION: Segment of thrombin inhibitor

<400> SEQUENCE: 51

Gly Ser Ala Val Pro Arg
 1               5

<210> SEQ ID NO 52
<211> LENGTH: 4
<212> TYPE: PRT
<213> ORGANISM: Artificial Sequence
<220> FEATURE:
<223> OTHER INFORMATION: Segment of thrombin inhibitor

<400> SEQUENCE: 52

Ala Leu Pro Arg
 1

<210> SEQ ID NO 53
<211> LENGTH: 4
<212> TYPE: PRT
<213> ORGANISM: Artificial Sequence
<220> FEATURE:
<223> OTHER INFORMATION: Segment of thrombin inhibitor

<400> SEQUENCE: 53

Ala Ile Pro Arg
 1

<210> SEQ ID NO 54
<211> LENGTH: 7
<212> TYPE: PRT
<213> ORGANISM: Artificial Sequence
<220> FEATURE:
<223> OTHER INFORMATION: Segment of thrombin inhibitor

<400> SEQUENCE: 54

Pro Gln Ser His Asn Asp Gly
 1               5

<210> SEQ ID NO 55
<211> LENGTH: 7
<212> TYPE: PRT
<213> ORGANISM: Artificial Sequence
<220> FEATURE:
<223> OTHER INFORMATION: Segment of thrombin inhibitor

<400> SEQUENCE: 55

Pro Gln Arg His Asn Asp Gly
 1               5

<210> SEQ ID NO 56
<211> LENGTH: 7
<212> TYPE: PRT
<213> ORGANISM: Artificial Sequence
<220> FEATURE:
```

<223> OTHER INFORMATION: Segment of thrombin inhibitor

<400> SEQUENCE: 56

Pro Gln Arg Pro Asn Asp Gly
1               5

<210> SEQ ID NO 57
<211> LENGTH: 7
<212> TYPE: PRT
<213> ORGANISM: Artificial Sequence
<220> FEATURE:
<223> OTHER INFORMATION: Segment of thrombin inhibitor

<400> SEQUENCE: 57

Pro Gln Ser Arg Asn Asp Gly
1               5

<210> SEQ ID NO 58
<211> LENGTH: 7
<212> TYPE: PRT
<213> ORGANISM: Artificial Sequence
<220> FEATURE:
<223> OTHER INFORMATION: Segment of thrombin inhibitor

<400> SEQUENCE: 58

Pro Gln Ile His Asn Asp Gly
1               5

<210> SEQ ID NO 59
<211> LENGTH: 7
<212> TYPE: PRT
<213> ORGANISM: Artificial Sequence
<220> FEATURE:
<223> OTHER INFORMATION: Segment of thrombin inhibitor

<400> SEQUENCE: 59

Pro Gln Leu His Asn Asp Gly
1               5

<210> SEQ ID NO 60
<211> LENGTH: 7
<212> TYPE: PRT
<213> ORGANISM: Artificial Sequence
<220> FEATURE:
<223> OTHER INFORMATION: Segment of thrombin inhibitor

<400> SEQUENCE: 60

Pro Gln Met His Asn Asp Gly
1               5

<210> SEQ ID NO 61
<211> LENGTH: 7
<212> TYPE: PRT
<213> ORGANISM: Artificial Sequence
<220> FEATURE:
<223> OTHER INFORMATION: Segment of thrombin inhibitor

<400> SEQUENCE: 61

Pro Gln Asp His Asn Asp Gly
1               5

<210> SEQ ID NO 62
<211> LENGTH: 7
<212> TYPE: PRT
<213> ORGANISM: Artificial Sequence
<220> FEATURE:
<223> OTHER INFORMATION: Segment of thrombin inhibitor

```
<400> SEQUENCE: 62

Pro Gln His His Asn Asp Gly
1               5

<210> SEQ ID NO 63
<211> LENGTH: 7
<212> TYPE: PRT
<213> ORGANISM: Artificial Sequence
<220> FEATURE:
<223> OTHER INFORMATION: Segment of thrombin inhibitor

<400> SEQUENCE: 63

Pro Gln Lys His Asn Asp Gly
1               5

<210> SEQ ID NO 64
<211> LENGTH: 11
<212> TYPE: PRT
<213> ORGANISM: Artificial Sequence
<220> FEATURE:
<223> OTHER INFORMATION: Segment of thrombin inhibitor

<400> SEQUENCE: 64

Asp Phe Glu Glu Ile Pro Glu Glu Tyr Leu Gln
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Segment of thrombin inhibitor

<400> SEQUENCE: 65

Asp Phe Glu Pro Ile Pro Glu Glu Tyr Leu Gln
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Segment of thrombin inhibitor

<400> SEQUENCE: 66

Asp Tyr Glu Pro Ile Pro Glu Glu Tyr Leu Gln
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Segment of thrombin inhibitor

<400> SEQUENCE: 67

Asp Phe Glu Pro Ile Pro Glu Glu Tyr Leu
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Segment of thrombin inhibitor
```

```
<400> SEQUENCE: 68

Asp Tyr Glu Pro Ile Pro Glu Glu Tyr Leu
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Segment of thrombin inhibitor
<220> FEATURE:
<221> NAME/KEY: VARIANT
<222> LOCATION: (1)...(7)
<223> OTHER INFORMATION: Xaa = Any Amino Acid

<400> SEQUENCE: 69

Pro Gln Xaa His Asn Asp Gly
1               5

<210> SEQ ID NO 70
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 70

Thr Phe Pro Arg Pro Gln Pro His Asn Asp Gly Asp Phe Glu Glu Ile
1               5                   10                  15

Pro Glu Glu Tyr Leu Gln
            20

<210> SEQ ID NO 71
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 71

Asn Val Pro Arg Pro Gln Ala His Asn Asp Gly Asp Phe Glu Glu Ile
1               5                   10                  15

Pro Glu Glu Tyr Leu Gln
            20

<210> SEQ ID NO 72
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 72

Tyr Asn Pro Arg Pro Gln Ile His Asn Asp Gly Asp Phe Glu Glu Ile
1               5                   10                  15

Pro Glu Glu Tyr Leu Gln
            20

<210> SEQ ID NO 73
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 73
```

His Tyr Pro Arg Pro Gln Ile His Asn Asp Gly Asp Phe Glu Glu Ile
1               5                   10                  15

Pro Glu Glu Tyr Leu Gln
            20

<210> SEQ ID NO 74
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 74

His Tyr Pro Arg Pro Gln Thr His Asn Asp Gly Asp Phe Glu Glu Ile
1               5                   10                  15

Pro Glu Glu Tyr Leu Gln
            20

<210> SEQ ID NO 75
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 75

His Ala Pro Arg Pro Gln Ser His Asn Asp Gly Asp Phe Glu Glu Ile
1               5                   10                  15

Pro Glu Glu Tyr Leu Gln
            20

<210> SEQ ID NO 76
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 76

Ile Leu Pro Arg Pro Gln Met His Asn Asp Gly Asp Phe Glu Glu Ile
1               5                   10                  15

Pro Glu Glu Tyr Leu Gln
            20

<210> SEQ ID NO 77
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 77

Leu Thr Pro Arg Pro Gln Ile His Asn Asp Gly Asp Phe Glu Glu Ile
1               5                   10                  15

Pro Glu Glu Tyr Leu Gln
            20

<210> SEQ ID NO 78
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 78

Asn Thr Pro Arg Pro Gln Phe His Asn Asp Gly Asp Phe Glu Glu Ile
 1               5                  10                  15

Pro Glu Glu Tyr Leu Gln
            20

<210> SEQ ID NO 79
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 79

Gln Ser Pro Arg Pro Gln Leu His Asn Asp Gly Asp Phe Glu Glu Ile
 1               5                  10                  15

Pro Glu Glu Tyr Leu Gln
            20

<210> SEQ ID NO 80
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 80

His Val Pro Arg Pro Gln Leu His Asn Asp Gly Asp Phe Glu Glu Ile
 1               5                  10                  15

Pro Glu Glu Tyr Leu Gln
            20

<210> SEQ ID NO 81
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 81

His Thr Pro Arg Pro Gln Gln His Asn Asp Gly Asp Phe Glu Glu Ile
 1               5                  10                  15

Pro Glu Glu Tyr Leu Gln
            20

<210> SEQ ID NO 82
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 82

Leu Met Pro Arg Pro Gln Ser His Asn Asp Gly Asp Phe Glu Glu Ile
 1               5                  10                  15

Pro Glu Glu Tyr Leu Gln
            20

<210> SEQ ID NO 83
<211> LENGTH: 22
<212> TYPE: PRT
<213> ORGANISM: Artificial Sequence
<220> FEATURE:
<223> OTHER INFORMATION: Segment of thrombin inhibitor

```
<400> SEQUENCE: 83

Ile Asn Pro Arg Pro Gln Met His Asn Asp Gly Asp Phe Glu Glu Ile
1               5                   10                  15

Pro Glu Glu Tyr Leu Gln
            20

<210> SEQ ID NO 84
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 84

Val Thr Pro Arg Pro Gln Pro His Asn Asp Gly Asp Phe Glu Glu Ile
1               5                   10                  15

Pro Glu Glu Tyr Leu Gln
            20

<210> SEQ ID NO 85
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 85

Thr Asp Pro Arg Pro Gln Ile His Asn Asp Gly Asp Phe Glu Glu Ile
1               5                   10                  15

Pro Glu Glu Tyr Leu Gln
            20

<210> SEQ ID NO 86
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 86

Pro Glu Pro Arg Pro Gln Leu His Asn Asp Gly Asp Phe Glu Glu Ile
1               5                   10                  15

Pro Glu Glu Tyr Leu Gln
            20

<210> SEQ ID NO 87
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 87

Gly Asn Pro Arg Pro Gln Tyr His Asn Asp Gly Asp Phe Glu Glu Ile
1               5                   10                  15

Pro Glu Glu Tyr Leu Gln
            20

<210> SEQ ID NO 88
<211> LENGTH: 22
<212> TYPE: PRT
<213> ORGANISM: Artificial Sequence
<220> FEATURE:
```

<223> OTHER INFORMATION: Segment of thrombin inhibitor

<400> SEQUENCE: 88

Tyr Ser Pro Arg Pro Gln Ile His Asn Asp Gly Asp Phe Glu Glu Ile
1               5                   10                  15

Pro Glu Glu Tyr Leu Gln
            20

<210> SEQ ID NO 89
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 89

Tyr Asn Pro Arg Pro Gln His His Asn Asp Gly Asp Phe Glu Glu Ile
1               5                   10                  15

Pro Glu Glu Tyr Leu Gln
            20

<210> SEQ ID NO 90
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 90

Ile Gln Pro Arg Pro Gln Met His Asn Asp Gly Asp Phe Glu Glu Ile
1               5                   10                  15

Pro Glu Glu Tyr Leu Gln
            20

<210> SEQ ID NO 91
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 91

Ile Met Pro Arg Pro Gln Met His Asn Asp Gly Asp Phe Glu Glu Ile
1               5                   10                  15

Pro Glu Glu Tyr Leu Gln
            20

<210> SEQ ID NO 92
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 92

Ile Ile Pro Arg Pro Gln Met His Asn Asp Gly Asp Phe Glu Glu Ile
1               5                   10                  15

Pro Glu Glu Tyr Leu Gln
            20

<210> SEQ ID NO 93
<211> LENGTH: 22
<212> TYPE: PRT
<213> ORGANISM: Artificial Sequence

```
<220> FEATURE:
<223> OTHER INFORMATION: Segment of thrombin inhibitor

<400> SEQUENCE: 93

Ile His Pro Arg Pro Gln Met His Asn Asp Gly Asp Phe Glu Glu Ile
 1               5                  10                  15

Pro Glu Glu Tyr Leu Gln
            20

<210> SEQ ID NO 94
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 94

Val Gln Pro Arg Pro Gln Gln His Asn Asp Gly Asp Phe Glu Glu Ile
 1               5                  10                  15

Pro Glu Glu Tyr Leu Gln
            20

<210> SEQ ID NO 95
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 95

Val Met Pro Arg Pro Gln Gln His Asn Asp Gly Asp Phe Glu Glu Ile
 1               5                  10                  15

Pro Glu Glu Tyr Leu Gln
            20

<210> SEQ ID NO 96
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 96

Val Gln Pro Arg Pro Gln Pro His Asn Asp Gly Asp Phe Glu Glu Ile
 1               5                  10                  15

Pro Glu Glu Tyr Leu Gln
            20

<210> SEQ ID NO 97
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 97

Leu His Pro Arg Pro Gln Leu His Asn Asp Gly Asp Phe Glu Glu Ile
 1               5                  10                  15

Pro Glu Glu Tyr Leu Gln
            20

<210> SEQ ID NO 98
<211> LENGTH: 22
<212> TYPE: PRT
```

```
<213> ORGANISM: Artificial Sequence
<220> FEATURE:
<223> OTHER INFORMATION: Segment of thrombin inhibitor

<400> SEQUENCE: 98

Leu Ile Pro Arg Pro Gln Met His Asn Asp Gly Asp Phe Glu Glu Ile
 1               5                  10                  15

Pro Glu Glu Tyr Leu Gln
            20

<210> SEQ ID NO 99
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 99

Met Gln Pro Arg Pro Gln Met His Asn Asp Gly Asp Phe Glu Glu Ile
 1               5                  10                  15

Pro Glu Glu Tyr Leu Gln
            20

<210> SEQ ID NO 100
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 100

Met Met Pro Arg Pro Gln Met His Asn Asp Gly Asp Phe Glu Glu Ile
 1               5                  10                  15

Pro Glu Glu Tyr Leu Gln
            20

<210> SEQ ID NO 101
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 101

Ala Val Pro Arg Pro Gln Ile His Asn Asp Gly Asp Phe Glu Glu Ile
 1               5                  10                  15

Pro Glu Glu Tyr Leu Gln
            20

<210> SEQ ID NO 102
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 102

Ala Leu Pro Arg Pro Gln Ile His Asn Asp Gly Asp Phe Glu Glu Ile
 1               5                  10                  15

Pro Glu Glu Tyr Leu Gln
            20

<210> SEQ ID NO 103
<211> LENGTH: 22
```

<212> TYPE: PRT
<213> ORGANISM: Artificial Sequence
<220> FEATURE:
<223> OTHER INFORMATION: Segment of thrombin inhibitor

<400> SEQUENCE: 103

Ala Ile Pro Arg Pro Gln Gln His Asn Asp Gly Asp Phe Glu Glu Ile
1               5                   10                  15

Pro Glu Glu Tyr Leu Gln
            20

<210> SEQ ID NO 104
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 104

Ala Ile Pro Arg Pro Gln Pro His Asn Asp Gly Asp Phe Glu Glu Ile
1               5                   10                  15

Pro Glu Glu Tyr Leu Gln
            20

<210> SEQ ID NO 105
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 105

Ala Met Pro Arg Pro Gln Ala His Asn Asp Gly Asp Phe Glu Glu Ile
1               5                   10                  15

Pro Glu Glu Tyr Leu Gln
            20

<210> SEQ ID NO 106
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 106

Ala Tyr Pro Arg Pro Gln Ala His Asn Asp Gly Asp Phe Glu Glu Ile
1               5                   10                  15

Pro Glu Glu Tyr Leu Gln
            20

<210> SEQ ID NO 107
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 107

Ala Gln Pro Arg Pro Gln Ile His Asn Asp Gly Asp Phe Glu Glu Ile
1               5                   10                  15

Pro Glu Glu Tyr Leu Gln
            20

<210> SEQ ID NO 108

<210> SEQ ID NO 108
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 108

Ala Thr Pro Arg Pro Gln Leu His Asn Asp Gly Asp Phe Glu Glu Ile
1               5                   10                  15

Pro Glu Glu Tyr Leu Gln
            20

<210> SEQ ID NO 109
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 109

Ala Thr Pro Arg Pro Gln Val His Asn Asp Gly Asp Phe Glu Glu Ile
1               5                   10                  15

Pro Glu Glu Tyr Leu Gln
            20

<210> SEQ ID NO 110
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 110

Pro Ile Pro Arg Pro Gln Ile His Asn Asp Gly Asp Phe Glu Glu Ile
1               5                   10                  15

Pro Glu Glu Tyr Leu Gln
            20

<210> SEQ ID NO 111
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 111

Pro His Pro Arg Pro Gln Ile His Asn Asp Gly Asp Phe Glu Glu Ile
1               5                   10                  15

Pro Glu Glu Tyr Leu Gln
            20

<210> SEQ ID NO 112
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 112

Pro Trp Pro Arg Pro Gln Leu His Asn Asp Gly Asp Phe Glu Glu Ile
1               5                   10                  15

Pro Glu Glu Tyr Leu Gln
            20

```
<210> SEQ ID NO 113
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 113

Pro Asn Pro Arg Pro Gln Val His Asn Asp Gly Asp Phe Glu Glu Ile
1               5                   10                  15

Pro Glu Glu Tyr Leu Gln
            20

<210> SEQ ID NO 114
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 114

Thr Ile Pro Arg Pro Gln Ile His Asn Asp Gly Asp Phe Glu Glu Ile
1               5                   10                  15

Pro Glu Glu Tyr Leu Gln
            20

<210> SEQ ID NO 115
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 115

Asn Asp Pro Arg Pro Gln Lys His Asn Asp Gly Asp Phe Glu Glu Ile
1               5                   10                  15

Pro Glu Glu Tyr Leu Gln
            20

<210> SEQ ID NO 116
<211> LENGTH: 22
<212> TYPE: PRT
<213> ORGANISM: Artificial Sequence
<220> FEATURE:
<223> OTHER INFORMATION: Segment of thrombin inhibitor

<400> SEQUENCE: 116

Asn Ser Pro Arg Pro Gln Leu His Asn Asp Gly Asp Phe Glu Glu Ile
1               5                   10                  15

Pro Glu Glu Tyr Leu Gln
            20

<210> SEQ ID NO 117
<211> LENGTH: 22
<212> TYPE: PRT
<213> ORGANISM: Artificial Sequence
<220> FEATURE:
<223> OTHER INFORMATION: Segment of thrombin inhibitor
<220> FEATURE:
<221> NAME/KEY: VARIANT
<222> LOCATION: (1)...(22)
<223> OTHER INFORMATION: Xaa = Any Amino Acid

<400> SEQUENCE: 117

Xaa Xaa Pro Arg Pro Xaa Xaa Xaa Xaa Xaa Xaa Asp Phe Glu Glu Ile
1               5                   10                  15
```

Pro Glu Glu Tyr Leu Gln
            20

<210> SEQ ID NO 118
<211> LENGTH: 51
<212> TYPE: DNA
<213> ORGANISM: Artificial Sequence
<220> FEATURE:
<223> OTHER INFORMATION: Segment of thrombin inhibitor

<400> SEQUENCE: 118
gaattcatgt taacccgcg ccctcaaagt cataacgacg gtgatttga g       51

<210> SEQ ID NO 119
<211> LENGTH: 51
<212> TYPE: DNA
<213> ORGANISM: Artificial Sequence
<220> FEATURE:
<223> OTHER INFORMATION: Segment of thrombin inhibitor

<400> SEQUENCE: 119
ggatccttat tgtaaatact cttcaggaat tcctcaaaa tcaccgtcgt t       51

<210> SEQ ID NO 120
<211> LENGTH: 42
<212> TYPE: PRT
<213> ORGANISM: Artificial Sequence
<220> FEATURE:
<223> OTHER INFORMATION: Segment of thrombin inhibitor
<220> FEATURE:
<221> NAME/KEY: VARIANT
<222> LOCATION: (1)...(42)
<223> OTHER INFORMATION: Xaa = Any Amino Acid

<400> SEQUENCE: 120

Ser Ala Gln His His His His His His Gly Ser Gly Ser Xaa Xaa Pro
 1               5                  10                  15

Arg Pro Gln Xaa His Asn Asp Gly Asp Phe Glu Glu Ile Pro Glu Glu
            20                  25                  30

Tyr Leu Gln Gly Gly Ser Ser Ala Ala Ala
        35                  40

<210> SEQ ID NO 121
<211> LENGTH: 4
<212> TYPE: PRT
<213> ORGANISM: Artificial Sequence
<220> FEATURE:
<223> OTHER INFORMATION: Segment of thrombin inhibitor
<220> FEATURE:
<221> NAME/KEY: VARIANT
<222> LOCATION: (1)...(4)
<223> OTHER INFORMATION: Xaa = Any Amino Acid

<400> SEQUENCE: 121

Trp Xaa Pro Arg
 1

<210> SEQ ID NO 122
<211> LENGTH: 5
<212> TYPE: PRT
<213> ORGANISM: Artificial Sequence
<220> FEATURE:
<223> OTHER INFORMATION: Segment of thrombin inhibitor

<400> SEQUENCE: 122

Phe Asp Pro Arg Pro

```
                                     -continued
1               5

<210> SEQ ID NO 123
<211> LENGTH: 6
<212> TYPE: PRT
<213> ORGANISM: Artificial Sequence
<220> FEATURE:
<223> OTHER INFORMATION: Segment of thrombin inhibitor

<400> SEQUENCE: 123

Gln Ser His Asn Asp Gly
1               5

<210> SEQ ID NO 124
<211> LENGTH: 6
<212> TYPE: PRT
<213> ORGANISM: Artificial Sequence
<220> FEATURE:
<223> OTHER INFORMATION: Segment of thrombin inhibitor

<400> SEQUENCE: 124

Gly Gly Gly Gly Asn Gly
1               5

<210> SEQ ID NO 125
<211> LENGTH: 10
<212> TYPE: PRT
<213> ORGANISM: Artificial Sequence
<220> FEATURE:
<223> OTHER INFORMATION: Segment of thrombin inhibitor

<400> SEQUENCE: 125

Asp Phe Glu Glu Ile Pro Glu Glu Tyr Leu
1               5                   10
```

PEPTIDE INHIBITORS OF THROMBIN AS POTENT ANTICOAGULANTS

BACKGROUND OF THE INVENTION (a) Field of the Invention

The invention relates to peptide inhibitors of thrombin that can be used as potent anticoagulants, and that are composed of natural amino acids or that can be made by recombinant techniques.

(b) Description of Prior Art

A wide range of medical conditions including atherosclerosis, infections and cancer can trigger thrombotic complications, leading to heart attack, stroke, deep-vein thrombosis, or pulmonary embolism (Libby, P. (2002) *Nature* 420, 868-874; Levi, M., Keller, T. T., van Gorp, E., and ten Cate, H. (2003) *Cardiovasc. Res.* 60, 26-39; Opal, S. M. and Esmon, C. T. (2003) *Crit Care* 7, 23-38; Loynes, J. and Zacharski, L. (2003) *Expert. Opin. Ther. Targets.* 7, 399-404; and Schultz, M. J., Levi, M., and van der, P. T. (2003) *Curr. Drug Targets.* 4, 315-321). As such, thrombosis, or the aberrant formation of a blood clot, has been the single largest cause of human disability and death in the world. In many situations, it is the occlusive blood clot that is life-threatening for patients with atherosclerosis and related cardiovascular diseases (Libby, P. (2002) *Sci. Am.* 286, 46-55; Libby, P. (2002) *Nature* 420, 868-874; and Virmani, R., Burke, A. P., and Farb, A. (2001) *Cardiovasc. Pathol.* 10, 211-218) or on long-term anti-HIV treatments (Madamanchi, N. R., Patterson, C., and Runge, M. S. (2002) *Arterioscler. Thromb. Vasc. Biol.* 22, 1758-1760; and Zhong, D. S., Lu, X. H., Conklin, B. S., Lin, P. H., Lumsden, A. B., Yao, Q., and Chen, C. (2002) *Arterioscler. Thromb. Vasc. Biol.* 22, 1560-1566). Pathogenic blood coagulation or thrombosis aggravates the symptoms of chromic liver infections and underlines the lethality of many infectious diseases (Levi, M., Keller, T. T., van Gorp, E., and ten Cate, H. (2003) *Cardiovasc. Res.* 60, 26-39; Marsden, P. A., Ning, Q., Fung, L. S., Luo, X., Chen, Y., Mendicino, M., Ghanekar, A., Scott, J. A., Miller, T., Chan, C. W., Chan, M. W., He, W., Gorczynski, R. M., Grant, D. R., Clark, D. A., Phillips, M. J., and Levy, G. A. (2003) *J. Clin. Invest* 112, 58-66; and Opal, S. M. and Esmon, C. T. (2003) *Crit Care* 7, 23-38). Malignant cells have been found to constitutively express the procoagulant tissue factor, generating hypercoagulability in cancer patients (Agorogiannis, E. I. and Agorogiannis, G. I. (2002) *Lancet* 359, 1440; Lorenzet, R. and Donati, M. B. (2002) *Thromb. Haemost.* 87, 928-929; and Ornstein, D. L., Meehan, K. R., and Zacharski, L. R. (2002) *Semin. Thromb. Hemost.* 28, 19-28). These recent observations have attracted significant attention to the potential use of anticoagulants or antithrombotic agents as part of new treatment strategies for devastating human cancers (Loynes, J. and Zacharski, L. (2003) *Expert. Opin. Ther. Targets.* 7, 399-404; Kakkar, A. K. (2003) *Cancer Treat. Rev.* 29 *Suppl* 2, 23-26; Levine, M. N. (2003) *Cancer Treat. Rev.* 29 *Suppl* 2, 19-22; Lee, A. Y. (2003) *Expert. Opin. Pharmacother.* 4, 2213-2220; and Deitcher, S. R. (2003) *J. Thromb. Thrombolysis.* 16, 21-31) and infectious diseases (Marsden, P. A., Ning, Q., Fung, L. S., Luo, X., Chen, Y., Mendicino, M., Ghanekar, A., Scott, J. A., Miller, T., Chan, C. W., Chan, M. W., He, W., Gorczynski, R. M., Grant, D. R., Clark, D. A., Phillips, M. J., and Levy, G. A. (2003) *J. Clin. Invest* 112, 58-66; Opal, S. M. and Esmon, C. T. (2003) *Crit Care* 7, 23-38; Geisbert, T. W., Hensley, L. E., Jahrling, P. B., Larsen, T., Geisbert, J. B., Paragas, J., Young, H. A., Fredeking, T. M., Rote, W. E., and Vlasuk, G. P. (2003) *Lancet* 362, 1953-1958; Robertson, M. (2003) *Drug Discov. Today* 8, 768-770; and Schultz, M. J., Levi, M., and van der, P. T. (2003) *Curr. Drug Targets.* 4, 315-321). However, the current generation of antithrombotic agents, among which many are thrombin inhibitors, lacks the required efficacy/safety. and cost-effectiveness (Gresele, P. and Agnelli, G. (2002) *Trends Pharmacol. Sci.* 23, 25-32; Vorchheimer, D. A. and Fuster, V. (2002) *Eur. Heart J.* 23, 1142-1144; and Weitz, J. I. and Buller, H. R. (2002) *Circulation* 105, 1004-1011) for realizing the tremendous potential of anticoagulant therapy in many disease indications.

Blood coagulation is one of the best-characterized physiological responses that involve tightly-regulated cascades of protein-protein interaction and enzyme activation reactions (Mann, K. G. (1999) *Thromb. Haemost.* 82, 165-174; and Furie, B. and Furie, B. C. (1988) *Cell* 53, 505-518). The coagulation processes can be triggered by the exposure of blood to open air and/or upon injury of the vascular wall (e.g. at the sites of atherosclerotic lesions). The clotting of the free blood is the result of the so-called "intrinsic" coagulation pathway started by the activation of factors XII and XI. Blood clots formed in closed circulation are initiated by the "extrinsic" coagulation pathway through contact of blood with exposed tissue factors (TF) on injured blood vessels. The two pathways converge on the activation of the circulating coagulation factor X into the factor Xa enzyme, which in turn is assembled into a macromolecular enzyme-cofactor complex, called the prothrombinase, containing factor Xa, factor Va, calcium ions and a phospholipid surface (Mann, K. G. (1999) *Thromb. Haemost.* 82, 165-174). There also appears to be a third pathway of blood coagulation, in which factor Xa of the prothrombinase is replaced by a tissue-specific Xa-like protein, the fgl2/fibroleukin, induced by the invasion of pathogenic viruses (Marsden, P. A., Ning, Q., Fung, L. S., Luo, X., Chen, Y., Mendicino, M., Ghanekar, A., Scott, J. A., Miller, T., Chan, C. W., Chan, M. W., He, W., Gorczynski, R. M., Grant, D. R., Clark, D. A., Phillips, M. J., and Levy, G. A. (2003) *J. Clin. Invest* 112, 58-66; and Chan, C. W., Chan,. M. W., Liu, M., Fung, L., Cole, E. H., Leibowitz, J. L., Marsden, P. A., Clark, D. A., and Levy, G. A. (2002) *J. Immunol.* 168, 5170-5177). As well, factor Xa may be generated from the inactive precursor factor X by endogenous proteases secreted by invading microbes (Ntefidou, M., Elsner, C., Spreer, A., Weinstock, N., Kratzin,. H. D., and Ruchel, R. (2002) *Mycoses* 45 *Suppl* 1, 53-56; and Schoen, C., Reichard, U., Monod, M., Kratzin, H. D., and Ruchel, R. (2002) *Med. Mycol.* 40, 61-71). In all the coagulation pathways, the prothrombinase assembly rapidly converts prothrombin into active thrombin, the ultimate protease resulting from the coagulation cascades. Upon generation, thrombin induces formation of the fibrin clot from the soluble fibrinogen, activates the fibrin cross-linking factor XIII, stimulates the aggregation of platelets and catalyzes the conversion of factors V, VIII and XI into Va, VIIIa and XIa to amplify its own production. Thrombin also binds to the cell-anchored thrombomodulin to form the thrombin-thrombomodulin complex, which in turn activates protein C and the thrombin-activatable fibrinolysis inhibitor (TAFI), initiating the natural anticoagulation and anti-fibrinolysis pathways (Nesheim, M., Wang, W., Boffa, M., Nagashima, M., Morser, J., and Bajzar, L. (1997) *Thromb. Haemost.* 78, 386-391). The critical role of thrombin in making blood clots and in thrombotic diseases has stimulated in-depth studies on the structure and function of thrombin (Berliner, J. L. (1992) *Thrombin: structure and function* Plenum Press, New York) and the design of thrombin inhibitors as novel anticoagulants (Weitz, J. I. and Buller, H. R. (2002) *Circulation* 105, 1004-1011; Fenton, J. W., Ni, F., Witting, J. I., Brezniak, D. V., Andersen, T. T., and Malik, A.

B. (1993) *Adv. Exp. Med. Biol.* 340, 1-13; and Song, J. and Ni, F. (1998) *Biochem. Cell Biol.* 76, 177-188).

The mainstays of clinical anticoagulant treatments are heparin, which is a cofactor of plasma-derived and naturally-occurring inhibitors of thrombin, and coumarins, such as arfarin, which antagonize the biosynthesis of vitamin K-dependent coagulation factors. Although effective and widely used, heparins and coumarins have practical limitations because their pharmacokinetics and anticoagulation effects are unpredictable, with the risk of many undesirable side effects, such as hemorraghing and thrombocytopenia resulting in the need for close monitoring of their use. Low-molecular-weight heparins (LMWHs) provide a more predictable anticoagulant response; however, discontinuation of heparin treatment can result in a thrombotic rebound due to the inability of these compounds to inhibit clot-bound thrombin. More seriously, heparins are involved in many aspects of cellular physiology (Kakkar, A. K. (2003) *Cancer Treat. Rev.* 29 Suppl 2, 23-26), making their long-term uses as anticoagulants plagued with potential side effects.

There is a need for direct thrombin inhibitors (DTI) that are able to target: (1) free and (2) clot-bound thrombin. Hirudin is a member of only the first class and is a naturally occurring polypeptide produced by the blood sucking leech *hirudo medicinalis*. Hirudin and its recombinant forms bind irreversibly to both the catalytic and substrate-recognition sites of thrombin. Other DTIs with lower molecular weights, such as DuP714, PPACK, and efegatran, have subsequently been developed, and these agents are better inhibitors of clot-bound thrombin and the thrombotic processes at sites of arterial damage. Such compounds inhibit thrombin by covalent attachment and can result in toxicity and nonspecific inhibition of other proteins. Eventually, further development of these small molecules was mostly abandoned. In recent years, the development of low molecular weight, active site-directed, and reversible DTIs has resulted in a number of highly potent and selective compounds, such as inogatran and melagatran. Ongoing clinical trails suggest that the binding characteristics of these low molecular weight DTIs may also result in bleeding complications.

The main problem of small molecular weight compounds is their limited specificity since thrombin belongs to the family of serine proteases and these compounds do not have strong specificity toward thrombin alone. Also available data so far indicate that the development of the small-molecule DTIs of thrombin is more time-consuming than other inhibitory molecules. For example, it has proven difficult to disrupt high-affinity and highly-specific protein-protein interactions by use of small-molecule inhibitors (Benard, V., Bokoch, G. M., and Diebold, B. A. (1999) *Trends Pharmacol. Sci.* 20, 365-370; Cochran, A. G. (2001) *Curr. Opin. Chem. Biol.* 5, 654-659; and Veselovsky, A. V., Ivanov, Y. D., Ivanov, A. S., Archakov, A. I., Lewi, P., and Janssen, P. (2002) *J. Mol. Recognit.* 15, 405-422). On the other hand, in addition to natural proteins (e.g. antibodies), novel polypeptide ligands have been discovered and shown to possess the ability to interfere selectively with the targeted protein-protein interactions (Cochran, A. G. (2001) *Curr. Opin. Chem. Biol.* 5, 654-659; Veselovsky, A. V., Ivanov, Y. D., Ivanov, A. S., Archakov, A. I., Lewi, P., and Janssen, P. (2002) *J. Mol. Recognit.* 15, 405-422; Juliano, R. L., Astriab-Fisher, A., and Falke, D. (2001) *Mol. Interv.* 1, 40-53; and Sidhu, S. S., Fairbrother, W. J., and Deshayes, K. (2003) *Chembiochem.* 4, 14-25). Linking of weak-binding molecules to create bivalent or multivalent molecules (DiMaio, J., Gibbs, B., Munn, D., Lefebvre, J., Ni, F., and Konishi, Y. (1990) *J. Biol. Chem.* 265, 21698-21703; and Maragnore, J. M., Bourdon, P., Jablonski, J., Ramachandran, K. L., and Fenton, J. W. (1990) *Biochemistry* 29, 7095-7101) has also emerged as a general strategy for the design of potent inhibitors of enzymes (Jahnke, W., Florsheimer, A., Blommers, M. J., Paris, C. G., Heim, J., Nalin, C. M., and Perez, L. B. (2003) *Curr. Top. Med. Chem.* 3, 69-80; and Shuker, S. B., Hajduk, P. J., Meadows, R. P., and Fesik, S. W. (1996) *Science* 274, 1531-1534), receptors (Jahnke, W., Florsheimer, A., Blommers, M. J., Paris, C. G., Heim, J., Nalin, C. M., and Perez, L. B. (2003) *Curr. Top. Med. Chem.* 3, 69-80; and Kramer, R. H. and Karpen, J. W. (1998) *Nature* 395, 710-713) and protein-protein interactions (Song, J. and Ni, F. (1998) *Biochem. Cell Biol.* 76, 177-188; Mammen, M., Choi, S. K., and Whitesides, G. M. (1998) *Angew. Chem. Int. Ed.* 37, 2754-2794; and Mourez, M., Kane, R. S., Mogridge, J., Metallo, S., Deschatelets, P., Sellman, B. R., Whitesides, G. M., and Collier, R. J. (2001) *Nat. Biotechnol.* 19, 958-961). Intervention of cellular and physiological processes with multivalent polypeptides in particular allows access to the built-in evolutionary specificity of naturally-occurring protein-protein interactions, potentially avoiding the non-specific binding or side effects often seen with small molecules. The synthetic compound bivalirudin is one example of the better DTIs with two covalently linked groups that bind to both the catalytic and substrate-recognition sites of thrombin.

"In late 1988, a research program was initiated at the Biotechnology Research Institute (BRI) on the design of thrombiu inhibitors as antithrombotic agents. In this research program, a series of novel compounds (the Canadian version of Angiomax® (bivalirudin)) (Fenton, J. W., Ni, F., Witting, J. I., Breznialc, D. V., Andersen, T. T., and Malik, A. B. (1993) *Adv. Exp. Med. Biol.* 340, 1-13; Song, J. and Ni, F. (1998) *Biochem. Cell Riot* 76, 177-188; DiMaio, J., Konislik Y., U.S. Pat. No. 6,060,451; and CA 2,085,465) that mimic the multivalent action of biradin, a natural antithrombin from medicinal leeches were discovered. These early research efforts have started to pay off as the related bivalent peptide, bivalirudin or hiralog, mimicking the action of hirudin has recently proved its clinical efficacy (Weitz, J. I. and Buller, H. R. (2002) *Circulation* 105, 1004-1011; Hirsh, J. (2003) *Thromnb. Res.* 109Suppl 1, S1-S8; Salarn, A. M. (2003) *Expert. Opin. Investig. Drugs* 12, 1027-1033; and Wykrzykowska, J. J., Kathiresan, S., and Jang, I. K. (2003) *J. Thromb. Thrombolysis* 15, 47-57)."

"Thrombin inhibitors issued from the research program were also disclosed in WO99/19356. These peptide inhibitors contain two covalently-linked motifs that bind to a large surface area encompassing the catalytic active site and a protein recognition exosite of thrombin. One of these peptide molecules, P53, has an amino acid sequence of (d)F-P-R-P-Q-S-H-N-D-G-D-F-B-E-I-P-E-E-Y-L-Q (DiMaio, J., Gibbs, B., Munn, D., Lefebvre, J, Ni, F., and Konishi, Y. (1990) *J. Biol. Chem.* 265, 21698-21703; U.S. Pat. No. 6,060,451; and CA 2,085,465), which inhibits human α-thrombin with a $K_i$ of ~2.8 nM. The clinically-tested peptide known as hirulog or bivalirudin has a sequence of (d)F-P-R-P-G-G-G-G-N-G-D-F-E-E-I-P-E-E-Y-L, which is also a strong inhibitor of human α-thrombin ($K_i$~2.3 nM) (Maragnore, J. M., Bourdon, P., Jablonski, J., Ramachandran, K. L., and Fenton, J. W. (1990) *Biochemistry* 29, 7095-7101). Hirulog-8 was approved and adopted for clinical uses since January 2001 under the trademark, Angiomax® (bivalirudin). However, the cost of Angiomax® (bivalirudin) is prohibitive since it contains an amino acid residue in the (d)-configuration, i.e. (d)F or (d)Phe, requiring chemical synthesis, limiting broader clinical applications."

The latest clinical experiences showed that uses of the current generation of antithrombotic agents, among which many are direct thrombin inhibitors, can cause prolonged systemic bleeding during anticoagulation and may be associated with rebound activation of coagulation and the re-occlusion of opened blood vessels after anticoagulant therapy (Gresele, P. and Agnelli, G. (2002) *Trends Pharmacol. Sci.* 23, 25-32; Vorchheimer, D. A. and Fuster, V. (2002) *Eur. Heart J.* 23, 1142-1144; and Weitz, J. I. and Buller, H. R. (2002) *Circulation* 105, 1004-1011). In Canadian patent application CA 2,340,461, Shen et al. replaced the d-Phe moiety at the N-terminus of Bivalirudin with a 12 natural amino acids sequence derived from the thrombin receptor. This peptide, containing the LDPR (SEQ ID NO:1) sequence, exhibited an improved safety/efficacy profile with reduced bleeding complications as compared to Hirulog, despite having a significantly decreased binding affinity to thrombin (Xue, M., Ren, S., Welch, S., and Shen, G. X. (2001) *J. Vasc. Res.* 38, 144-152; and Chen, X., Ren, S., Ma, M. G., Dharmalingam, S., Lu, L., Xue, M., Ducas, J., and Shen, G. X. (2003) *Atherosclerosis* 169, 31-40). The (d)Phe-Pro-Arg sequence of P53 or Hirulog can also be replaced by the natural sequence of human FpA, i.e. acetyl-Asp-Phe-Leu-Ala-Glu-Gly-Gly-Gly-Val-Arg (SEQ IS NO:2) as proposed by Fenton et al (Fenton, J. W., Ni, F., Witting, J. I., Brezniak, D. V., Andersen, T. T., and Malik, A. B. (1993) *Adv. Exp. Med. Biol.* 340, 1-13) and synthesized previously (U.S. Pat. No. 5,433, 940). The bivalent conjugate of FpA has been used along with an N-terminal extension to include a binding moiety for integrins on platelets (Mu, R., Qin, Y., Cha, Y., and Jing, Q. (2002) *Zhonghua Yi. Xue. Za Zhi.* 82, 593-596).

It would thus be highly desirable to be provided with peptide inhibitors of thrombin with good binding affinity and composed of genetically-encodable natural amino acids, as these peptides can be expressed through recombinant DNA or used in gene therapy.

SUMMARY OF THE INVENTION

One aim of the present invention is to provide new peptide inhibitors of thrombin composed of genetically-encodable natural amino acids, as these peptides can be expressed through recombinant DNA or used in gene therapy.

In accordance with the invention, there is proposed to use the template of a tetra-peptide sequence, Phe-Asn-Pro-Arg (SEQ ID NO:3), as the inhibitory element binding to the S-subsites of the thrombin active site, which is linked to the C-terminal fragment of hirudin or other related peptide fragments that bind specifically to the Exosite I of thrombin. The linker can be either the natural amino acid sequences of hirudin, a polyglycine moiety or other suitable polypeptides that bind to the S'-subsites of thrombin.

In accordance with the present invention, there is provided a polypeptide inhibitor of thrombin obtained by the method described herein.

Still in accordance with the present invention, there is provided an isolated or purified polypeptide inhibitor of thrombin consisting of all naturally-occurring amino acids, said inhibitor having general formula (1) of:

SBM-PBM-EBM  (1)

Wherein
SBM is a sequence moiety comprising P-subsite residues of the thrombin inhibitor,
PBM is a sequence moiety comprising P'-subsite residues of the thrombin inhibitor,
EBM is a peptide sequence moiety that binds to the fibrinogen recognition exosite of thrombin or a pharmaceutically acceptable salt thereof.

Preferably, SBM has a sequence comprising Phe-Xaa-Pro-Arg (SEQ ID NO:39) or Trp-Xaa-Pro-Arg (SEQ ID NO:121) at the carboxy-terminal end thereof, where Xaa is a natural amino acid residue, and more preferably, a charged or neutral natural amino acid residue. In one embodiment, Xaa is Asp or Arg. Still preferably, SBM has a sequence containing at the carboxy-terminal end thereof a sequence selected from the group consisting of:

Trp-Asp-Pro-Arg, (SEQ ID NO:5)

Phe-Asn-Pro-Arg, (SEQ ID NO:3)

Phe-Asp-Pro-Arg, (SEQ ID NO:4)

Phe-Gln-Pro-Arg, (SEQ ID NO:41)

Phe-Glu-Pro-Arg, (SEQ ID NO:42)

Phe-His-Pro-Arg, (SEQ ID NO:43)

Tyr-Asn-Pro-Arg, (SEQ ID NO:44)

Tyr-Ser-Pro-Arg, (SEQ ID NO:45)

Ile-Gln-Pro-Arg, (SEQ ID NO:46)

Gly-Ser-Ile-Gln-Pro-Arg, (SEQ ID NO:47)

Ile-Asn-Pro-Arg, (SEQ ID NO:48)

Val-Gln-Pro-Arg, (SEQ ID NO:49)

Ala-Val-Pro-Arg, (SEQ ID NO:50)

Gly-Ser-Ala-Val-Pro-Arg, (SEQ ID NO:51)

Ala-Leu-Pro-Arg, (SEQ ID NO:52)
and

Ala-Ile-Pro-Arg. (SEQ ID NO:53)

In one embodiment of the invention, PMB has a sequence containing a sequence selected from the group consisting of:

Pro-Gln-Ser-His-Asn-Asp-Gly, (SEQ ID NO:54)

Pro-Gln-Arg-His-Asn-Asp-Gly, (SEQ ID NO:55)

Pro-Gln-Arg-Pro-Asn-Asp-Gly, (SEQ ID NO:56)

Pro-Gln-Ser-Arg-Asn-Asp-Gly, (SEQ ID NO:57)

-continued

Pro-Gln-Ile-His-Asn-Asp-Gly, (SEQ ID NO:58)

Pro-Gln-Leu-His-Asn-Asp-Gly, (SEQ ID NO:59)

Pro-Gln-Met-His-Asn-Asp-Gly, (SEQ ID NO:60)

Pro-Gln-Asp-His-Asn-Asp-Gly, (SEQ ID NO:61)

Pro-Gln-His-His-Asn-Asp-Gly, (SEQ ID NO:62)
and

Pro-Gln-Lys-His-Asn-Asp-Gly. (SEQ ID NO:63)

Still in one embodiment of the invention, EBM has a sequence containing at the amino-terminal end thereof a sequence selected from the group consisting of:

Asp-Phe-Glu-Glu-Ile-Pro-Glu-Glu-Tyr-Leu-Gln, (SEQ ID NO:64)

Asp-Phe-Glu-Pro-Ile-Pro-Glu-Glu-Tyr-Leu-Gln, (SEQ ID NO:65)

Asp-Tyr-Glu-Pro-Ile-Pro-Glu-Glu-Tyr-Leu-Gln, (SEQ ID NO:66)

Asp-Phe-Glu-Pro-Ile-Pro-Glu-Glu-Tyr-Leu, (SEQ ID NO:67)
and

Asp-Tyr-Glu-Pro-Ile-Pro-Glu-Glu-Tyr-Leu. (SEQ ID NO:68)

In a particular embodiment, the isolated inhibitor has a sequence comprising a sequence selected from the following group consisting of:

(SEQ ID NO:22)
Trp-Asp-Pro-Arg-Pro-Gln-Arg-His-Asn-Asp-Gly-Asp-
Phe-Glu-Pro-Ile-Pro-Glu-Glu-Tyr-Leu-Gln, (SEQ ID NO:23)
Trp-Asp-Pro-Arg-Pro-Gln-Arg-His-Asn-Asp-Gly-Asp-
Tyr-Glu-Pro-Ile-Pro-Glu-Glu-Tyr-Leu-Gln, (SEQ ID NO:21)
Trp-Asp-Pro-Arg-Pro-Gln-Arg-His-Asn-Asp-Gly-Asp-
Phe-Glu-Glu-Ile-Pro-Glu-Glu-Tyr-Leu-Gln, (SEQ ID NO:24)
Trp-Asp-Pro-Arg-Pro-Gln-Ser-Arg-Asn-Asp-Gly-Asp-
Phe-Glu-Pro-Ile-Pro-Glu-Glu-Tyr-Leu-Gln, (SEQ ID NO:25)
Trp-Asp-Pro-Arg-Pro-Gln-Ser-Arg-Asn-Asp-Gly-Asp-
Tyr-Glu-Pro-Ile-Pro-Glu-Glu-Tyr-Leu-Gln, (SEQ ID NO:31)
Trp-Asp-Pro-Arg-Pro-Gln-Leu-His-Asn-Asp-Gly-Asp-
Phe-Glu-Pro-Ile-Pro-Glu-Glu-Tyr-Leu-Gln, (SEQ ID NO:13)
Phe-Asp-Pro-Arg-Pro-Gln-Ser-His-Asn-Asp-Gly-Asp-
Phe-Glu-Glu-Ile-Pro-Glu-Glu-Tyr-Leu-Gln, (SEQ ID NO:12)
Phe-Asn-Pro-Arg-Pro-Gln-Ser-His-Asn-Asp-Gly-Asp-
Phe-Glu-Glu-Ile-Pro-Glu-Glu-Tyr-Leu-Gln, (SEQ ID NO:14)
Phe-Glu-Pro-Arg-Pro-Gln-Ser-His-Asn-Asp-Gly-Asp-
Phe-Glu-Glu-Ile-Pro-Glu-Glu-Tyr-Leu-Gln, (SEQ ID NO:15)
Phe-His-Pro-Arg-Pro-Gln-Ser-His-Asn-Asp-Gly-Asp-
Phe-Glu-Glu-Ile-Pro-Glu-Glu-Tyr-Leu-Gln, (SEQ ID NO:33)
Phe-Asp-Pro-Arg-Pro-Gly-Gly-Gly-Asn-Gly-Asp-
Phe-Glu-Glu-Ile-Pro-Glu-Glu-Tyr-Leu, (SEQ ID NO:16)
Phe-Asp-Pro-Arg-Pro-Gln-Asp-His-Asn-Asp-Gly-Asp-
Phe-Glu-Glu-Ile-Pro-Glu-Glu-Tyr-Leu-Gln, (SEQ ID NO:17)
Phe-Glu-Pro-Arg-Pro-Gln-Asp-His-Asn-Asp-Gly-Asp-
Phe-Glu-Glu-Ile-Pro-Glu-Glu-Tyr-Leu-Gln, (SEQ ID NO:20)
Phe-Asp-Pro-Arg-Pro-Gln-Arg-His-Asn-Asp-Gly-Asp-
Phe-Glu-Glu-Ile-Pro-Glu-Glu-Tyr-Leu-Gln, (SEQ ID NO:18)
Phe-Asp-Pro-Arg-Pro-Gln-His-His-Asn-Asp-Gly-Asp-
Phe-Glu-Glu-Ile-Pro-Glu-Glu-Tyr-Leu-Gln, (SEQ ID NO:19)
Phe-Asp-Pro-Arg-Pro-Gln-Lys-His-Asn-Asp-Gly-Asp-
Phe-Glu-Glu-Ile-Pro-Glu-Glu-Tyr-Leu-Gln, (SEQ ID NO:29)
Phe-Gln-Pro-Arg-Pro-Gln-Met-His-Asn-Asp-Gly-Asp-
Phe-Glu-Glu-Ile-Pro-Glu-Glu-Tyr-Leu-Gln, (SEQ ID NO:26)
Phe-Asn-Pro-Arg-Pro-Gln-Ile-His-Asn-Asp-Gly-Asp-
Phe-Glu-Glu-Ile-Pro-Glu-Glu-Tyr-Leu-Gln, (SEQ ID NO:27)
Ile-Gln-Pro-Arg-Pro-Gln-Ile-His-Asn-Asp-Gly-Asp-
Phe-Glu-Glu-Ile-Pro-Glu-Glu-Tyr-Leu-Gln, (SEQ ID NO:28)
Gly-Ser-Ala-Val-Pro-Arg-Pro-Gln-Ile-His-Asn-Asp-
Gly-Asp-Phe-Glu-Glu-Ile-Pro-Glu-Glu-Tyr-Leu-Gln,
and (SEQ ID NO:30)
Gly-Ser-Ile-Gln-Pro-Arg-Pro-Gln-Ile-His-Asn-Asp-
Gly-Asp-Phe-Glu-Glu-Ile-Pro-Glu-Glu-Tyr-Leu-Gln.

In still other particular embodiment, the isolated inhibitor has a sequence comprising a sequence selected from the following group consisting of:

(SEQ ID NO:70)
Thr-Phe-Pro-Arg-Pro-Gln-Pro-His-Asn-Asp-Gly-Asp-
Phe-Glu-Glu-Ile-Pro-Glu-Glu-Tyr-Leu-Gln, (SEQ ID NO:71)
Asn-Val-Pro-Arg-Pro-Gln-Ala-His-Asn-Asp-Gly-Asp-
Phe-Glu-Glu-Ile-Pro-Glu-Glu-Tyr-Leu-Gln, (SEQ ID NO:72)
Tyr-Asn-Pro-Arg-Pro-Gln-Ile-His-Asn-Asp-Gly-Asp-
Phe-Glu-Glu-Ile-Pro-Glu-Glu-Tyr-Leu-Gln, (SEQ ID NO:73)
His-Tyr-Pro-Arg-Pro-Gln-Ile-His-Asn-Asp-Gly-Asp-
Phe-Glu-Glu-Ile-Pro-Glu-Glu-Tyr-Leu-Gln, (SEQ ID NO:74)
His-Tyr-Pro-Arg-Pro-Gln-Thr-His-Asn-Asp-Gly-Asp-
Phe-Glu-Glu-Ile-Pro-Glu-Glu-Tyr-Leu-Gln;

(SEQ ID NO:75)
His-Ala-Pro-Arg-Pro-Gln-Ser-His-Asn-Asp-Gly-Asp-
Phe-Glu-Glu-Ile-Pro-Glu-Glu-Tyr-Leu-Gln;

(SEQ ID NO:76)
Ile-Leu-Pro-Arg-Pro-Gln-Met-His-Asn-Asp-Gly-Asp-
Phe-Glu-Glu-Ile-Pro-Glu-Glu-Tyr-Leu-Gln, (SEQ ID NO:77)
Leu-Thr-Pro-Arg-Pro-Gln-Ile-His-Asn-Asp-Gly-Asp-
Phe-Glu-Glu-Ile-Pro-Glu-Glu-Tyr-Leu-Gln, (SEQ ID NO:78)
Asn-Thr-Pro-Arg-Pro-Gln-Phe-His-Asn-Asp-Gly-Asp-
Phe-Glu-Glu-Ile-Pro-Glu-Glu-Tyr-Leu-Gln, (SEQ ID NO:79)
Gln-Ser-Pro-Arg-Pro-Gln-Leu-His-Asn-Asp-Gly-Asp-
Phe-Glu-Glu-Ile-Pro-Glu-Glu-Tyr-Leu-Gln, (SEQ ID NO:80)
His-Val-Pro-Arg-Pro-Gln-Leu-His-Asn-Asp-Gly-Asp-
Phe-Glu-Glu-Ile-Pro-Glu-Glu-Tyr-Leu-Gln, (SEQ ID NO:81)
His-Thr-Pro-Arg-Pro-Gln-Gln-His-Asn-Asp-Gly-Asp-
Phe-Glu-Glu-Ile-Pro-Glu-Glu-Tyr-Leu-Gln, (SEQ ID NO:82)
Leu-Met-Pro-Arg-Pro-Gln-Ser-HIs-Asn-Asp-Gly-Asp-
Phe-Glu-Glu-Ile-Pro-Glu-Glu-Tyr-Leu-Gln, (SEQ ID NO:83)
Ile-Asn-Pro-Arg-Pro-Gln-Met-His-Asn-Asp-Gly-Asp-
Phe-Glu-Glu-Ile-Pro-Glu-Glu-Tyr-Leu-Gln, (SEQ ID NO:84)
Val-Thr-Pro-Arg-Pro-Gln-Pro-His-Asn-Asp-Gly-Asp-
Phe-Glu-Glu-Ile-Pro-Glu-Glu-Tyr-Leu-Gln, (SEQ ID NO:85)
Thr-Asp-Pro-Arg-Pro-Gln-Ile-His-Asn-Asp-Gly-Asp-
Phe-Glu-Glu-Ile-Pro-Glu-Glu-Tyr-Leu-Gln, (SEQ ID NO:86)
Pro-Glu-Pro-Arg-Pro-Gln-Leu-His-Asn-Asp-Gly-Asp-
Phe-Glu-Glu-Ile-Pro-Glu-Glu-Tyr-Leu-Gln;

(SEQ ID NO:87)
Gly-Asn-Pro-Arg-Pro-Gln-Tyr-His-Asn-Asp-Gly-Asp-
Phe-Glu-Glu-Ile-Pro-Glu-Glu-Tyr-Leu-Gln, (SEQ ID NO:88)
Tyr-Ser-Pro-Arg-Pro-Gln-Ile-His-Asn-Asp-Gly-Asp-
Phe-Glu-Glu-Ile-Pro-Glu-Glu-Tyr-Leu-Gln, (SEQ ID NO:89)
Tyr-Asn-Pro-Arg-Pro-Gln-His-His-Asn-Asp-Gly-Asp-
Phe-Glu-Glu-Ile-Pro-Glu-Glu-Tyr-Leu-Gln, (SEQ ID NO:90)
Ile-Gln-Pro-Arg-Pro-Gln-Met-His-Asn-Asp-Gly-Asp-
Phe-Glu-Glu-Ile-Pro-Glu-Glu-Tyr-Leu-Gln, (SEQ ID NO:91)
Ile-Met-Pro-Arg-Pro-Gln-Met-His-Asn-Asp-Gly-Asp-
Phe-Glu-Glu-Ile-Pro-Glu-Glu-Tyr-Leu-Gln, (SEQ ID NO:92)
Ile-Ile-Pro-Arg-Pro-Gln-Met-His-Asn-Asp-Gly-Asp-
Phe-Glu-Glu-Ile-Pro-Glu-Glu-Tyr-Leu-Gln, (SEQ ID NO:93)
Ile-His-Pro-Arg-Pro-Gln-Met-His-Asn-Asp-Gly-Asp-
Phe-Glu-Glu-Ile-Pro-Glu-Glu-Tyr-Leu-Gln, (SEQ ID NO:76)
Ile-Leu-Pro-Arg-Pro-Gln-Met-His-Asn-Asp-Gly-Asp-
Phe-Glu-Glu-Ile-Pro-Glu-Glu-Tyr-Leu-Gln;

(SEQ ID NO:94)
Val-Gln-Pro-Arg-Pro-Gln-Gln-His-Asn-Asp-Gly-Asp-
Phe-Glu-Glu-Ile-Pro-Glu-Glu-Tyr-Leu-Gln, (SEQ ID NO:95)
Val-Met-Pro-Arg-Pro-Gln-Gln-His-Aan-Asp-Gly-Asp-
Phe-Glu-Glu-Ile-Pro-Glu-Glu-Tyr-Leu-Gln, (SEQ ID NO:96)
Val-Gln-Pro-Arg-Pro-Gln-Pro-His-Asn-Asp-Gly-Asp-
Phe-Glu-Glu-Ile-Pro-Glu-Glu-Tyr-Leu-Gln, (SEQ ID NO:97)
Leu-His-Pro-Arg-Pro-Gln-Leu-His-Asn-Asp-Gly-Asp-
Phe-Glu-Glu-Ile-Pro-Glu-Glu-Tyr-Leu-Gln, (SEQ ID NO:98)
Leu-Ile-Pro-Arg-Pro-Gln-Met-His-Asn-Asp-Gly-Asp-
Phe-Glu-Glu-Ile-Pro-Glu-Glu-Tyr-Leu-Gln, (SEQ ID NO:99)
Met-Gln-Pro-Arg-Pro-Gln-Met-His-Asn-Asp-Gly-Asp-
Phe-Glu-Glu-Ile-Pro-Glu-Glu-Tyr-Leu-Gln, (SEQ ID NO:100)
Met-Met-Pro-Arg-Pro-Gln-Met-His-Asn-Asp-Gly-Asp-
Phe-Glu-Glu-Ile-Pro-Glu-Glu-Tyr-Leu-Gln,

-continued

Ala-Val-Pro-Arg-Pro-Gln-Ile-His-Asn-Asp-Gly-Asp- (SEQ ID NO:101)
Phe-Glu-Glu-Ile-Pro-Glu-Glu-Tyr-Leu-Gln,

Ala-Leu-Pro-Arg-Pro-Gln-Ile-His-Asn-Asp-Gly-Asp- (SEQ ID NO:102)
Phe-Glu-Glu-Ile-Pro-Glu-Glu-Tyr-Leu-Gln,

Ala-Ile-Pro-Arg-Pro-Gln-Gln-His-Asn-Asp-Gly-Asp- (SEQ ID NO:103)
Phe-Glu-Glu-Ile-Pro-Glu-Glu-Tyr-Leu-Gln,

Ala-Ile-Pro-Arg-Pro-Gln-Pro-His-Asn-Asp-Gly-Asp- (SEQ ID NO:104)
Phe-Glu-Glu-Ile-Pro-Glu-Glu-Tyr-Leu-Gln,

Ala-Met-Pro-Arg-Pro-Gln-Ala-His-Asn-Asp-Gly-Asp- (SEQ ID NO:105)
Phe-Glu-Glu-Ile-Pro-Glu-Glu-Tyr-Leu-Gln,

Ala-Tyr-Pro-Arg-Pro-Gln-Ala-His-Asn-Asp-Gly-Asp- (SEQ ID NO:106)
Phe-Glu-Glu-Ile-Pro-Glu-Glu-Tyr-Leu-Gln,

Ala-Gln-Pro-Arg-Pro-Gln-Ile-His-Asn-Asp-Gly-Asp- (SEQ ID NO:107)
Phe-Glu-Glu-Ile-Pro-Glu-Glu-Tyr-Leu-Gln,

Ala-Thr-Pro-Arg-Pro-Gln-Leu-His-Asn-Asp-Gly-Asp- (SEQ ID NO:108)
Phe-Glu-Glu-Ile-Pro-Glu-Glu-Tyr-Leu-Gln,

Ala-Thr-Pro-Arg-Pro-Gln-Val-His-Asn-Asp-Gly-Asp- (SEQ ID NO:109)
Phe-Glu-Glu-Ile-Pro-Glu-Glu-Tyr-Leu-Gln,

Pro-Ile-Pro-Arg-Pro-Gln-Ile-His-Asn-Asp-Gly-Asp- (SEQ ID NO:110)
Phe-Glu-Glu-Ile-Pro-Glu-Glu-Tyr-Leu-Gln,

Pro-His-Pro-Arg-Pro-Gln-Ile-His-Asn-Asp-Gly-Asp- (SEQ ID NO:111)
Phe-Glu-Glu-Ile-Pro-Glu-Glu-Tyr-Leu-Gln,

Pro-Trp-Pro-Arg-Pro-Gln-Leu-His-Asn-Asp-Gly-Asp- (SEQ ID NO:112)
Phe-Glu-Glu-Ile-Pro-Glu-Glu-Tyr-Leu-Gln,

Pro-Asn-Pro-Arg-Pro-Gln-Val-His-Asn-Asp-Gly-Asp- (SEQ ID NO:113)
Phe-Glu-Glu-Ile-Pro-Glu-Glu-Tyr-Leu-Gln,

Thr-Ile-Pro-Arg-Pro-Gln-Ile-His-Asn-Asp-Gly-Asp- (SEQ ID NO:114)
Phe-Glu-Glu-Ile-Pro-Glu-Glu-Tyr-Leu-Gln,

Asn-Asp-Pro-Arg-Pro-Gln-Lys-His-Asn-Asp-Gly-Asp- (SEQ ID NO:115)
Phe-Glu-Glu-Ile-Pro-Glu-Glu-Tyr-Leu-Gln,
and Asn-Ser-Pro-Arg-Pro-Gln-Leu-His-Asn-Asp-Gly-Asp- (SEQ ID NO:116)
Phe-Glu-Glu-Ile-Pro-Glu-Glu-Tyr-Leu-Gln.

In accordance with the present invention, there is also provided a method for selecting a polypeptide inhibitor of thrombin consisting of all naturally occurring amino acids and possessing a strong anti-clotting activity, said method comprising the steps of:

a) generating a phage-displayed library of polypeptides of sequence:

SBM-PBM-EBM, wherein,

SBM has a sequence selected from the group consisting of Xaa-Xaa-Pro-Arg, Xaa-Xaa-Xaa-Pro-Arg, and Xaa-Xaa-Xaa-Xaa-Pro-Arg;

PBM has a sequence selected from the group consisting of Pro-Aaa1-Xaa-Aaa2-Aaa3-Aaa4-Aaa5 and Pro-Aaa1-Aaa2-Aaa3-Aaa4-Aaa5-Aaa6, wherein Xaa is a random (i.e. variable) natural amino acid and Aaa1, Aaa2, Aaa3, Aaa4, Aaa5 and Aaa6 represent fixed natural amino acids in the librairy; and EBM has a sequence selected from the group consisting of Asp-Phe-Glu-Glu-Ile-Pro-Glu-Glu-Tyr-Leu-Gln (SEQ ID NO:64), Asp-Phe-Glu-Pro-Ile-Pro-Glu-Glu-Tyr-Leu-Gln (SEQ ID NO:65), Asp-Tyr-Glu-Pro-Ile-Pro-Glu-Glu-Tyr-Leu-Gln (SEQ ID NO:66), Asp-Phe-Glu-Pro-Ile-Pro-Glu-Glu-Tyr-Leu (SEQ ID NO:67), and Asp-Tyr-Glu-Pro-Ile-Pro-Glu-Glu-Tyr-Leu (SEQ ID NO:68);

b) immobilizing active thrombin on a surface;

c) contacting said library with the immobilized thrombin;

d) removing the non-bound and/or cleaved phage particles;

e) propagating bound and uncleaved phage particles remaining after step (d); and f) identifying the sequence of a polypeptide from the propagated phage particles, said polypeptide being an inhibitor of thrombin.

In accordance with the present invention, there is also provided expression cassettes comprising, in addition to the required sequences for obtaining expression in a target nucleic acid sequence, a nucleic acid sequence encoding the polypeptide inhibitors of the present invention, operably linked to the aforementioned required sequences.

Of course, the present invention is to also include recombinant hosts containing one or more of such expression cassettes, as well as the use of such cassettes, recombinant hosts and the polypeptide inhibitors.

For the purpose of the present invention the following terms are defined below.

When making reference to P-subsite and P'-subsite in reference to residues of the thrombin inhibitor, the p- and p'-subsites refers to or represent a division of the peptide sequence at the peptide bond hydrolyzed specifically by thrombin The term "good affinity" in reference to an inhibitor is intended to mean an inhibitor that has an affinity good enough for commercial application. In some cases, some inhibitors may have an affinity, but the affinity is so low that these inhibitors would not be industrially useful in commerce.

BRIEF DESCRIPTION OF THE DRAWINGS

FIG. 1 illustrates a comparison of the basic compositions of the new bivalent inhibitors of thrombin in accordance with the present invention, hereinafter named, FX22, and their inhibition activities, with respect to a hirudin peptide, Bivalirudin and P53;

FIG. 2 illustrates an SDS-PAGE analysis of the expression of FN22 as a fusion protein in *E. coli* BL21 (DE3) cells;

FIG. 3 illustrates an SDS-PAGE analysis of the expression of FD22 as a fusion protein in E. coli BL21 (DE3) cells;

FIG. 5 illustrates an HPLC purification profile of the second step purification of FN22;

FIG. 6 illustrates an HPLC purification profile of the second step purification of FD22;

FIG. 7 illustrates progression curves of clotting of human fibrinogen by human thrombin in the presence of varying concentrations of hirudin[54-65];

FIG. 8 illustrates progression curves of clotting of human fibrinogen by human thrombin in the presence of varying concentrations of FN22;

FIG. 9 illustrates progression curves of clotting of human fibrinogen by human thrombin in the presence of varying concentrations of FD22;

FIG. 10 illustrates progression curves of clotting of human fibrinogen by human thrombin in the presence of varying concentrations of Bivalirudin;

FIG. 11 illustrates inhibition of thrombin by hirudin[54-65] analyzed with the clotting assay;

FIG. 12 illustrates inhibition of thrombin by FN22 analyzed with the clotting assay;

FIG. 13 illustrates inhibition of thrombin by FD22 analyzed with the clotting assay;

FIG. 14 illustrates inhibition of thrombin by Bivalirudin analyzed with the clotting assay;

FIG. 15A illustrates the amino acid sequences of bivalent peptide inhibitors of thrombin. Sequences of the FN22 and FD22 peptides in comparison with two related peptides, P53 and hirulog, both of which contain a residue in the (d)-configuration, i.e. dF or (d)Phe;

FIG. 15B illustrates two primers used to synthesize the gene encoding the FN22 peptide;

In FIG. 16B, lane M is loaded with molecular weight markers (LMW, Amersham Bioscience); lane 1 is loaded with cell lysate without IPTG induction; lane 2 is loaded with cell lysate with IPTG induction, wherein the total protein of cells harbouring pMFH-FN22 was prepared by dissolving the cell pellets in the SDS sample buffer; lanes 3 & 4 are loaded with cell lysate with IPTG induction, wherein the total protein of cells harbouring pMFH-FN22 was prepared by dissolving the cell pellets in Buffer A under a denaturing condition; lane 5 & 6 are loaded with cell lysate with IPTG induction, wherein the total protein of cells harbouring pMFH-FD22 was prepared by dissolving the cell pellets in Buffer A under a denaturing condition;

DETAILED DESCRIPTION OF THE INVENTION

Figure 4:
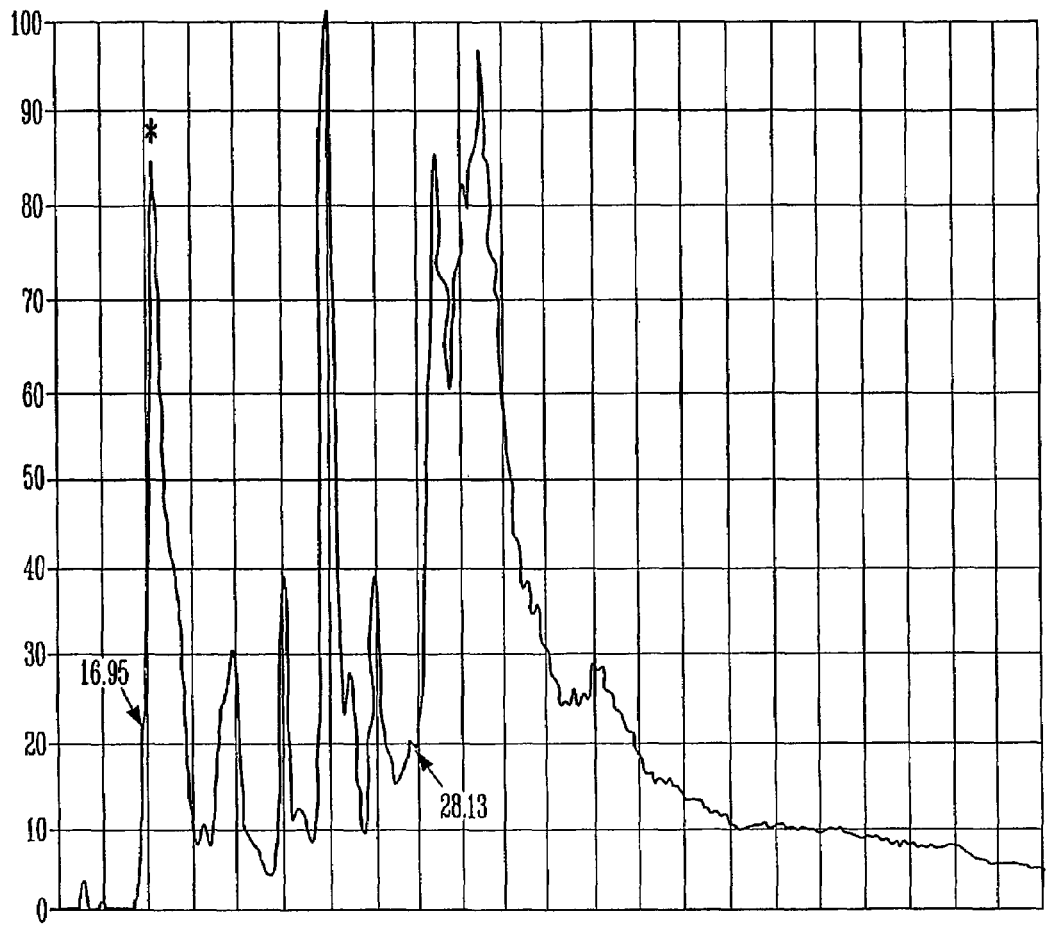
FIG. 4 illustrates an HPLC purification profile of the crude peptide after the FN22 fusion protein was digested by CNBr.

Structurally, the tripeptide, (d)Phe-Pro-Arg, mimics the specific binding of human fibrinopeptide A to thrombin. The aromatic side chain of the (d)Phe residue occupies a binding subsite on thrombin for an (L)Phe at the $P_9$ site, i.e. 8 amino acids away to the N-terminal side of the Arg($P_1$)-Gly($P_1$') peptide bond (Ni, F., Zhu, Y., and Scheraga, H. A. (1995) *J. Mol. Biol.* 252, 656-671; Ni, F., Meinwald, Y. C., Vasquez, M., and Scheraga, H. A. (1989) *Biochemistry* 28, 3094-3105; and Stubbs, M. T., Oschkinat, H., Mayr, I., Huber, R., Angliker, H., Stone, S. R., and Bode, W. (1992) *Eur. J. Biochem.* 206, 187-195). Alternatively, the same binding subsites on thrombin can accommodate tetrapeptide sequences as long as there is an aliphatic, or more preferably an aromatic residue, at the $P_4$ subsite. The $P_4$ residue of the tetrapeptides fulfills the binding of the natural (L)Phe residue at the $P_9$ position of fibrinopeptide A (FpA) (Ni, F., Zhu, Y., and Scheraga, H. A. (1995) *J. Mol. Biol.* 252, 656-671; Ni, F., Ripoll, D. R., and Purisima, E. O. (1992) *Biochemistry* 31, 2545-2554; and Rose, T. and Di Cera, E. (2002) *J. Biol. Chem.* 277, 18875-18880). Some bivalent peptides, although weak binding, have been derived from the activation sequences of thrombin-activated receptors, also referred to as protease-activated receptors (PARs). These peptides carry the LDPR (SEQ ID NO:1) sequence and binding motifs targeting the fibrinogin-recognition exosite of thrombin (Liu, L. W., Vu, T. K., Esmon, C. T., and Coughlin, S. R. (1991) *J. Biol. Chem.* 266, 16977-16980; and Mathews, I. I., Padmanabhan, K. P., Ganesh, V., Tulinsky, A., lshii, M., Chen, J., Turck, C. W., Coughlin, S. R., and Fenton, J. W. (1994) *Biochemistry* 33, 3266-3279). More recent work using substrate libraries has shown that thrombin preferentially cleaves after tetrapeptides carrying the LIFXPR sequence motif (Backes, B. J., Harris, J. L., Leonetti, F., Craik, C. S., and Ellman, J. A. (2000) *Nat. Biotechnol.* 18, 187-193; Edwards, P. D., Mauger, R. C., Cottrell, K. M., Morris, F. X., Pine, K. K., Sylvester, M. A., Scott, C. W., and Furlong, S. T. (2000) *Bioorg. Med. Chem. Left.* 10, 2291-2294; and Furlong, S. T., Mauger, R. C., Strimpler, A. M., Liu, Y. P., Morris, F. X., and Edwards, P. D. (2002) *Bioorg. Med. Chem.* 10, 3637-3647). Indeed, there is an FNPR (SEQ ID NO:3) tetrapeptide sequence in human prothrombin, which is cleaved off efficiently by thrombin to generate the free N-terminus of the A-chain of human thrombin (Ni, F., Zhu, Y., and Scheraga, H. A. (1995) *J. Mol. Biol.* 252, 656-671; and Rose, T. and Di Cera, E. (2002) *J. Biol. Chem.* 277, 18875-18880).

In accordance with the present invention, $P_4$-$P_1$ tetrapeptides, such as F-D-P-R (SEQ ID NO:4) or W-D-P-R (SEQ ID NO:5) have now been incorporated into bivalent and bridge-binding inhibitors of thrombin in replacement of the (d)F-P-R moiety. Rational design and combinatorial selection led to peptides with strong antithrombin and anticlotting activities in the low nanomolar range comparable with those of bivalirudin or P53. The availability of the potent and genetically-encodable polypeptide inhibitors of thrombin of the present invention opens the door for much broader applications of this clinically-successful class of anticoagulants, e.g. through more cost-effective recombinant peptide production, in areas such as gene therapy as well as to improve clinical efficacy/safety through the incorporation of homing peptides for targeted delivery.

In the present invention, the Phe-Asn-Pro-Arg sequence (SEQ ID NO:3) was first substituted for the active site binding element of the P53 bivalent peptide inhibitor of thrombin (DiMaio, J., Gibbs, B., Munn, D., Lefebvre, J., Ni, F., and Konishi, Y. (1990) *J. Biol. Chem.* 265, 21698-21703). The resulting new bivalent peptide served as a template for studying the nature of the $P_4$, $P_3$ and $P_3'$ sites required for enhanced thrombin inhibition. Furthermore, a phage-displayed library of bivalent peptides was constructed in order to explore residue preferences at the $P_4$, $P_3$, and $P_3'$ sites that confer strong bivalency for thrombin binding and at the same time resistance against thrombin cleavage. Synthetic peptides derived from the phage-selected sequences were found to have unique and rather unexpected antithrombin and anticoagulant activities.

FIG. 1 represents the basic compositions of the new inhibitors of thrombin in accordance with the present invention, hereafter also referred to as FX22. A comparison of their compositions with Bivalirudin and P53 was also indicated.

Specific examples of the novel inhibitors are called FN22, FD22, FD22-R, WD22 and WD22-R. The doubling clotting time, DCT, of these inhibitors are also listed in FIG. 1 and Table 1 along with other examples.

The new peptide inhibitors of thrombin of the present invention can be produced cost-effectively through recombinant DNA technologies.

In FIG. 2, the expression was induced with 1 mM IPTG when the cell density reached 0.8 to 1.0 $O.D._{600}$ in LB medium. The cells were harvested after an additional three hours of growth. In FIG. 2, lane M was loaded with low molecular weight markers, lane 1 was loaded with the total cell extracts, whereas lanes 2 and 3 were loaded with the supernatant and the pellet from the fraction purification of the cell lysis. The expressed FN22 fusion proteins were indicated by the arrow.

In FIG. 3, the expression was induced with 1 mM IPTG when the cell density reached 0.8 to 1.0 $O.D._{600}$ in LB medium. The cells were harvested after an additional three hours of growth. In FIG. 3, lane M was loaded with low molecular weight markers, lane 1 was loaded with the cell extracts without IPTG induction, whereas lanes 2 to 3 were loaded with the cell extracts with the IPTG induction, lanes 5 and 6 were loaded with the products of the partial purification and lanes 7 to 9 were loaded with different fractions from the purifications by Sep-Pak™. The expressed fusion proteins were indicated by the arrows.

In FIG. 4, the reversed phase semi-preparative column (C18) was used and the sample was eluted with a concentration gradient of acetonitrile from 10% to 70% with a flow rate of 5 ml/min. The retention time of FN22 is 17.15 min. (the peak was indicated by the asterisk in the figure. The wavelength of the detector was set at 278 nm.

In FIG. 5, the reversed phase semi-preparative column (C18) was used and the sample was eluted with a concentration gradient of acetonitrile from 10% to 70% with a flow rate of 5 ml/min. The wavelength of the detector was set at 215 nm. The fraction between the two arrows was collected and the lyophilized product was tested for the inhibition of thrombin.

Similarly in FIG. 6, the reversed phase semi-preparative column was used and the sample was eluted with a concentration gradient of acetonitrile from 10% to 70% with a flow rate of 5 ml/min. The wavelength of the detector was set at 215 nm. The fraction between the two arrows was collected and the lyophilized product was tested for the inhibition of thrombin.

The DCT reported in FIG. 1 were determined from data extracted from FIGS. 11 to 14.

The amino acid composition of the Phe-Asn-Pro-Arg or Phe-Asp-Pro-Arg sequences, specifically the Phe-Asn or Phe-Asp residues was also varied in order to achieve a control between potent thrombin inhibition and reversible dissociation (through cleavage of the peptides, see FIG. 1 and the Results Section).

Materials and Methods

Materials

All the restriction enzymes were purchased from New England Biolabs (MA, USA). The T4 DNA ligase was obtained from Amersham Biosciences (NJ, USA). Bovine and human α-thrombins were supplied by Haematologic Technologies Inc (VT, USA). The stock solution of human α-thrombin was 12.6 mg/ml in concentration with a specific activity of 3300 NIH units/mg. The stock solution of bovine α-thrombin was 14.6 mg/ml in concentration with a specific activity of 3290 NIH units/mg. The chromogenic substrate Tos-Gly-Pro-Arg-pNA (Tos is Tosyl, and pNa is p-nitroalanine), poly(ethylene glycol)-8000, clottable bovine fibrinogen and the C-terminal peptide of hirudin (Hirudin[54-65]) were purchased from Sigma.

Peptide Preparation

Figure 16:
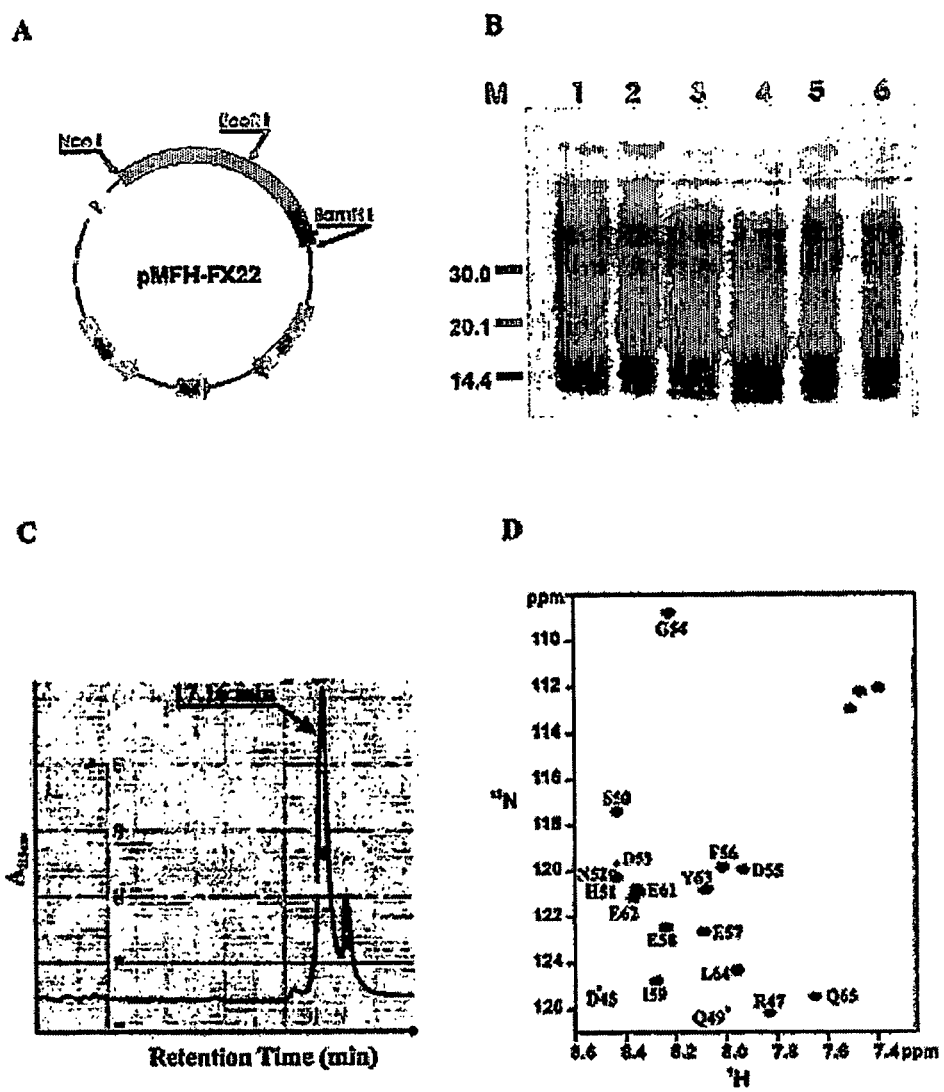
FIG. 16A illustrates the preparation and characterization of recombinant FN22 and FD22 peptides (collectively referred to as FX22) using the expression vector (PMFH) for their preparation.
FIG. 16B illustrates an SDS-PAGE analysis of the expressed fusion proteins containing FN22 and FD22.
FIG. 16C illustrates a HPLC purification profile of the FN22 peptide after CNBr treatment and cleavage of the fusion protein, where peak 1 with a retention time of 17.16 min was collected and confirmed to contain the intact FN22 peptide by mass spectroscopy.
FIG. 16D illustrates a $^1$H-$^{15}$N HSQC spectrum of $^{15}$N-labelled FD22 peptide, wherein the HSQC cross-peaks of residues D45, Q49 and D53 are marked with asterisks and can only be seen at lower contour levels.

The two leading peptides, referred to as FN22(a) and FD22(a) (Table 1 hereinafter), were prepared with a recombinant DNA approach essentially as described previously (Osborne, M. J., Su, Z., Sridaran, V., and Ni, F. (2003) *J. Biomol. NMR* 26, 317-326). The carrier protein termed MFH (FIG. 16A), a variant of the SFC120 fusion carrier (Osborne, M. J., Su, Z., Sridaran, V., and Ni, F. (2003) *J. Biomol. NMR* 26, 317-326), was used to fuse with the targeted peptide. Essentially, MFH is a methionine-free mutant of SFC120 with a six-histidine tag. Other peptides were synthesized by the solid-phase method using FMOC-chemistry either at the Sheldon Biotechnology Centre of McGill University or at the Peptides Facility of the Biotechnology Research Institute, except where indicated.

DNA fragments encoding recombinant peptides were prepared by annealing and amplifying two oligonucleotide primers through the standard PCR procedure. The primers were designed by use of the codon preference of *E Coli*. PCR products were purified by the PCR clean-up kit from Qiagen and double digested with EcoRI and BamHI. The DNA inserts were ligated into the expression vector. The expression constructs were confirmed by DNA sequencing and transformed into the *E coli* BL21 host strain for expression.

Expression of fusion proteins was achieved by transformation of the plasmid into *E. coli* BL21 (DE3) competent cells. A 50 ml of overnight culture grown in LB containing 100 μg/ml ampicillin was used to inoculate 1 L of LB medium supplemented with 100 μg/ml ampicillin. $^{15}$N-labeled peptides were expressed in M9 medium using $^{15}$(NH$_4$)$_2$SO$_4$ (1 g/L) as the sole nitrogen source. The cells were grown at 37° C. to a density of OD$_{600}$=0.8 and induced by adding IPTG to a final concentration of 2 mM. The induced cells were incubated for 12 h at 37° C. and collected by centrifugation (8000 rpm for 20 min). The cell pellet was frozen at −20° C. before further processing.

Thawed cell pellets were resuspended in 6 M urea in 20 mM Tris, 100 mM NaCl buffer, pH 8.0 for 20 min and then sonicated for one minute on ice. The solution was then centrifuged at 7,000 rpm for 20 min. The supernatant was subjected to purification by Ni-NTA affinity chromatography under a denaturing condition. The eluate containing fusion protein was applied to a Sep-Pak column to remove salts. The purified fusion protein was then lyophilized.

CNBr cleavage was used to release the target peptide from the fusion protein. The fusion protein was dissolved in 0.1 M HCl and 6 M guanidine hydrochloride (10 mg protein/ml). Crystalline CNBr was added to a final molar ratio of 100:1 of the fusion protein. The solution was allowed to stand for 12~24 hours. The samples were then purified with Ni-NTA beads to remove MFH fusion carrier and undigested fusion protein if any. The flow-through was desalted, lyophilized and confirmed by electrospray mass spectrometry and $^1$H-$^{15}$N heteronuclear single-quantum correlation (HSQC) NMR experiments.

Both the recombinant and synthetic peptides were finally purified using HPLC on a C$_{18}$ reverse-phase column with a water-acetonitrile gradient with added 0.1% trifluoroacetic acid. For the synthetic peptides, 3-5 mg of the crude material were dissolved in 1 ml of 0.1% TFA in water and the peptide solutions were filtered through a 0.45 μm filter. The filtered solution was applied on a C$_{18}$ HPLC column pre-equilibrated with the water solution of 0.1% TFA. Identities of all purified peptides were verified by electrosprary mass spectrometry.

Clotting Assays

The clotting assays were carried out by use of the protocols described previously (DiMaio, J., Gibbs, B., Munn, D., Lefebvre, J., Ni, F., and Konishi, Y. (1990) *J. Biol. Chem.* 265, 21698-21703; and Witting, J. I., Bourdon, P., Brezniak, D. V., Maraganore, J. M., and Fenton, J. W. (1992) *Biochem. J.* 283 (*Pt* 3), 737-743) The assay employs bovine plasma fibrinogen dissolved at 0.1% in 50 mM Tris-Cl, 100 mM NaCl, 0.1% PEG-8000 at pH 7.6 (i.e. the clotting buffer). Each assay mixture contained a certain concentration of the peptide, and the reaction was started by the addition of human thrombin to a final concentration of 0.1 NIH unit/ml. Optical absorbance of the assay mixtures was measured at 420 nm and 37° C. using the Spectramax™ plate reader. The onset clotting time was determined as an intersection of the baseline and the initial slope of the O.D. change as a result of fibrin clot formation. The concentration of a peptide needed to double the clotting time (DCT) was defined as IC$_{50}$. Peptide concentrations were determined by comparing the O.D.$_{280}$ values of peptide stock solutions in the clotting buffer (vide supra) with the predicted extinction coefficient for each peptide (Gill, S. C. and von Hippel, P. H. (1989) *Anal. Biochem.* 182, 319-326).

Inhibition of the Amidolydic Activity of Thrombin

Kinetics of thrombin-catalyzed hydrolysis of the chromogenic substrate Tos-Gly-Pro-Arg-p-nitroanilide were followed by absorbance at 405 nm on a Spectramax plate reader thermostated at either 25° C. or 37° C. according to the method of Maragnore et al (supra). The concentrations of Tos-Gly-Pro-Arg-p-nitroanilide ranged from 2 to 400 μM. Initial rates were calculated under conditions of <15% hydrolysis of the total substrate. The $K_M$ and $V_{max}$ values were calculated accordingly and $k_{cat}$ values were determined by dividing $V_{max}$ by the enzyme (thrombin) concentration. The inhibition assays were performed in the clotting buffer with a certain fixed concentration of α-thrombin (~0.3 nM) such that linear progress curves were achieved within at least 15 min in the absence of the inhibition. The total volume of the solution was fixed at 200 μl. Reactions were initiated by addition of the chromogenic substrate to the wells containing thrombin and a certain concentration of the peptide inhibitors premixed for less than 2 min. Alternatively, the substrate was first mixed with the peptide inhibitor and the total volume was adjusted to 120 μL using the clotting buffer. Eighty microliters of human α-thrombin in the clotting buffer (~0.3 nM final concentration) was added to initiate the reaction. The concentration of the peptides ranged from 0.5 nM to 10 μM. Kinetics data from initial rate experiments were used to construct Lineweaver-Burke plot; i.e. the relationship of (substrate concentration)$^{-1}$ versus (initial velocity)$^{-1}$ which. were analysed by linear regression with MicroCal Origin 4.1 program (MicroCal, MD) or using the GraphPad Prism software. The $K_i$ values of the inhibitors were determined using the equation:

$$K_i = [I]/\{(SL_0/SL_1)-1\},$$

where

[I] is the inhibitor concentration, $SL_0$ is the slope of the reaction in the absence of inhibitors, and $SL_1$ is the slope of the reaction in the presence of the inhibitor.

Alternatively, Dixon plots of inverse velocity versus the inhibitor concentrations were generated with the Sigma-plot™ software. Every Dixon plot contained an array of data corresponding to different substrate concentrations and the $K_i$ values were determined from the intersections.

Following Peptide Cleavage by HPLC

Figure 18:
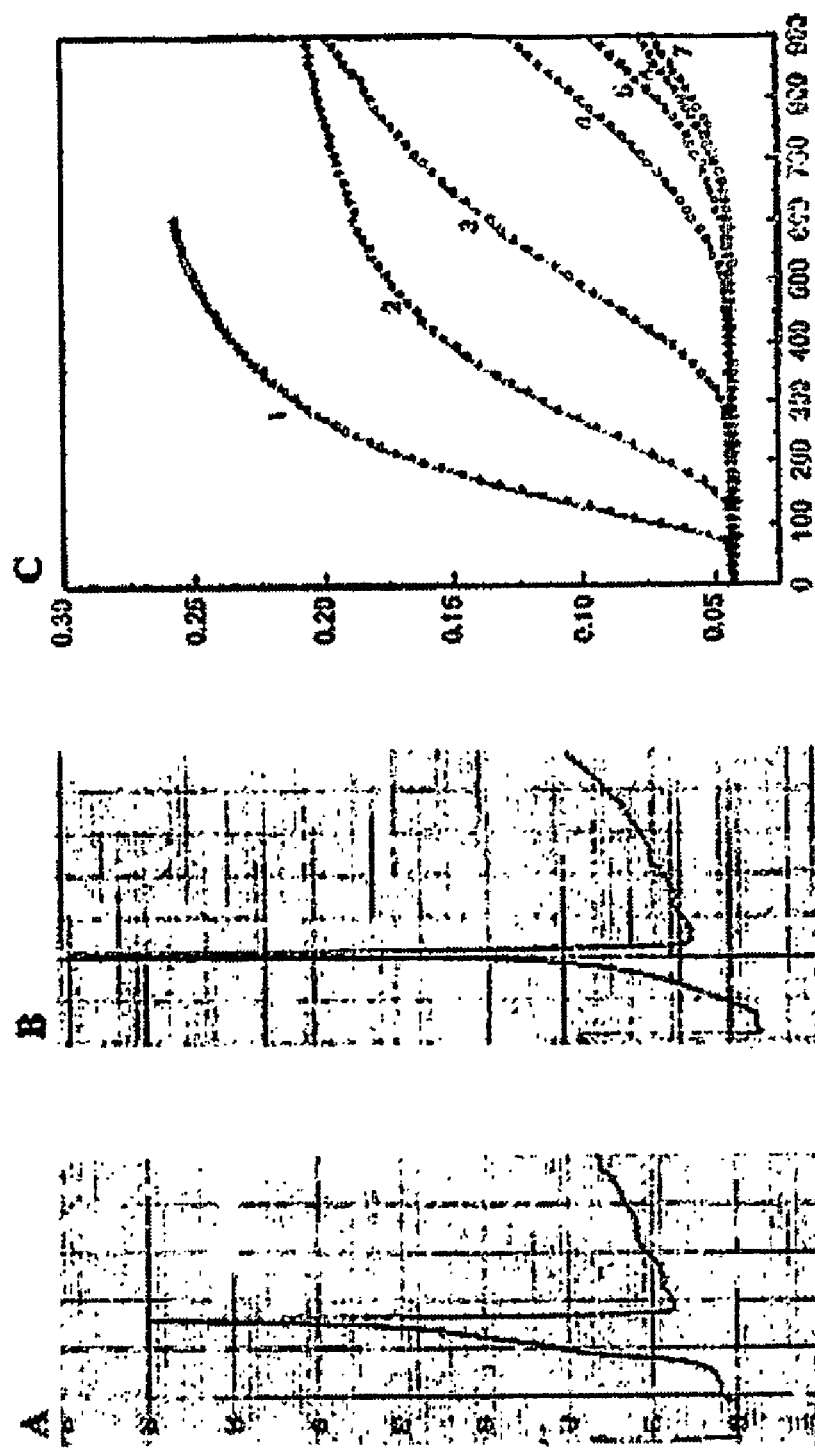
FIGS. 18A and 18B illustrates HPLC profiles (on a $C_8$ column) after 2.0 μM of FN22 and FD22 peptides was incubated with 2.0 μM human α-thrombin for 40 hrs at 25° C., respectively.
FIG. 18C illustrates an analysis of the stability of the FN22 and FD22 peptides in the presence of human α-thrombin by the clotting assay.

Previously reported methods (DiMaio, J., Gibbs, B., Munn; D., Lefebvre, J., Ni, F., and Konishi, Y. (1990) *J. Biol. Chem.* 265, 21698-21703; and Witting, J. I., Bourdon, P., Brezniak, D. V., Maraganore, J. M., and Fenton, J. W. (1992) *Biochem. J.* 283 (*Pt* 3), 737-743) were employed with some modifications (as detailed in the Results section and FIG. 18) to determine whether some bivalent peptides are cleaved by thrombin. Each peptide was dissolved in the clotting buffer at a final concentration of 2.0 µM and incubated at 25° C. with or without 2 µM of human α-thrombin for up to 40 hrs. The samples were then boiled for 2 min to stop the reaction, and centrifuged. The supernatant was acidified by addition of concentrated acetic acid before being loaded on an analytical HPLC $C_{18}$ column and eluted with a linear gradient of 0%-50% (v/v) acetonitrile.

NMR Experiments

NMR spectra were acquired with Bruker 500 or 800 MHz NMR spectrometers using standard pulse sequences (Mori, S., Abeygunawardana, C., Johnson, M. O., and van Zijl, P. C. (1995) *J. Magn Reson. B* 108, 94-98). Heteronuclear NMR experiments including HSQC (2D), HSQC-NOESY (3D) and HSQC-TOCSY (3D) were carried out on the 800 MHz NMR spectrometer. Spectral processing, display and analysis were performed using the XwinNMR software paclkage supplied with the spectrometer system. Sequence-specific assignment of the peptide HSQC spectrum was carried out with the NMRview 4.0 software program.

Construction of Phage Library

The phage vector fd-tetGIIID (MacKenzie, R. and To, R. (1998) *J. Immunol. Methods* 220, 39-49) was a generous gift from Dr. R. MacKenzie (Institute of Biological Sciences, Ottawa). The phage library was constructed essentially as described by Tanha et al. (Tanha, J., Xu, P., Chen, Z., Ni, F., Kaplan, H., Narang, S. A., and MacKenzie, C. R. (2001) *J. Biol. Chem.* 276, 24774-24780). Briefly, double-stranded DNA fragments, encoding the amino acid sequences to be displayed on phage particles were generated and amplified by PCR using a mixture of four synthetic and partly complementary synthetic DNA primers: 1) 5'-catgaccaca gtgcacagca ccaccaccat caccatggct ctggc-3' (SEQ ID NO:6), 2) 5'-ttcct-caaaa tcaccgtcgt tatgmnnttg agggcgcggm nnmnnagagc cagagccatg gtgatg-3' (SEQ ID NO:7), 3) 5'-aacgacggtg attttgagga aattcctgaa gagtatttac aaggtggt-3' (SEQ ID NO:8), and 4) 5'-cgattctgcg gccgcagaag aaccaccttg taaatactc-3' (SEQ ID NO:9). The concentration of the primers in the PCR reaction mixture was 10 µM for primers 1) and 4), and 0.1 µM for primers 2) and 3). The resulting DNA fragments encode a bivalent peptide library with an N-terminal $His_6$-tag and randomized at a number of residue locations (see FIG. 19B). In addition, the fragments contained ApaLI and NotI restriction sites at the N-terminal and C-terminal ends, respectively. The PCR product and the phage vector were purified, digested by ApaLI and NotI, purified again and ligated. The ligation mixture was desalted using the Nanosep™ concentrator (Pall Gelman Laboratory). Subsequently, 0.21 µg of the desalted and ligated product was mixed with 50 µl of competent *Escherichia coli* strain TG1 (Stratagene, Calif.) and the cells were transformed by electroporation. Transformed cells were plated, and the produced phage was collected, purified and stored as reported elsewhere (Tanha, J., Dubuc, G., Hirama, T., Narang, S. A., and MacKenzie, C. R. (2002) *J. Immunol. Methods* 263, 97-109). A total of 1.7 µg of the ligated product yielded a library of approximately $1.0 \times 10^5$ transformants, which allowed ~99% sampling of the library (Deperthes, D. (2002) *Biol. Chem.* 383, 1107-1112). The transformation efficiency was determined by plating a portion of cells onto LB plates containing 50 µg/ml tetracycline.

Selection of Proteolytically Stable Peptides from the Phage Library

Phage particles ($10^9$) were incubated with 0.5 µg of human thrombin at 37° C. for 30 minutes in 26 µl of PBS buffer, pH 7.4. The proteolytic reaction was stopped with an excess of the inhibitor PPACK (Calbiochem) specific for the thrombin active site. The reaction mixture was mixed with 700 µl of the Ni-NTA agarose resin (QIAGEN) in PBS (50% slurry), and phage particles were allowed to bind with gentle agitation for two hours at 0° C. Cleaved phage particles were separated from the resin by washing with 9 ml of PBS buffer, pH 7.4. Bound phage particles were eluted from the resin by 0.7 ml of PBS adjusted to pH 4.4, and immediately neutralized by the addition of 30 µl of 1 M Tris-HCl, pH 8.0. Exponentially growing TG1 cultures (0.3 ml) were infected with the eluted phage at 37° C. for 30 minutes. Serial dilutions were used to estimate phage recovery.

Panning the Phage Library Against Human Thrombin

Individual wells of MaxiSorp plates were coated with 150 µl of 80 µg/ml human α-thrombin in PBS buffer, pH 7.4, at 4° C. under shaking for 2 hours. Wells were rinsed three times with PBS, blocked with 400 µl PBS-2% (w/v) skim milk (2% MPBS) at 4° C. for 2 hours, and rinsed as above. Two hundred microliters of the phage particles (~$10^{12}$ plaque forming units) in 2% MPBS were added to the thrombin-coated wells and incubated with shaking either for 2 hours at 4° C. or for 0.5-1 hours at room temperature (25° C.) without shaking. The wells were rinsed 15 (or 25) times with PBS-0.1% (v/w) Tween™ 20 and then 15 (or 25) times with PBS at the corresponding temperature. Bound phage was eluted by adding 200 µl of freshly prepared 100 mM triethylamine, neutralized with 100 µl 1 M Tris-HCl, pH 7.4, and used to infect TG1 cells as described above. Alternatively, TG1 cells were infected directly by the addition of 300 µl cell culture in the wells (Stoop, A. A. and Craik, C. S. (2003) *Nat. Biotechnol.* 21, 1063-1068).

Results

1: Incorporation of the Tetrapeptide Phe-Asn-Pro-Arg (SEQ ID NO:3) into Bivalent Inhibitors of Thrombin: Recombinant Expression and Characterization The Phe-Asn-Pro-Arg peptide fragment (SEQ ID NO:3) was conjugated to a peptide derived from the C-terminus of hirudin (or hirudin[48-65]) as done previously (DiMaio, J., Gibbs, B., Munn, D., Lefebvre, J., Ni, F., and Konishi, Y. (1990) *J. Biol. Chem.* 265, 21698-21703). The resulting 22-residue chimeric peptide was designated FN22 and contained one proline residue inserted between the two parts in order to decrease the rate of peptide cleavage by thrombin (FIG. 1 and FIG. 15A). The FN22 peptide was then expressed as a fusion protein to a mutant, named MFH, of the SFC120 fusion carrier (Osborne, M. J., Su, Z., Sridaran, V., and Ni, F. (2003) *J. Biomol. NMR* 26, 317-326). The mutant carrier had all the methionine residues of SFC120 replaced by leucines with a His-tag attached in order to simplify peptide purification (FIG. 2 and FIG. 16A). A single methionine residue was inserted between the carrier protein and the FN22 peptide sequence to facilitate release of the peptides by CNBr cleavage.

In FIG. 15A, all peptides contain three distinctive segments, the active site binding moiety, the fibrinogen-recognition exosite binding moiety and a linker sequence. The FN22 and FD22 peptides were prepared by recombinant DNA techniques as described herein (FIGS. 2-6 and FIG. 16).

Figure 17:
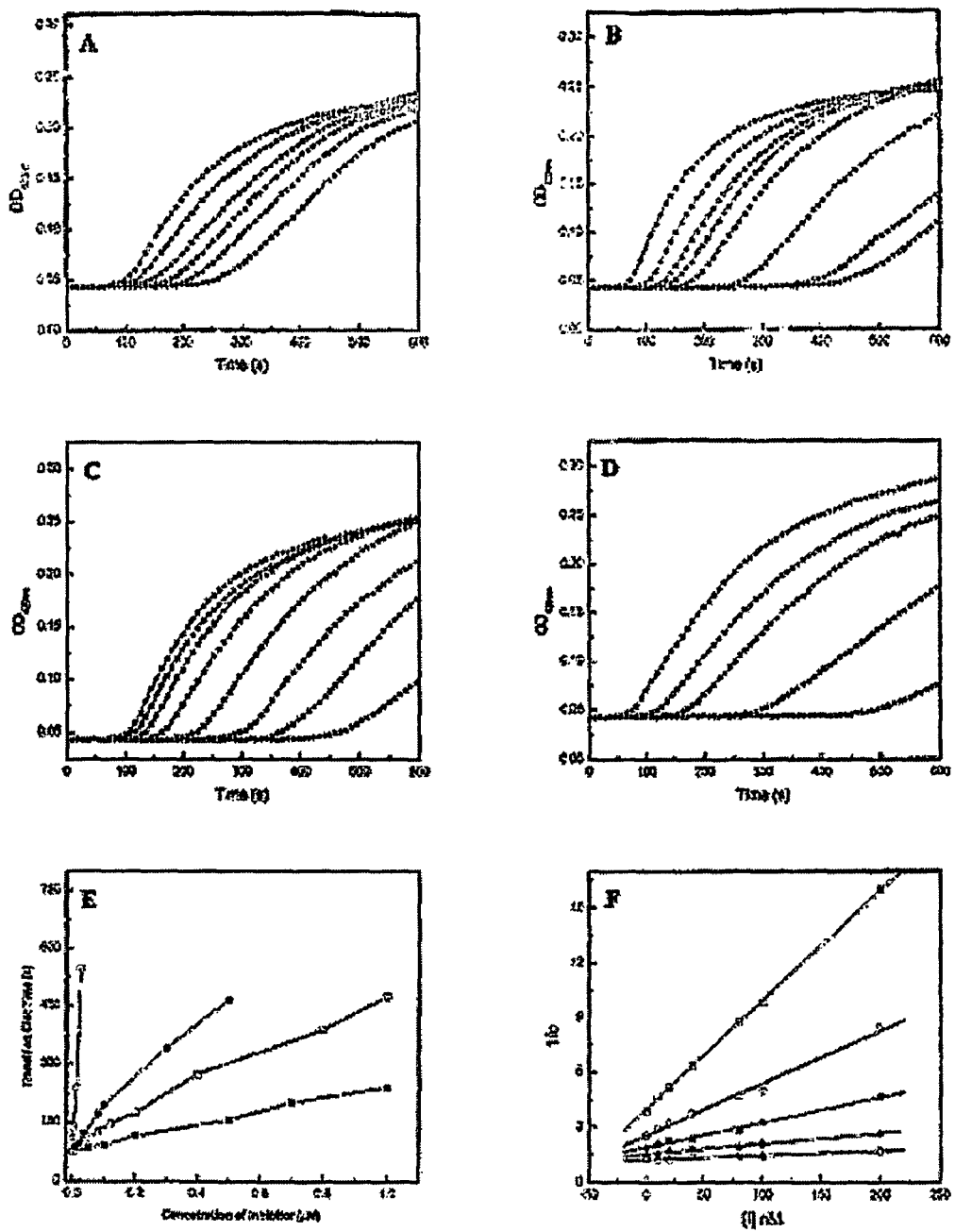
FIGS. 17A to 17D illustrates inhibition curves of thrombin by hirudin[54-65] (FIG. 17A) FN22 (FIG. 17B), FD22 (FIG. 17C) and Hirulog (also called bivalirudin) (FIG. 17D) at various increasing peptide concentrations.
FIG. 17E illustrates the transition clotting time as a function of the peptide concentration for Hirudin[54-65] (solid square), FN22 (open square), FD22 (solid circle) and Hirulog (open circle)
FIG. 17F illustrates the Dixon plot of the inhibition of human α-thrombin-catalyzed hydrolysis of Tos-Gly-Pro-Arg-pNA by FD22 wherein the assays as described herein were performed in the presence of 5 (open square), 10 (open circle), 20 (full square), 50 (full circle) and 80 μM (open circle) of the chromogenic substrate.

The recombinant FN22 peptide had an enhanced anticlotting activity as it further increased the time of fibrinogen clotting catalysed by α-thrombin (FIGS. 8, 17B, 17D 17E and Table 1) compared to the hirudin peptide (FIGS. 7, 17A, 17E and Table 1). The FN22 peptide showed inhibitory activities in the concentration range from 50 nM to 6 μM (FIGS. 8, 17A and 17E). The $IC_{50}$ values for FN22 determined was 289 nM for bovine α-thrombin and 150 nM for human α-thrombin (FIG. 1 and Table 1). In comparison, a hirudin tail peptide has an $IC_{50}$ of 447 nM for human α-thrombin (FIG. 1 and Table 1). Similar experiments showed that the FNPRP peptide alone was a much weaker inhibitor (Table 1) with submillimolar $IC_{50}$ values.

In each of FIGS. 17A to 17F, the leftmost curve represents the clotting progress curve in the absence of the peptide and others appear from left to right with increasing peptide concentrations. In FIG. 17A, the concentrations of the hirudin peptide were 0 μM, 0.1 μM, 0.2 μM, 0.5 μM, 0.7 μM and 1.0 μM, respectively. In FIG. 17B, the peptide concentrations of FN22 were 0 μM, 0.04 μM, 0.08 μM, 0.12 μM, 0.2 μM, 0.4 μM, 0.8 μM and 1.0 μM, respectively. In FIG. 17C, the peptide concentrations of FD22 were 0 μM, 0.01 μM, 0.02 μM, 0.04 μM, 0.08 μM, 0.1 μM, 0.3 μM and 0.5 μM, respectively. In FIG. 17D, the peptide concentrations of Hirulog (also called bivalirudin, FIG. 1) were 0 nM, 1.35 nM, 2.7 nM, 13.5 nM and 27 nM, respectively.

In FIG. 17E, in the absence of the peptides, the onset of the clotting time for all assays is around 75 s. The peptide concentration for doubling the clotting time (DCT) was defined as the $IC_{50}$ value. The $IC_{50}$ value of each peptide was determined by the peptide concentration when the clotting time was 150 s and is listed in FIG. 1 and Table 1.

TABLE 1

Inhibitory activities of the FX22 peptides containing $P_4$-$P_1$ tetrapeptides

| Peptide Inhibitor | Sequence | Clotting assay, 37° C. (IC50, nM) | Amidolytic assay, 25° C. (Ki, nM) |
|---|---|---|---|
| Hirudin[54-65] | GDFEEIPEEYLQ (SEQ ID NO:10) | 447 ± 14 | >2000 |
| FN | FNPRP (SEQ ID NO:11) | >100000 | >2000 |
| FN22[a] | FNPRPQSHNDGDFEEIPEEYLQ (SEQ ID NO:12) | 150 ± 15 | 100 ± 10 |
| FD22[a] | FDPRPQSHNDGDFEEIPEEYLQ (SEQ ID NO:13) | 50 ± 15 | 55 ± 10 |
| FN22 | FNPRPQSHNDGDFEEIPEEYLQ (SEQ ID NO:12) | 67 ± 5 | 80 ± 10 |
| FD22 | FDPRPQSHNDGDFEEIPEEYLQ (SEQ ID NO:13) | 45 ± 8 | 48 ± 4 |
| FE22 | FEPRPQSHNDGDFEEIPEEYLQ (SEQ ID NO:14) | 80 ± 5 | ND |
| FH22 | FHPRPQSHNDGDFEEIPEEYLQ (SEQ ID NO:15) | >150[b] | ND |
| FD22-D | FDPRPQDHNDGDFEEIPEEYLQ (SEQ ID NO:16) | 53 ± 2 | 58 ± 3 |
| FE22-D | FEPRPQDHNDGDFEEIPEEYLQ (SEQ ID NO:17) | >125[b] | ND |
| FD22-H | FDPRPQHHNDGDFEEIPEEYLQ (SEQ ID NO:18) | 70 ± 6 | ND |
| FD22-K | FDPRPQKHNDGDFEEIPEEYLQ (SEQ ID NO:19) | 60 ± 5 | ND |
| FD22-R | FDPRPQRHNDGDFEEIPEEYLQ (SEQ ID NO:20) | 32 ± 4 | 45 ± 6 |
| WD22-R | WDPRPQRHNDGDFEEIPEEYLQ (SEQ ID NO:21) | 22 ± 3 | 17 ± 5 |
| WD22-R-P | WDPRPQRHNDGDFEPIPEEYLQ (SEQ ID NO:22) | 6.7 ± 2.0 | 171 ± 12[c] |
| WD22-R-YP | WDPRPQRHNDGDYEPIPEEYLQ (SEQ ID NO:23) | 4.5 ± 2 | 358 ± 23[c] |

TABLE 1-continued

Inhibitory activities of the FX22 peptides containing P$_4$-P$_1$ tetrapeptides

| Peptide Inhibitor | Sequence | Clotting assay, 37° C. (IC50, nM) | Amidolytic assay, 25° C. (Ki, nM) |
|---|---|---|---|
| WD22-R-P[d] | WDPRPQRHNDGDFEPIPEEYLQ (SEQ ID NO:22) | 8.1 ± 1.1 | ND |
| WD22-R-YP[d] | WDPRPQRHNDGDYEPIPEEYLQ (SEQ ID NO:23) | 4.8 ± 0.8 | ND |
| WD22-SR-P | WDPRPQSRNDGDFEPIPEEYLQ (SEQ ID NO:24) | 53 ± 2 | ND |
| WD22-SR-YP | WDPRPQSRNDGDYEPIPEEYLQ (SEQ ID NO:25) | 32 ± 3 | ND |
| WD22-L-P | WDPRPQLHNDGDFEPIPEEYLQ (SEQ ID NO:31) | 26 ± 3 | 39 ± 4 |
| FD21-4GN | FDPRPGGGGCNGDFEEIPEEYL (SEQ ID NO:33) | 208 ± 8 | 300 ± 20 |
| FN22-I | FNPRPQIHNDGDFEEIPEEYLQ (SEQ ID NO:26) | 45 ± 1 | 360 ± 10 |
| IQ22-I | IQPRPQIHNDGDFEEIPEEYLQ (SEQ ID NO:27) | 39 ± 3 | 49 ± 7 |
| GS-AV22-I | GSAVPRPQIHNDGDFEEIPEEYLQ (SEQ ID NO:28) | 33 ± 1 | 41 ± 2 |
| FQ22-M | FQPRPQMHNDGDFEEIPEEYLQ (SEQ ID NO:29) | 11 ± 1 | 64 ± 4 |
| GS-IQ22-I | GSIQPRPQIHNDGDFEEIPEEYLQ (SEQ ID NO:30) | 10 ± 1 | >400 |
| LD22 | LDPRPQSHNDGDFEEIPEEYLQ (SEQ ID NO:32) | 228 ± 7 | 260 ± 8 |
| Hirulog | dFPRPGGGGNGDFEEIPEEYL | 2.5 ± 0.5 | 2.6 ± 1.3 |
| Hirulog[e] | dFPRPGGGGNGDFEEIPEEYL | | 2.3 |
| P53[e] | dFPRPQSHNDGDFEEIPEEYL | 4.1 ± 0.8 | 2.8 ± 0.9 |

Figure 22:
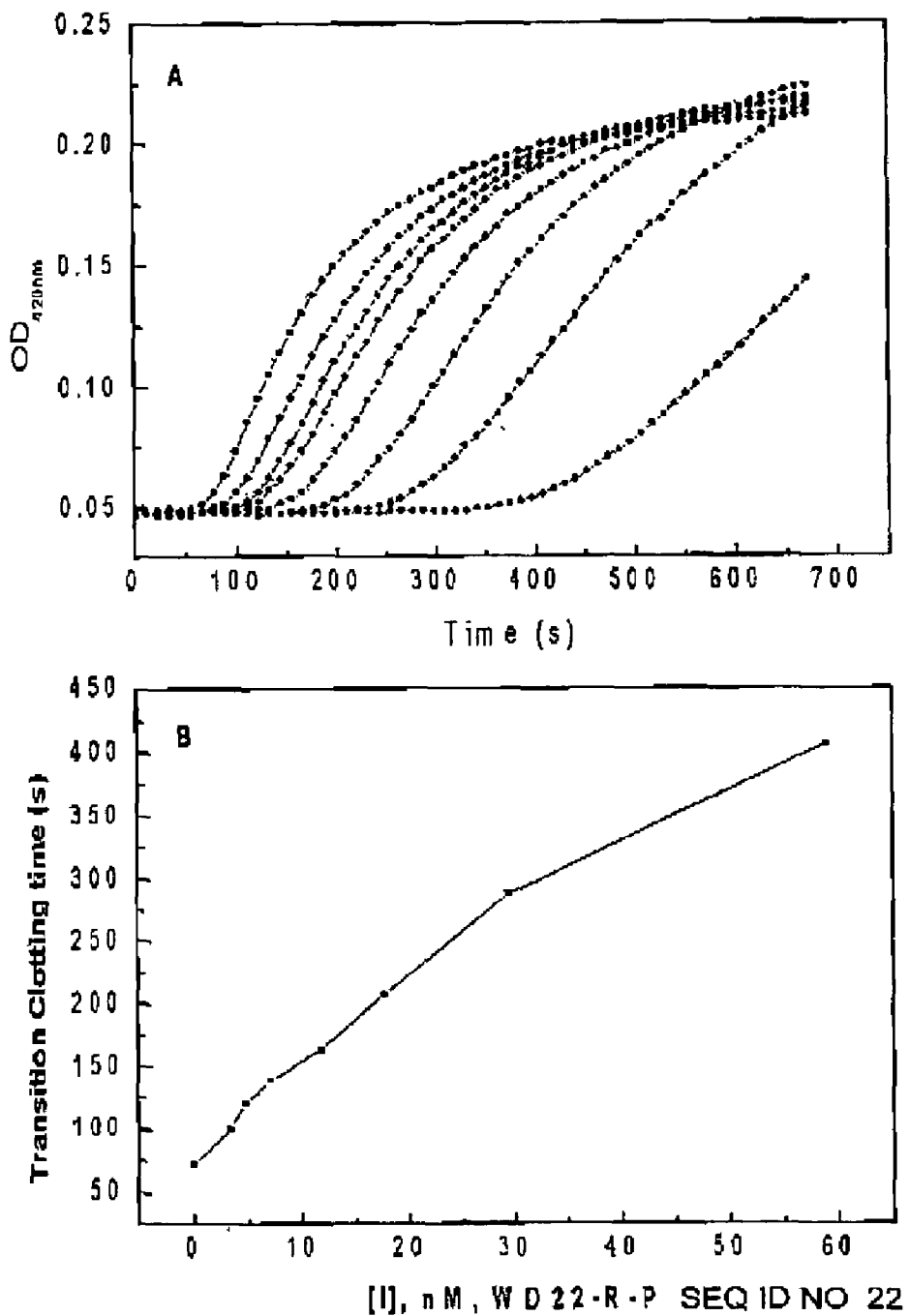
FIG. 22A illustrates inhibition curves of thrombin by recombinant WD22-R-P (SEQ ID NO:22) at various increasing peptide concentrations.
FIG. 22B illustrates the transition clotting time as a function of the peptide concentration for recombinant WD22-R-P (SEQ ID NO:22)
Figure 23:
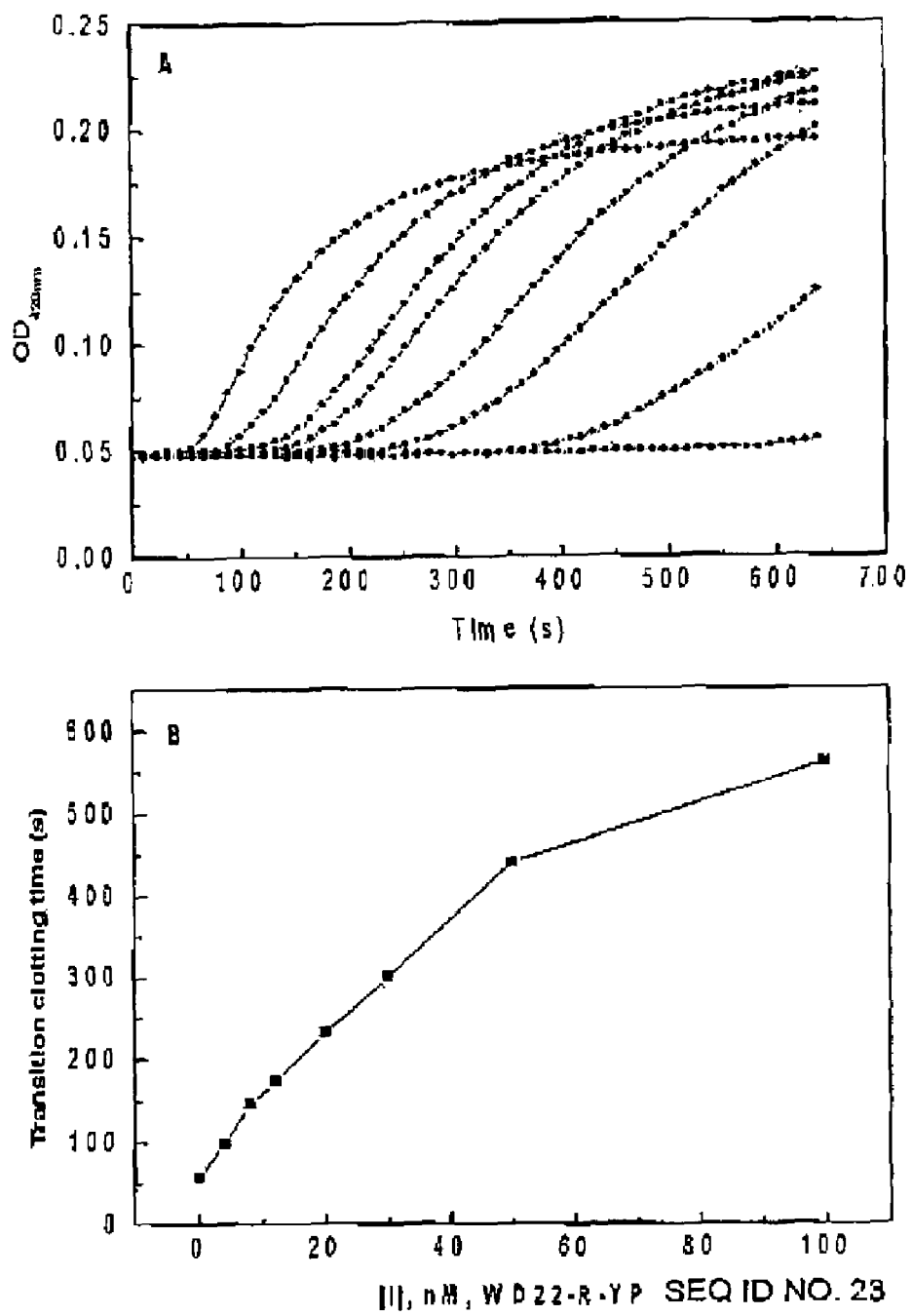
FIG. 23A illustrates inhibition curves of thrombin by recombinant WD22-R-YP (SEQ ID NO:23) at various increasing peptide concentrations.
FIG. 23B illustrates the transition clotting time as a function of the peptide concentration for recombinant WD22-R-YP (SEQ ID NO:23).

[a] These two peptides were prepared by use of a recombinant DNA procedure (see FIGS. 2-6, 15A, 15B and 16A).
[b] No delay in clotting time up to the peptide concentrations shown
[c] The K$_i$ values shown were determined based on competitive inhibition achieved when the inhibitor concentrations were larger than 20 nM. If [I] <20 nM, the kinetics data followed a behavior of non-competitive inhibition.
[d] These two peptides were prepared by use of a recombinant DNA procedure (see FIG. 16A). Their anticoagulant activities are shown in FIGS. 22 and 23.
[e] Data from the published reports of DiMaio (supra) and Maraganore (supra).

The FN22 peptide also inhibited α-thrombin-catalysed hydrolysis of the chromogenic substrate, Tos-Gly-Pro-Arg-p-nitroanilide, at submicromolar concentrations (Table 1). Under the same experimental conditions, micromolar concentrations of the hirudin tail peptide exhibited no measurable inhibition of thrombin-catalyzed substrate turnover (Table 1). Likewise, the presence of the FNPRP pentapeptide (SEQ IS NO:11) at concentrations as high as 100 µM, exhibited no significant inhibition.

These observations indicated that at micromolar concentrations, the individual components of FN22, i.e. the active site- and the FRE-directed moieties, were unable by themselves to inhibit the thrombin hydrolysis of the tripeptide substrate. In contrast, the combination of these components in a single polypeptide as in FN22 resulted in potent inhibition of the thrombin active site.

The inhibition constant (K$_i$) of the FN22 peptide was then determined at substrate concentrations near the K$_M$ of the substrate for human α-thrombin (K$_M$=4.2 µM). Interestingly, the inhibition by FN22 was found to be competitive, which showed a K$_i$ of ~100 nM (Table 1). In the presence of the FN22 peptide at 80 µM, the K$_M$ for thrombin-catalyzed hydrolysis of the chromogenic substrate increased from 4.2 µM to 6.4 µM and the k$_{cat}$ decreased from 130 to 115 s$^{-1}$.

The FN22 peptide was incubated with thrombin at 25° C. in order to investigate the stability of the peptide in complex with thrombin. The progress of peptide cleavage by thrombin was monitored and analyzed through the HPLC profiles of the FN22 peptide in the absence or presence of thrombin for different incubation times. It was found that about 30% of the peptide was cleaved by thrombin after 40 hours (FIG. 18A). In the clotting assay, the FN22 peptide at a concentration of 400 nM was premixed with thrombin for different times of incubation before initiating the clotting reaction. The cleavage of the peptide by thrombin is indicated by a reduced clotting time with increasing incubation times. After 30 hrs of incubation, the clotting time was reduced by 41% compared to the control (FIG. 18C).

In both FIGS. 18A and 18B, the retention time for the intact peptides was 23.0 min. The large fragment produced from cleavage of the peptides by thrombin (at the $Arg_{47}$-$Pro_{48}$ bond, FIG. 15A) was eluted slightly earlier than the intact peptides, which appeared as a shoulder of the HPLC peak of the undigested peptide.

In FIG. 18C, curve (1) represents the clotting assay curve recorded for a freshly-prepared stock solution of thrombin in the absence of peptide inhibitors, curves (2) and (3) represent the clotting curves recorded under the same condition as in (1) except that thrombin stood at 4° C. and 25° C., respectively, for 30 hrs, curves (4) and (5) represent the clotting curves recorded under the same condition as that in (3) except that the FN22 peptide (400 nM, curve 4) and FD22 (100 nM, curve 5) were mixed with thrombin during incubation, and curves (6) and (7) represent the clotting curves recorded under the same condition as that in (3) except that FN22 (400 nM, curve 6) and FD22 (100 nM, curve 7) were freshly-prepared intact peptides.

2: Asp Residue at the P3 Site Confers Enhanced Bivalency for Thrombin Binding

The inventors then studied whether a charged residue at the $P_3$ site would enhance the inhibition of a substituted FN22 peptide to human thrombin. The replacement by negatively charged residues was first considered (e.g. Asp), as an Asp residue at this site is unfavourable for peptide cleavage (Le Bonniec, B. F. and Esmon, C. T. (1991) Proc. Natl. Acad. Sci. U.S.A. 88, 7371-7375). Even so, an Asp at the $P_3$ site can still confer binding to the thrombin active site as shown for the LDPR sequence (SEQ ID NO:1) (Ni, F., Ripoll, D. R., and Purisima, E. O. (1992) Biochemistry 31, 2545-2554). The new bivalent peptide, referred to as FD22, was prepared by use of the same recombinant procedure as for the FN22 peptide (FIGS. 3, 6, 16A & 16B). FIG. 16D shows the $^1H$-$^{15}N$ NMR heteronuclear single-quantum correlation (HSQC) spectrum of the $^{15}N$-labelled FD22 peptide. The narrow proton chemical shift dispersion (~1 ppm, FIG. 16D) indicates that the FD22 peptide lacks a folded structure in solution, as shown previously for related peptides (DiMaio, J., Ni, F., and Konishi, Y. Thrombin inhibitors based on the amino acid sequence of hirudin. [2,085,465]. 2001. Canadian. 14-6-1991). Clotting assay showed that FD22 had a stronger inhibition of thrombin compared to FN22 (FIGS. 9, 17C and Table 1), with an $IC_{50}$ of ~50 nM (at 37° C.) and $K_i$ values of ~55 nM at 25° C.

Compared to FN22, the FD22 peptide is much more stable against thrombin cleavage. After the peptide was incubated with thrombin at 25° C. for 40 hrs, around 90% of the intact FD22 peptide still remained as shown by use of HPLC analysis (FIG. 18B). In the clotting assay, the FD22 peptide at 100 nM was premixed with thrombin for different times before initiation of clotting. The peptide thus prepared had the clotting time reduced by only 12% after 30 hrs of incubation with thrombin. Indeed, the $^{15}N$-labelled FD22 with a concentration of ~1 mM (FIG. 16D) was digested completely at the $Arg(P_1)$-$Pro(P_1')$ bond by a 5 µM concentration of human α-thrombin only after more than 60 hrs of incubation.

3: Nature of the $P_3$ and $P_3'$ residues and Effects on Thrombin Inhibition

The $P_3$ and $P_3'$ positions of the active-site binding sequence $Phe(P_4)$-$Asp(P_3)$-$Pro(P_2)$-$Arg(P_1)$-$Pro(P_1')$-$Gln(P_2')$-$Ser$ ($P_3'$) were then explored for their contributions to thrombin binding and inhibition by the bivalent peptide. For these experiments, both the FN22 and FD22 peptides and all other substituted ones (vide infra) were generated synthetically using solid-phase methods. The synthetic FN22 and FD22 peptides appear to have somewhat higher activities than the recombinant equivalents (FN22[a] and FD22[a] in Table 1). However, this can be understood as caused by the premixing of the substrates (chromogenic or fibrinogen) with the synthetic peptide inhibitors instead of pre-mixing of the recombinant peptides with thrombin (see FIGS. 7-10, 18C). These peptides should be slowly proteolyzed at the $Arg(P_1)$-$Pro(P_1')$ peptide bonds as shown herein (FIG. 18C) and for the P53 and Hirulog peptides in previous studies (DiMaio, J., Gibbs, B., Munn, D., Lefebvre, J., Ni, F., and Konishi, Y. (1990) J. Biol. Chem. 265, 21698-21703; and Witting, J. I., Bourdon, P., Brezniak, D. V., Maraganore, J. M., and Fenton, J. W. (1992) Biochem. J. 283 (Pt 3), 737-743).

Activities of the synthetic peptides were ranked by use of only the $IC_{50}$ (or DCT) values for the inhibition of fibrinogen clotting. Therefore, elongation of the negatively-charged side chain through the $Asp(P_3)$ to $Glu(P_3)$ substitution decreased the anticlotting activity of the bivalent peptide from an $IC_{50}$ of 45 nM (for FD22) to 80 nM (for FE22) (Table 1). The positively-charged and somewhat aromatic His residue at $P_3$ is not well tolerated, as the FH22 peptide had a further decreased anticlotting activity (Table 1). Interestingly, the $P_3'$ site appears to be insensitive to the presence of a negatively-charged residue, as the FD22-D peptide with a $Ser(P_3')$ to $Asp(P_3')$ substitution had a similar activity as the FD22 peptide. On the other hand, the FE22-D peptide had a significantly reduced activity (Table 1), indicating that an elongated and negatively-charged $Glu(P_3)$ is unfavourable when a negatively-charged Asp is present at the $P_3$ position.

The residue requirements at the $P_3'$ position were examined further by reversing the charge of the residue at this site. A His or a Lys residue is not as favourable as a Ser residue at $P_3'$ since both FD22-H and FD22-K had somewhat reduced activities compared to the FD22 peptide (Table 1). Very surprisingly, however, an $Arg(P_3')$ residue appears to confer enhanced anticlotting activity as the FD22-R peptide had an $IC_{50}$. Of ~32 nM compared to ~45 nM for the FD22 peptide (Table 1). Inhibition of the thrombin turnover of the chromogenic substrate Tos-Gly-Pro-Arg-pNA was then studied for the two bivalent peptides, FD22-D and FD22-R. Changes of $K_i$ values compared to that of FD22 reflect the impact of $P_3'$ modifications on binding to the thrombin active site. The FD22-R peptide with $Arg(P_3')$ had a similar $K_i$ as FD22 with $Ser(P_3')$ despite that FD22-R appears to be slightly more active ($IC_{50}$~32 nM) in the anticlotting assay. The FD22-D peptide with $Asp(P_3')$ had the largest $K_i$ value (or the least active) among the three, indicating that the negatively-charged Asp is not a favourable $P_3'$ residue.

4: Enhancement of Inhibitory Activities by a Trp Residue at the $P_4$ Site

The inventors then examined whether a Trp residue at the $P_4$ site would contribute positively to the anticoagulant activity of the bivalent peptide. Indeed, the WD22-R peptide with a $Trp(P_4)$ residue had its DCT value decreased almost 30% and its $K_i$ value decreased more then 50% compared to the FD22-R peptide (Table 1). A further change of Glu58 to Pro as well as the Phe56Tyr substitution within the exosite-binding segment led to another more than 50% drop in DCT for the WD22-R-P and WD22-R-YP peptides, respectively (Table 1). Interestingly, both the WD22-R-P and WD22-R-YP peptides had significantly increased $K_i$ values in the inhibition of the amidolytic activity of thrombin. These results indicate that the WD22-R-P and WD22-R-YP molecules represent a new class of anticoagulant agents with strong binding (low DCT values) to the fibrinogen-recognition exosite of thrombin, while interfering only partially the thrombin catalytic active site (with high $K_i$ values). Furthermore, the strong anticoagulant activities of WD22-R-P and WD22-R-YP appear to depend on the nature of the so-called linker sequence (FIG. 1 and FIG. 15A), as a shift of the Arg($P_3'$) residue to the $P_4'$ position led to almost a factor of 10 increase of the DCT values of both the WD22-SR-P and WD22-SR-YP peptides (Table 1). In addition, replacement of the important Arg($P_3'$) residue by Leu($P_3'$) resulted in a decreased anticoagulant activity of the WD22-L-P peptide (DCT ~26 nM) by almost 4 fold as compared to the WD22-R-P peptide (DCT ~6.7 nM) (Table 1). In all, these data showed that the strong anticoagulant activities of the WD22-R-P and WD22-R-YP molecules critically depend on the presence of an Arg residue at the $P_3'$ position with presumably specific interactions with the S'-subsites of the thrombin active site. The critical interdependence between the S-subsite binding residues, i.e. those up to Arg($P_1$) before the peptide bond cleaved by thrombin, and the S'-subsite binding residues (those after Arg($P_1$)) is also seen with the FD22 and FD21-4GN (also referred to as FD22.1 in FIG. 1) molecules. The Phe($P_4$)-Asp($P_3$)-Pro($P_2$)-Arg($P_1$)-Pro($P_1'$) (SEQ ID NO:122) pentapeptide segment confers synergistic binding between the active site and the exosite I of thrombin (with a DCT value of ~50 nM for FD22). However, replacement of residues QSHNDG (SEQ ID NO:123) in FD22 by the linker residues GGGGNG (SEQ ID NO:124) and the exosite-binding sequence by DFEEIPEEYL (SEQ ID NO:125) in hirulog resulted in more than 4 fold decrease of the anticoagulant activity (i.e. 4 times increase in the DCT value for the FD21-4GN peptide, Table 1).

5: Selection of Bivalent Peptide Inhibitors of Thrombin by Phage Display

Figure 19:
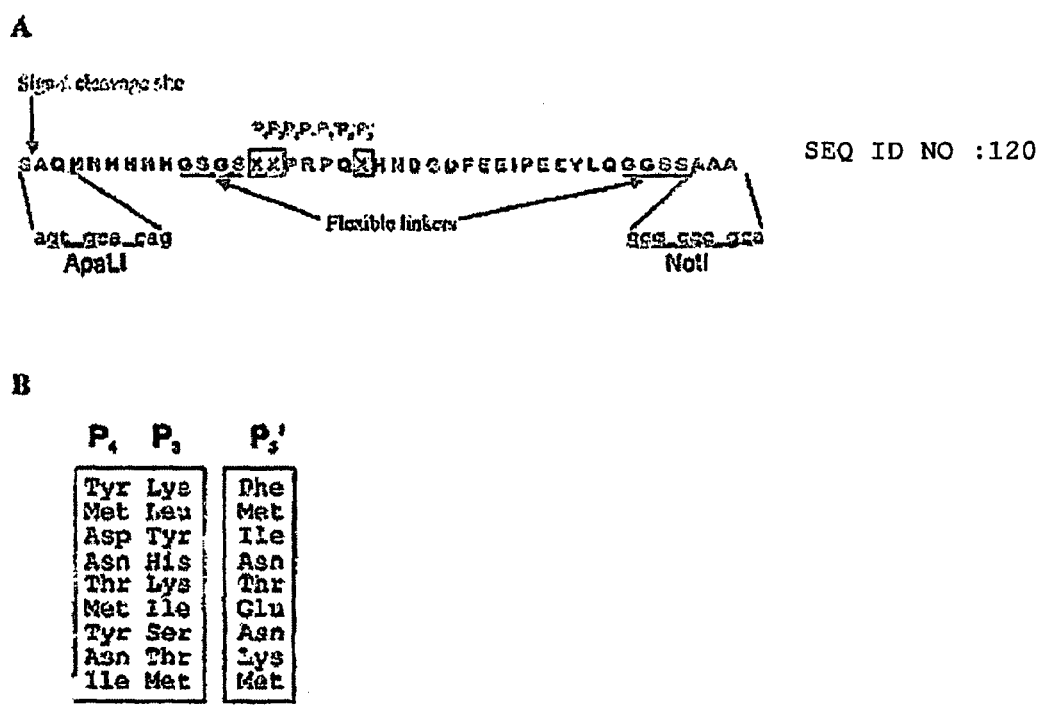
FIG. 19A illustrates the cloning sites as DNA sequences used for the construction of the phage-displayed bivalent peptide library.
FIG. 19B illustrates the sequences of nine randomly-selected clones from a small scale production of the phage library of FIG. 19A.
Figure 20:
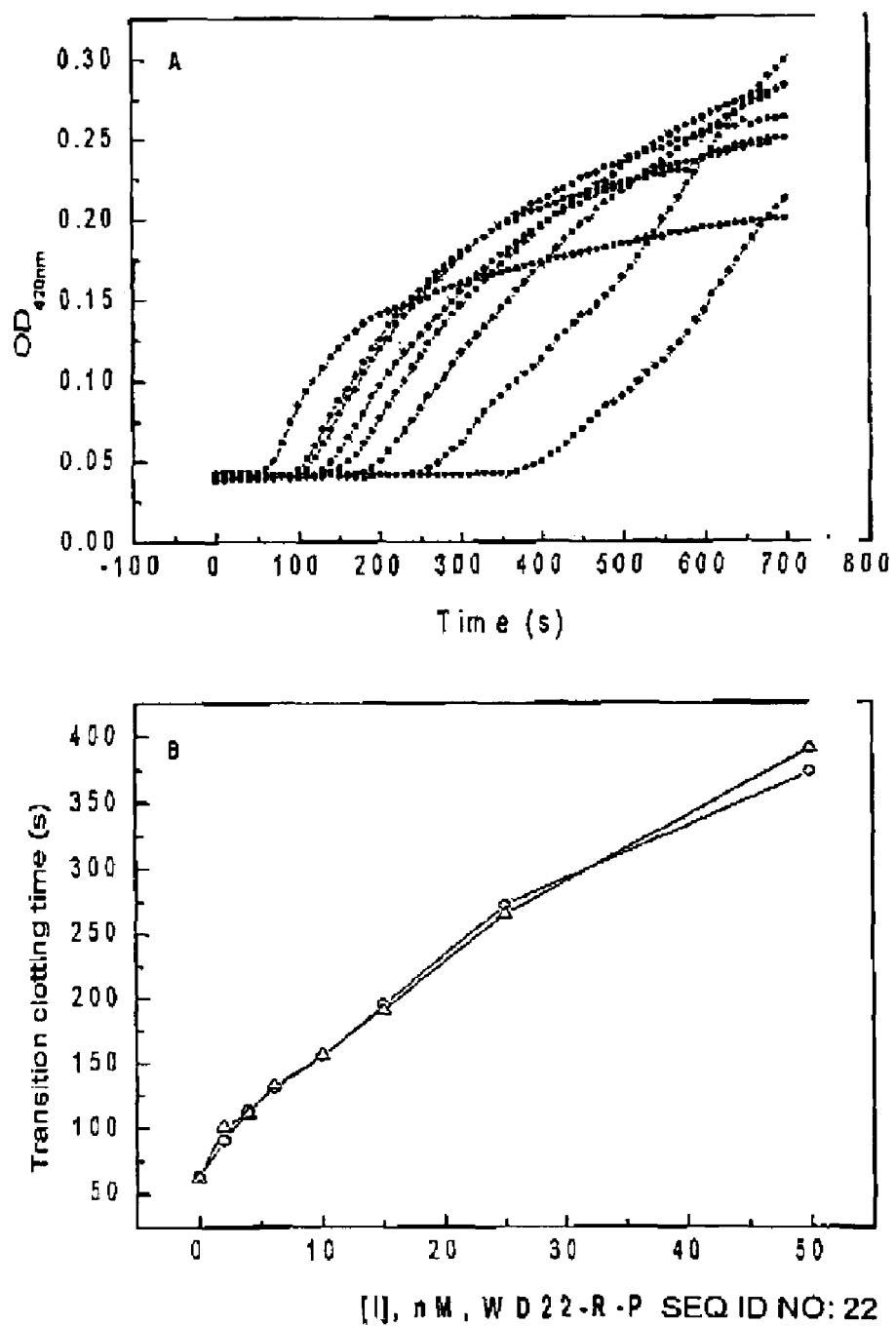
FIG. 20A illustrates inhibition curves of thrombin by synthetic WD22-R-P (SEQ ID NO:22) at various increasing peptide concentrations.
FIG. 20B illustrates the transition clotting time as a function of the peptide concentration for synthetic WD22-R-P (SEQ ID NO:22), wherein two independent sets of data are plotted therein.
Figure 21:
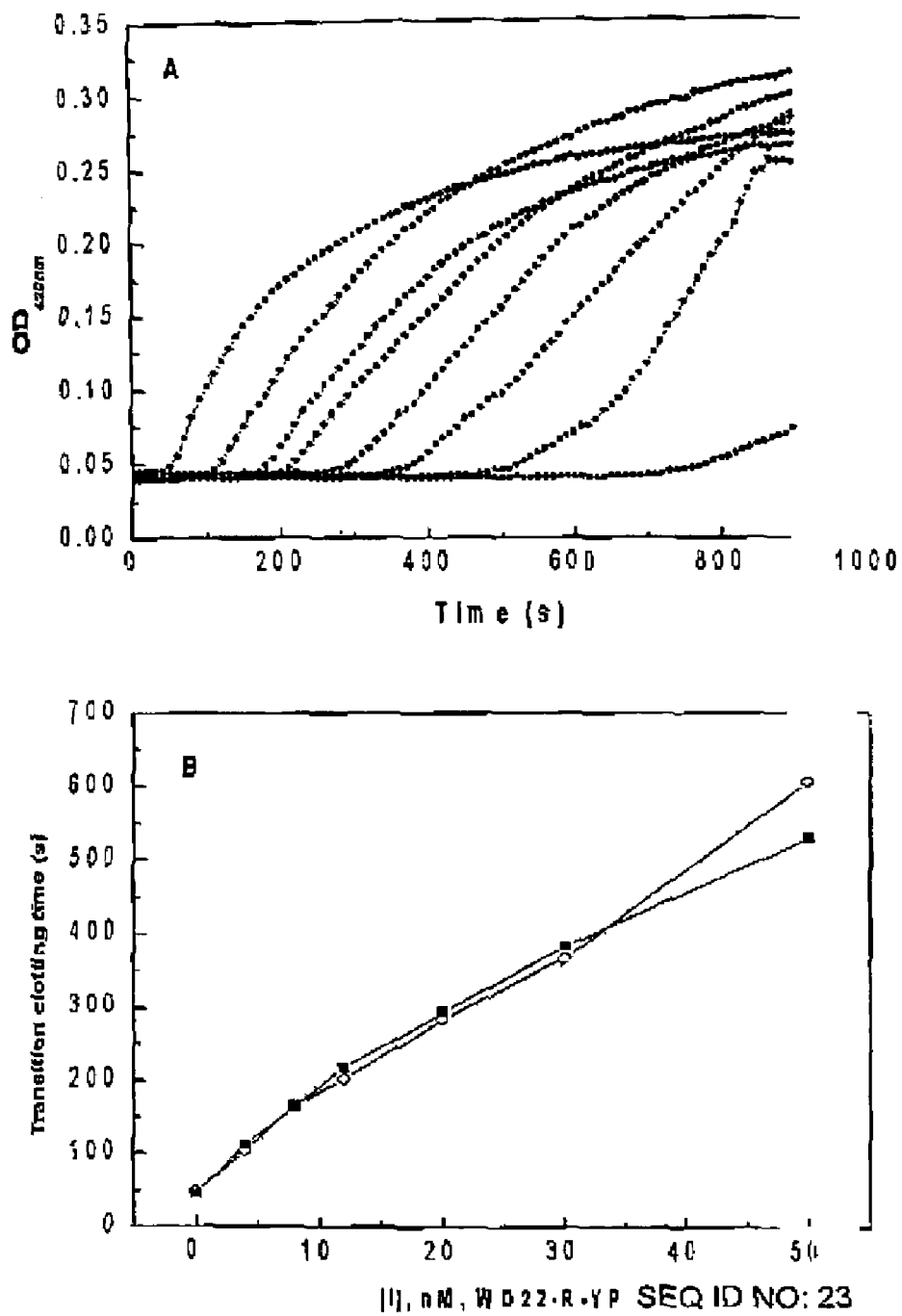
FIG. 21A illustrates inhibition curves of thrombin by synthetic WD22-R-YP (SEQ ID NO:23) at various increasing peptide concentrations.
FIG. 21B illustrates the transition clotting time as a function of the peptide concentration for synthetic WD22-R-YP (SEQ ID NO:22), wherein two independent sets of data are plotted therein.

Residue preferences at the $P_4$, $P_3$, and $P_3'$ sites were then searched through sequences displayed on phages and panning the displayed, peptide library. The framework of the peptide library (FIG. 19A) includes two flexible linkers of glycine/serine residues to separate the displayed peptide ligand from the His-tag and the gill protein. These Gly/Ser linkers were introduced to minimize possible interference with thrombin binding. Sequencing of ten clones randomly chosen showed the lack of a noticeable sequence bias (FIG. 19B). Three slightly different protocols were used for phage selection. In the first approach, the phage particles were incubated at 37° C. with active thrombin, followed by purification using Ni-NTA affinity resin of the phages containing uncleaved sequences. The amount of added thrombin was chosen empirically to retain 10-50% of the intact phages. The collected phage was amplified and panned against active thrombin immobilized on a solid support. Only two sequences were identified after these two steps of selection (Table 2).

In FIG. 19A, underlined are the inserted flexible linkers of Gly/Ser residues, which were introduced to minimize interference with thrombin binding to the displayed peptide. Boxed are randomized amino acids, with putative subsite positions displayed on top.

TABLE 2

Sample sequences of retained phages after the first round of selection

Sequence framework of phage-displayed peptides
(SEQ ID NO:34)

...HHHHHHGSGS X X P R P Q X HNDGDFEEIPEEYLQGGSS...

(positions: $P_4$ $P_3$ $P_2$ $P_1$ $P_1'$ $P_2'$ $P_3'$)

| (A) thrombin cleavage + panning at 25° C. | | | (B) panning at 4° C. | | | (C) panning at 25° C. | | |
|---|---|---|---|---|---|---|---|---|
| $P_4$ | $P_3$ | $P_3'$ | $P_4$ | $P_3$ | $P_3'$ | $P_4$ | $P_3$ | $P_3'$ |
| Thr | Phe | Pro | Phe | Asn | Ile | His | Val | Leu |
| Asn | Val | Ala | Phe | Gln | Met | His | Thr | Gln |
|  |  |  | Tyr | Asn | Ile | Leu | Met | Ser |
|  |  |  | His | Tyr | Ile | Ile | Asn | Met |
|  |  |  | His | Tyr | Thr | Val | Thr | Pro |
|  |  |  | His | Ala | Ser | Thr | Asp | Ile |
|  |  |  | Ile | Leu | Met | Pro | Glu | Leu |
|  |  |  | Leu | Thr | Ile | Gly | Asn | Tyr |
|  |  |  | Asn | Thr | Phe |  |  |  |
|  |  |  | Gln | Ser | Leu |  |  |  |

Phase selection was then carried out with less stringent cleavage conditions, i.e., no thrombin cleavage was performed before the phage panning. It was reasoned that upon binding to immobilized active thrombin, some cleavage would take place and therefore enrich propagated phages with the sequences possessing lower proteolytic susceptibility plus higher affinity. One round of panning was performed at room temperature (25° C.), another at 4° C., and the TG1 cells were infected with the retained phages directly in the panning well. For panning rounds carried out at 25° C. and 4° C., 60 and 4×10³ plaques were recovered, respectively. Peptide sequences were determined for eight and ten randomly-chosen phage particles from these two experiments (Table 2). A clear tendency of the $P_3'$ position was observed, with Ile/Leu/Met dominating the collected phages. In addition, $P_4$ is occupied preferentially by aromatic, heterocyclic or long-chain aliphatic amino acids. Interestingly, the rationally designed tetrapeptide sequence Phe-Asn-Pro-Arg (SEQ ID NO:3) was found in one of the clones obtained from panning at 4° C. (Table 2).

The phage particles collected after the first round of panning at 4° C. were amplified and used for a second round of panning, at two temperatures. A total of 2×10⁷ plaques and 3×10⁷ plaques were recovered at 25° C. and 4° C., respectively. The increase in phage recovery as compared to the first round of panning is consistent with amplification of sequences with higher affinity towards thrombin, while less dependence of phage recovery on temperature suggested decreased proteolytic cleavage. In the second round of selection, the $P_3'$ position retained its strong preference for Ile/Leu/Met amino acids (Table 2). The $P_3$ position showed a preference for Gln, while aromatic and heterocyclic amino acids at $P_4$ were outnumbered by long-chain aliphatic residues. Apparently, trivalent peptides may have been selected by the process of panning, with the invariant C-terminal hirudin-derived tail targeting the fibrinogen-recognition exosite, optimized prime-site sequences with Ile/Leu/Met in the $P_3'$ position, and the $P_1$-$P_4$ tetrapeptide sequences binding to the active site of thrombin.

6: Antithrombin Activities of Representative Peptides Selected from the Phage Library Five bivalent peptides were derived from two sequences obtained from the first round of panning (Table 2), and three sequences from the second round of selection (Table 3). The two peptides, FN22-I and FQ22-M, had a Phe residue at $P_4$, Gln or Asn at $P_3$ and Ile or Met at $P_3'$, which resemble the FNPR sequence (SEQ ID NO:3) of the prototypic peptide FN22 (FIG. 1, 15A and Table 1). The three peptides, GS-AV22-I, GS-IQ22-I and IQ22-I, from the second round had an Ala or Ile at $P_4$, Val or Gln at $P_3$ and Ile at $P_3'$, all of which are frequently occurring in the panning hits (Table 3). Two of the peptides, GS-AV22-I and GS-IQ22-I included the two residues Gly-Ser at the N-termini, in accordance with the context of phage-displayed sequences (FIG. 19A).

TABLE 3

Sample sequences of retained phages after the second round of selection

Sequence framework of phage-displayed peptides
(SEQ ID NO:34)

```
             P4 P3 P2 P1 P1' P2' P3'
...HHHHHHGSGS X  X  P  R  P   Q   X  HNDGDFEEIPEEYLQGGSS...
```

| $P_4$ | $P_3$ | $P_3'$ | $P_4$ | $P_3$ | $P_3'$ |
|---|---|---|---|---|---|
| (A) panning at 4° C. | | | (B) panning at 25° C. | | |
| Tyr | Ser | Ile | Tyr | Asn | His |
| Ile | Gln | Ile | Ile | Gln | Ile |
| Ile | Gln | Ile | Ile | Gln | Ile |
| Ile | Gln | Met | Ile | Leu | Met |
| Ile | Met | Met | Val | Gln | Pro |
| Ile | Ile | Met | Leu | Ile | Met |
| Ile | His | Met | Met | Gln | Met |
| Val | Gln | Gln | Met | Met | Met |
| Val | Met | Gln | Ala | Val | Ile |
| Leu | His | Leu | Ala | Val | Ile |
| Ala | Val | Ile | Ala | Ile | Gln |
| Ala | Leu | Ile | Ala | Ile | Pro |
| Ala | Leu | Ile | Ala | Gln | Ile |
| Ala | Met | Ala | Ala | Thr | Leu |
| Ala | Tyr | Ala | Ala | Thr | Val |
| Pro | Ile | Ile | Pro | Asn | Val |
| Pro | Ile | Ile | Asn | Asp | Lys |
| Pro | His | Ile | Asn | Ser | Leu |

TABLE 3-continued

Sample sequences of retained phages after the second round of selection

Sequence framework of phage-displayed peptides
(SEQ ID NO:34)

```
              P4 P3 P2 P1 P1' P2' P3'
...HHHHHHGSGS X  X  P  R  P   Q    X  HNDGDFEEIPEEYLQGGSS...
```

| P4 | P3 | P3' | P4 | P3 | P3' |
|---|---|---|---|---|---|
| (A) panning at 4° C. | | | (B) panning at 25° C. | | |
| Pro | Trp | Leu | | | |
| Thr | Ile | Ile | | | |

All five peptides displayed $IC_{50}$ values in the range of 10 to 45 nM (Table 1). However, they were, with the exception of IQ22-I, generally much less efficient at inhibiting the amidolytic activity of thrombin (Table 1). The significantly increased $K_i$ (with respect to $IC_{50}$ may reflect less efficient binding and/or the existence of additional binding modes of these peptides near the active site of thrombin as observed with some peptides in the WD22 series (Table 1). Regardless, these bivalent peptides derived from the phage library exhibit potent inhibition of fibrinogen clotting catalyzed by thrombin, in accordance with the phage selection process. The FQ22-M and the GS-IQ22-I peptides with sequences of Phe($P_4$)-Gln($P_3$)-Pro-Arg-Pro-Gln-Met($P_3'$) (SEQ ID NO:35) and Gly-Ser-Ile($P_4$)-Gln($P_3$)-Pro-Arg-Pro-Gln-Ile($P_3'$) (SEQ ID NO:36), respectively, even had $IC_{50}$ values down to 10 nM, that approaches the inhibitory potencies of other bivalent thrombin inhibitors such as hirulog or $P_{53}$ (DiMaio, J., Gibbs, B., Munn, D., Lefebvre, J., Ni, F., and Konishi, Y. (1990) *J. Biol. Chem.* 265, 21698-21703; and Maraganore, J. M., Bourdon, P., Jablonski, J., Ramachandran, K. L., and Fenton, J. W. (1990) *Biochemistry* 29, 7095-7101).

Finally, the LD22 peptide was synthesized, whereby the Phe($P_4$) residue of FD22 was replaced by Leu($P_4$). The LD22 peptide is related to the Hirulog-like peptide (HLP) reported by Shen at al (Xue, M., Ren, S., Welch, S., and Shen, G. X. (2001) *J. Vasc. Res.* 38, 144-152) in that it also contained the $P_1$-$P_4$ tetrapeptide LDPR (SEQ ID NO:1) from the thrombin receptor (Ni, F., Ripoll, D. R., and Purisima, E. O. (1992) *Biochemistry* 31, 2545-2554). However, this peptide had significantly-reduced antithrombin and anticoagulant activities (Table 1) in accordance with observations with the Hirulog-like peptide (Xue, M., Ren, S., Welch, S., and Shen, G. X. (2001) *J. Vasc. Res.* 38, 144-152).

Discussion

The specificities of substrate recognition by thrombin are commonly analyzed at the $P_1$, $P_2$ and $P_3$ subsites using a tripeptide sequence framework (Liu, L. W., Vu, T. K., Esmon, C. T., and Coughlin, S. R. (1991) *J. Biol. Chem.* 266, 16977-16980; Le Bonniec, B. F. and Esmon, C. T. (1991) *Proc. Natl. Acad. Sci. U.S.A.* 88, 7371-7375; Vindigni, A., Dang, Q. D., and Di Cera, E. (1997) *Nat. Biotechnol.* 15, 891-895; and Le Bonniec, B. F., MacGillivray, R. T., and Esmon, C. T. (1991) *J. Biol. Chem.* 266, 13796-13803). Optimal binding interactions with thrombin occur only if these tripeptide substrates contain an amino acid residue in the (D)-configuration, such as (d)Phe at $P_3$ (Blomback, B., Blomback, M., Olsson, P., Svendsen, L., and Aberg, G. (1969) *Scand. J. Clin. Lab Invest Suppl* 107, 59-61), which mimics the natural $P_9$ residue in FpA (Ni, F., Meinwald, Y. C., Vasquez, M., and Scheraga, H. A. (1989) *Biochemistry* 28, 3094-3105; Stubbs, M. T., Oschkinat, H., Mayr, I., Huber, R., Angliker, H., Stone, S. R., and Bode, W. (1992) *Eur. J. Biochem.* 206, 187-195; and Martin, P. D., Robertson, W., Turk, D., Huber, R., Bode, W., and Edwards, B. F. (1992) *J. Biol. Chem.* 267, 7911-7920). However, these minimalistic peptide substrates probe only the active site apparatus of thrombin and related binding events, which were found to be mildly sensitive to interactions of thrombin with regulatory proteins (Liu, L., W., Vu, T. K., Esmon, C. T., and Coughlin, S. R. (1991) *J. Biol. Chem.* 266, 16977-16980). On the other hand, cleavages after tetrapeptide sequences by thrombin, e.g. VDPR (SEQ ID NO:37) in human protein C, LDPR (SEQ ID NO:1) in human PAR1 and ISPR (SEQ ID NO:38) in the thrombin-activatable fibrinolysis inhibitor, are dramatically enhanced by binding interactions at thrombin exosites remote from the active site (Le Bonniec, B. F. and Esmon, C. T. (1991) *Proc. Natl. Acad. Sci. U.S.A.* 88, 7371-7375; Le Bonniec, B. F., MacGillivray, R. T., and Esmon, C. T. (1991) *J. Biol. Chem.* 266, 13796-13803; Schneider, M., Nagashima, M., Knappe, S., Zhao, L., Morser, J., and Nesheim, M. (2002) *J. Biol. Chem.* 277, 9944-9951; Boffa, M. B., Bell, R., Stevens, W. K., and Nesheim, M. E. (2000) *J. Biol. Chem.* 275, 12868-12878; and Ishii, K., Gerszten, R., Zheng, Y. W., Welsh, J. B., Turck, C. W., and Coughlin, S. R. (1995) *J. Biol. Chem.* 270, 16435-16440). Based on NMR and structural studies, it was found that binding specificity at the active site of thrombin may be captured by minimally a four-residue consensus motif, Phe($P_4$)-Xaa($P_3$)-Pro($P_2$)-Arg($P_1$) or FXPR (SEQ ID NO:39), where the $P_3$ residue (i.e. Xaa) can be a charged or a neutral polar residue contacting specific structural features of the $S_1$-$S_4$ subsites (Ni, F., Zhu, Y., and Scheraga, H. A. (1995) *J. Mol. Biol.* 252, 656-671). It was also found that the FXPR (SEQ ID NO:39) tetrapeptide sequences could be good candidates for active site binding in designing novel bivalent peptide inhibitors of thrombin (Song, J. and Ni, F. (1998) *Biochem. Cell Biol.* 76, 177-188), that are composed of only [L]-amino acids.

Indeed, both the FNPR (SEQ ID NO:3) and FDPR (SEQ ID NO:4) sequence motifs turned out to confer bivalent and bridge binding, as the peptides FN22 and FD22 had significantly enhanced anticlotting activities compared to the hirudin peptide that bind only to the fibrinogen recognition exosite of thrombin (Table 1). The FN22 peptide was also found to be cleaved by thrombin at the Arg($P_1$)-Pro($P_1'$) peptide bond as with all substrate-type bivalent inhibitors like $P_{53}$ or Hirulog (DiMaio, J., Gibbs, B., Munn, D., Lefebvre, J., Ni, F., and Konishi, Y. (1990) *J. Biol. Chem.* 265, 21698-21703; and Maraganore, J. M., Bourdon, P., Jablonski, J., Ramachandran, K. L., and Fenton, J. W. (1990) *Biochemistry* 29, 7095-

7101). In addition, thrombin can cleave much more efficiently (>50 fold) recombinant fusion proteins containing the FNPR (SEQ ID NO:3) sequence in place of the commonly-used LVPR sequence (SEQ ID NO:40). Screening combinatorial substrate libraries containing the $P_1$-$P_4$ tetrapeptides has confirmed thrombin's preference for a Pro($P_2$) residue and Phe or long-chain aliphatic residues at the $P_4$ position (Backes, B. J., Harris, J. L., Leonetti, F., Craik, C. S., and Ellman, J. A. (2000) Nat. Biotechnol. 18, 187-193; Edwards, P. D., Mauger, R. C., Cottrell, K. M., Morris, F. X., Pine, K. K., Sylvester, M. A., Scott, C. W., and Furlong, S. T. (2000) Bioorg. Med. Chem. Lett. 10, 2291-2294; nd Furlong, S. T., Mauger, R. C., Strimpler, A. M., Liu, Y. P., Morris, F. X., and Edwards, P. D. (2002) Bioorg. Med. Chem. 10, 3637-3647). On the other hand, the $P_3$ subsite was found to be rather promiscuous with both Asn and Asp among the least preferred residues for substrate cleavage. Even so, substitution of Asn($P_3$) for Asp($P_3$) led to an enhancement of the anticlotting activity of the FD22 peptide as well as a significant decrease of the proteolytic sensitivity to thrombin. This latter observation is very much in line with the notion that a $P_3$ aspartate in protein C partially inhibits the proteolytic cleavage at the VDPR (SEQ ID NO:37) site by thrombin (Le Bonniec, B. F. and Esmon, C. T. (1991) Proc. Natl. Acad. Sci. U.S.A. 88, 7371-7375; Ishii, K., Gerszten, R., Zheng, Y. W., Welsh, J. B., Turck, C. W., and Coughlin, S. R. (1995) J. Biol. Chem. 270, 16435-16440; and Rezaie, A. R. and Esmon, C. T. (1994) Eur. J. Biochem. 223, 575-579). In addition, enhanced inhibition of the FD22 peptide with Asp($P_3$) unfavorable for substrate turnover indicates that residue preferences for efficient catalysis may be too stringent a criterion for the selection of optimized binding interactions.

Using extended peptide substrates, it was shown previously that thrombin prefers a positively-charged residue, e.g. a lysine, at the $P_3'$ position over negatively-charged residues (Le Bonniec, B. F., Myles, T., Johnson, T., Knight, C. G., Tapparelli, C., and Stone, S. R. (1996) Biochemistry 35, 7114-7122). Interestingly, a Ser($P_3'$) to Asp($P_3'$) substitution resulted in little changes of the inhibitory activities of the FD22-D peptide, indicating that the thrombin active site can also tolerate negatively-charged aspartates at both the $P_3$ and $P_3'$ positions, at least for inhibitory binding. However, a further change of Asp($P_3$) to Glu($P_3$) impaired active site binding as the FE22-D peptide showed diminished anticlotting activities to a level approaching the hirudin peptide alone (Table 1). On the other hand, the bivalent peptide with an aspartate at $P_3$ indeed accommodates well a large and positively charged residue at the $P_3'$ position, as both the FD22-K and FD22-R peptides had comparable or higher inhibitory activities compared to FD22 (Table 1). With an arginine at the $P_3$ position, the FD22-R peptide showed a somewhat enhanced anticlotting activity as compared to the FD22 and FD22-D peptides (Table 1) with Ser($P_3'$) and Asp($P_3'$), respectively. Furthermore, the Arg residue at the $P_3'$ position may create a more favorable binding environment for the Asp($P_3$) residue as the FD22-R peptide showed the strongest inhibition (or lowest $K_i$) of the thrombin active site (Table 1). These findings indicate that there exist intricate communications between the $P_3$ and $P_3'$ sites not only through charge-charge interactions, but as well with defined spatial requirements as shown in studies of protein C activation by thrombin (Le Bonniec, B. F. and Esmon, C. T. (1991) Proc. Natl. Acad. Sci. U.S.A. 88, 7371-7375; Rezaie, A. R. and Esmon, C. T. (1994) Eur. J. Biochem. 223, 575-579; Le Bonniec, B. F., Guinto, E. R., and Esmon, C. T. (1992) J. Biol. Chem. 267, 6970-6976; and Rezaie, A. R. and Yang, L. (2003) Proc. Natl. Acad. Sci. U.S.A. 100, 12051-12056). The three-dimensional structures of an uncleavable analogue of human FpA containing $P_1'$-$P_3'$ residues (Martin, P. D., Malkowski, M. G., DiMaio, J., Konishi, Y., Ni, F., and Edwards, B. F. (1996) Biochemistry 35, 13030-13039) and of heparin cofactor II (Baglin, T. P., Carrell, R. W., Church, F. C., Esmon, C. T., and Huntington, J. A. (2002) Proc. Natl. Acad. Sci. U.S.A. 99, 11079-11084) in complexes with thrombin showed that the $P_3'$ residue projects its side-chain in the direction of the $P_3$ site, bringing both residues into side-chain to side-chain contacts. Such specific interactions would account for the enhanced anticlotting activity of the FD22-R peptide containing Asp($P_3$) and Arg($P_3'$) residues.

Complementary to rational design, panning of a phage library revealed additional bivalent sequences with unique $P_4$, $P_3$ and $P_3'$ residues (Tables 2 and 3). Phage libraries displaying bivalent peptides have recently been used for the discovery of specific inhibitors of factor VIIa (Maun, H. R., Eigenbrot, C., and Lazarus, R. A. (2003) J. Biol. Chem. 278, 21823-21830). A peptide with a defined sequence targeting an exosite of factor VIIa was used as an anchor for a bivalent and partially randomized peptide. The panning was to select peptide sequences capable of reaching and binding to the catalytic active site of factor VIIa, thereby undergoing proteolytic cleavage. The new panning procedure described herein, on the other hand, selects peptide sequences that bind strongly to thrombin and are resistant to proteolysis in the presence of thrombin. The $P_4$ site of the panned phage sequences had a preference for a hydrophobic or an aromatic residue, such as Ile/Leu, Phe or Tyr, in agreement with screening of substrate libraries (Backes, B. J., Harris, J. L., Leonetti, F., Craik, C. S., and Ellman, J. A. (2000) Nat. Biotechnol. 18, 187-193; Edwards, P. D., Mauger, R. C., Cottrell, K. M., Morris, F. X., Pine, K. K., Sylvester, M. A., Scott, C. W., and Furlong, S. T. (2000) Bioorg. Med. Chem. Lett. 10, 2291-2294; and Furlong, S. T., Mauger, R. C., Strimpler, A. M., Liu, Y. P., Morris, F. X., and Edwards, P. D. (2002) Bioorg. Med. Chem. 10, 3637-3647). The $P_3$ site was a great deal more variable, having either hydrophobic or polar residues such as Asn and Gln. The high occurrence of a long-chain hydrophobic residue, i.e. Leu/Met/Ile, at the $P_3'$ position (Tables 2 and 3) was not noted in previous studies using extended peptide substrates of thrombin (Le Bonniec, B. F., Myles, T., Johnson, T., Knight, C. G., Tapparelli, C., and Stone, S. R. (1996) Biochemistry 35, 7114-7122), nor within protein sequences that are natural substrates of thrombin (Rose, T. and Di Cera, E. (2002) J. Biol. Chem. 277, 18875-18880; and Le Bonniec, B. F., Myles, T., Johnson, T., Knight, C. G., Tapparelli, C., and Stone, S. R. (1996) Biochemistry 35, 7114-7122). In contrast, an aromatic, especially phenylalanine, or a long-chain aliphatic residue at the $P_2'$ position was found to favor substrate cleavage (Le Bonniec, B. F., Myles, T., Johnson, T., Knight, C. G., Tapparelli, C., and Stone, S. R. (1996) Biochemistry 35, 7114-7122) and many protein substrates of thrombin contain a hydrophobic residue at the $P_2'$ site. Interestingly, a similar preference for long-chain hydrophobic residues was found for the $P_1'$ subsite of a bivalent peptide inhibitor of thrombin containing a terminally-blocked arginine as the active-site binding moiety (Slon-Usakiewicz, J. J., Sivaraman, J., Li, Y., Cygler, M., and Konishi, Y. (2000) Biochemistry 39, 2384-2391). Surprisingly, many phage sequences contain an alanine at the $P_4$ position (Table 3), which is not a favorable residue for substrate turnover (Backes, B. J., Harris, J. L., Leonetti, F., Craik, C. S., and Ellman, J. A. (2000) Nat. Biotechnol. 18, 187-193; Edwards, P. D., Mauger, R. C., Cottrell, K. M., Morris, F. X., Pine, K. K., Sylvester, M. A., Scott, C. W., and Furlong, S. T. (2000) Bioorg. Med. Chem. Lett. 10, 2291-2294; and Furlong, S. T., Mauger, R. C., Strimpler, A. M., Liu, Y. P., Morris, F. X., and Edwards, P. D. (2002) Bioorg.

*Med. Chem.* 10, 3637-3647) and neither found in sequences of natural substrates of thrombin (Ni, F., Zhu, Y., and Scheraga, H. A. (1995) *J. Mol. Biol.* 252, 656-671; and Rose, T. and Di Cera, E. (2002) *J. Biol. Chem.* 277, 18875-18880).

All representative peptides derived from panning hits showed strong anticlotting activities in the low nanomolar range (Table 1). Two of the five phage-derived peptides, i.e. FQ22-M and GS-IQ22-I, had anticlotting $IC_{50}$ values as low as 10 nM, an inhibitory potency that is close to that of hirulog (Table 1). Very interestingly, however, the FQ22-M and GS-IQ22-I peptides had rather large $K_i$ values for the inhibition of the amidolytic activity of thrombin (Table 1). Even the less potent peptide, FN22-I, exhibited a $K_i$ value (360 nM), which is eight times the $IC_{50}$ (45 nM) for clotting inhibition. These consistently increased $K_i$ values over the anticlotting $IC_{50}$'s indicate that these bivalent peptides may also bind to alternative sites on thrombin, through the $P_1$-$P_4$ and $P_1'$-$P_3'$ sequences, other than the catalytic active site. In fact, the very potent GS-IQ22-I peptide containing residues Gly-Ser before the putative Ile($P_4$) residue may not even bind to the active site of thrombin as the amidolytic activity of thrombin was little affected in the presence of GS-IQ22-I up to 400 nM in concentration (Table 1). Very surprisingly, the truncated peptide, IQ22-I, being devoid of only the Gly-Ser residues, returned to "normal" thrombin binding as it had similar anticlotting and anti-amidolytic activities. Such active site binding favored by the IQPR sequence may be driven by the formation of stronger hydrogen-bonding and electrostatic interactions involving the primary amine of an unblocked Ile($P_4$) residue, as observed for the (d)FPR tripeptide motifs (Rehse, P. H., Steinmetzer, T., Li, Y., Konishi, Y., and Cygler, M. (1995) *Biochemistry* 34, 11537-11544; and Nienaber, V. L., Mersinger, L. J., and Kettner, C. A. (1996) *Biochemistry* 35, 9690-9699). The GS-AV22-I peptide also had the normal bivalent mode of binding to thrombin (Table 1), but it very interestingly contains the Gly-Ser residues, which blocks the N-terminus of the alanine at the $P_4$ position and would make it impossible to engage in enhanced hydrogen bonding interactions (Nienaber, V. L., Mersinger, L. J., and Kettner, C. A. (1996) *Biochemistry* 35, 9690-9699). In all, some selected phage peptides appear to utilize alternative binding sites on thrombin to achieve synergistic binding and efficient inhibition of proteolytic cleavages of macromolecular substrates (e.g. fibrinogen) by thrombin. Indeed, it was reported recently that a peptide derived from the N-terminus of the thrombin receptor PAR3 also confers strong inhibition of the fibrinogen-clotting activity while leaving open the catalytic active site of thrombin (Owen, W. G. (2003) *Biochem. Biophys. Res. Commun.* 305, 166-168).

The frequent occurrence of Ala at $P_4$ in phage sequences (Table 3) is of further interest since thrombin is not known to favor this residue and yet the GSAVPR sequence (as in the GS-AV22-I peptide) confers enhanced bridge-binding inhibition of the thrombin active site (Table 1). On the other hand, thrombin is a highly allosteric enzyme, featuring, in addition to the catalytic active site, a regulatory protein binding site (exosite 1), also called the amino-binding exosite (ABE) or the fibrinogen-recognition exosite (FRE), which the hirudin sequence of the bivalent peptides targets and binds. Thrombin also has a sodium-binding site in the vicinity of the catalytic active site, responsible for additional complexities of thrombin function (Dang, O. D., Vindigni, A., and Di Cera, E. (1995) *Proc. Natl. Acad. Sci. U.S.A.* 92, 5977-5981). It was shown in a recent work that the active site of thrombin could assume a closed and inactive conformation, which in solution may be in equilibrium with active conformations of thrombin (Huntington, J. A. and Esmon, C. T. (2003) *Structure. (Camb.)* 11, 469479). This inactive conformation of thrombin has an occluded $P_4$-binding subsite, leaving little room for the bulky side chain of an aromatic or aliphatic $P_4$ residue. The binding properties and catalytic efficiencies of the thrombin active site may thereby be linked through fast interconversions between active and inactive conformations to the occupancies of regulatory binding sites, especially ligand binding at the fibrinogen-recognition exosite. As such, it is conceivable that binding of the GS-AV22-I peptide may stabilize selectively the inactive and closed conformation of thrombin, achieving inhibition of catalysis indirectly instead of direct binding to catalytically active structures at the active site.

The new peptide inhibitors of thrombin of the present invention are composed of natural amino acids and can be prepared more cost-effectively by recombinant DNA technology. Moreover, a controlled balance between thrombin inhibition and peptide cleavage (after the Arg-Pro bond) can result in potent and more efficacious anticoagulation with reduced undesirable side effects.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An isolated or purified polypeptide inhibitor of thrombin consisting of all naturally-occurring amino acids and comprising the amino acid sequence as set forth in SEQ ID NO: 29.

* * * * *